United States Patent
Buckley et al.

(10) Patent No.: US 7,538,226 B2
(45) Date of Patent: May 26, 2009

(54) (1S,5S)-3-(5,6-DICHLORO-3-PYRIDINYL)-3,6-DIAZABICYCLO[3.2.0]HEPTANE

(75) Inventors: Michael J. Buckley, McHenry, IL (US); Jianguo Ji, Libertyville, IL (US); Geoff G. Z. Zhang, Libertyville, IL (US); Rodger F. Henry, Wildwood, IL (US); Weili W. Wang, Buffalo Grove, IL (US); Gregory S. Wayne, Vernon Hills, IL (US); Wenke Li, Gurnee, IL (US); Timothy B. Towne, Lindenhurst, IL (US); Steven J. Wittenberger, Mundelein, IL (US); Steven M. Hannick, Highland Park, IL (US); Brian J. Kotecki, Oak Creek, WI (US); Bryan S. Macri, Gurnee, IL (US); Timothy A. Robbins, Grayslake, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 11/838,745

(22) Filed: Aug. 14, 2007

(65) Prior Publication Data

US 2008/0070891 A1 Mar. 20, 2008

Related U.S. Application Data

(60) Division of application No. 11/176,087, filed on Jul. 7, 2005, now Pat. No. 7,354,937, which is a continuation-in-part of application No. 10/898,441, filed on Jul. 23, 2004, now abandoned, which is a continuation-in-part of application No. 10/851,917, filed on May 21, 2004, now abandoned.

(60) Provisional application No. 60/473,530, filed on May 27, 2003.

(51) Int. Cl.
C07D 487/04 (2006.01)
(52) U.S. Cl. .................................. 546/276.7
(58) Field of Classification Search ............... 546/276.7
See application file for complete search history.

(56) References Cited

U.S. PATENT DOCUMENTS

2004/0242641 A1 12/2004 Buckley et al.
2004/0242644 A1 12/2004 Buckley et al.
2005/0261348 A1 11/2005 Buckley et al.
2006/0035936 A1 2/2006 Buckley et al.

FOREIGN PATENT DOCUMENTS

WO 01/81347 11/2001
WO 2004/106342 12/2004

OTHER PUBLICATIONS

Arneric, et al., "Cholingeric channel modulators as a novel therapeutic strategy for Alzheimer's disease," Exp. Opin. Invest. Drugs 5(1): 79-100 (1996).
Arneric, et al., "Neuronal nicotinic acetycholine receptors," Psychopharmacology: The Fourth Generation of Progress 95-110 (1995).
Carty, et al., "Cox-2 inhibitors. Potential for reducing NSAID side-effects in treating inflammatory disease," Emerging Drugs: The Prospect for Improved Medicines, Annual Executive Briefing; Chapter 19: 391-411 (1996).
Chaplan, et al., "Quantitative assessment of tactile allodynia in the rat paw," Journal of Neuroscience Methods 53: 55-63 (1994).
Cherny, et al., "Opioid Analgesics, Comparative features and prescribing guidelines," Drugs 51(5): 713-737 (1996).
Decker, et al., "Effects of ABT-418, a novel cholinergic channel ligand, on place learning in septal-lesioned rats," European Journal of Pharmacology 261: 217-222 (1994).
Dray, et al., "New pharmacological strategies for pain relief," Annu. Rev. Pharmacol. Toxicol. 36: 253-280 (1996).
Dray, et al., "Pharmacology of chronic pain," TiPS 15: 190-197 (1994).
Kim, et al., "An experimental model for peripheral neuropathy produced by segmental spinal nerve ligation in the rat," Pain 50: 355-363 (1992).
Lindstrom, "Nicotinic acetylcholine receptors in health and disease," Molecular Neurobiology 15: 193-222 (1997).
Lloyd, et al., "The potential of subype-selective neuronal nicotinic acetylcholine receptor agonists as therapeutic agents," Life Sciences 62(17/18): 1601-1606 (1998).
Lukas, "Expression of ganglia-type nicotinic acetylcholine receptors and nicotinic ligand binding sites by cells of the IMR-32 human neuroblastoma clonal line," Journal of Pharmacology and Experimental Therapeutics 265(1): 294-302 (1993).
Pabreza, et al, "[$^3$H]cytosine binding to nicotinic cholinergic receptors in brain," Molecular Pharmacology 39:9-12 (1990).
Prescott, et al., Methods in Cell Biology, vol. XIV, Academic Press, New York, NY, p. 33 et seq. (1976).
Williams, et al., "Beyond the tobacco debate: dissecting out the therapeutic potential of nicotine," Exp. Opin. Invest. Drugs 5(8): 1035-1045 (1996).
Williams, et al., "Emerging molecular approaches to pain therapy," Journal of Medicinal Chemistry 42(9): 1481-1500 (1999).

*Primary Examiner*—Patricia L Morris
(74) *Attorney, Agent, or Firm*—Antonia M. Holland

(57) ABSTRACT

The present invention discloses (1S,5S)-3-(5,6-dichloro-3-pyridinyl)-3,6-diazabicyclo[3.2.0]heptane, salts thereof, and its use to treat pain and other disorders associated with the nicotinic acetylcholine receptor.

2 Claims, 22 Drawing Sheets

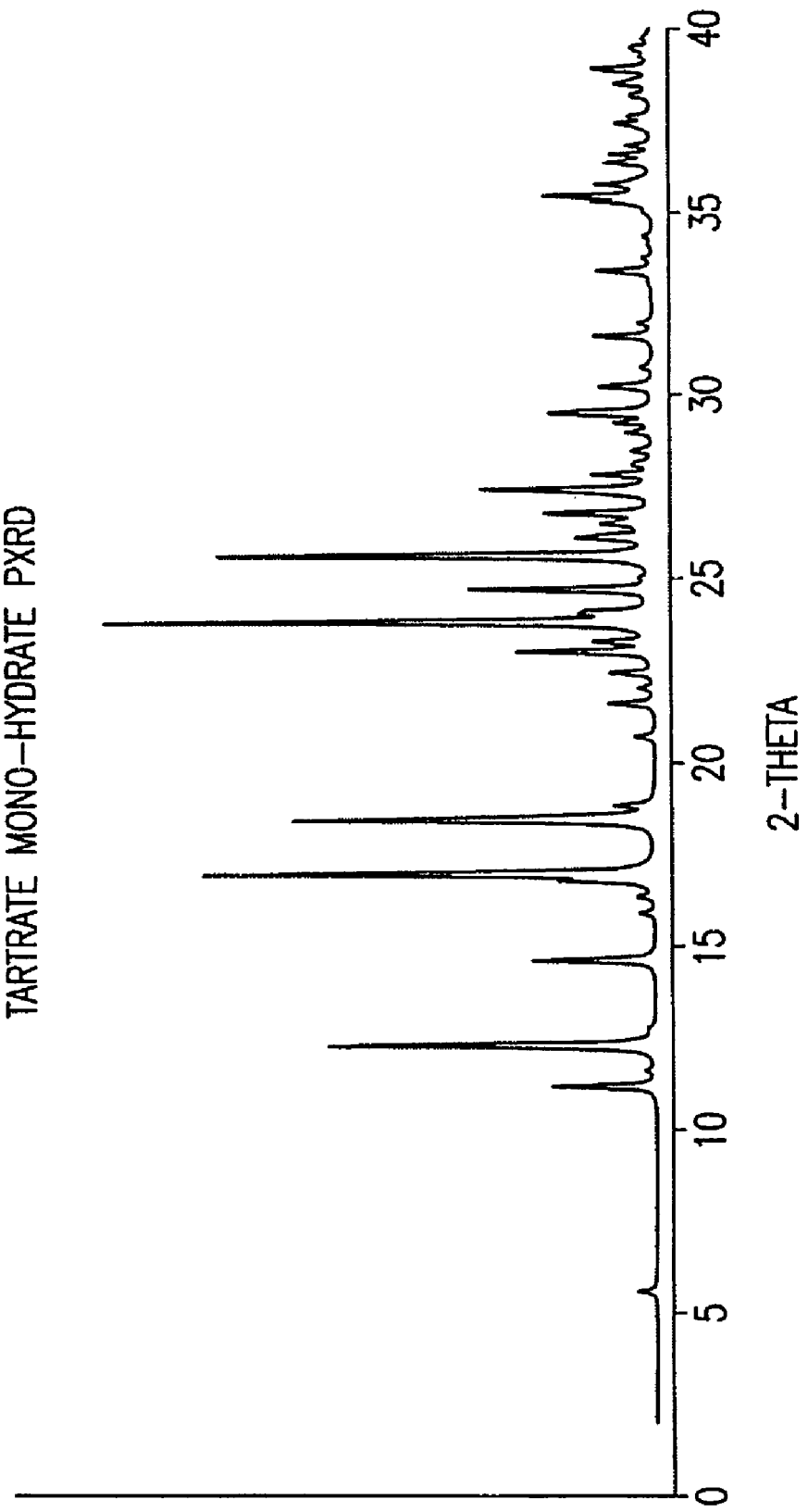

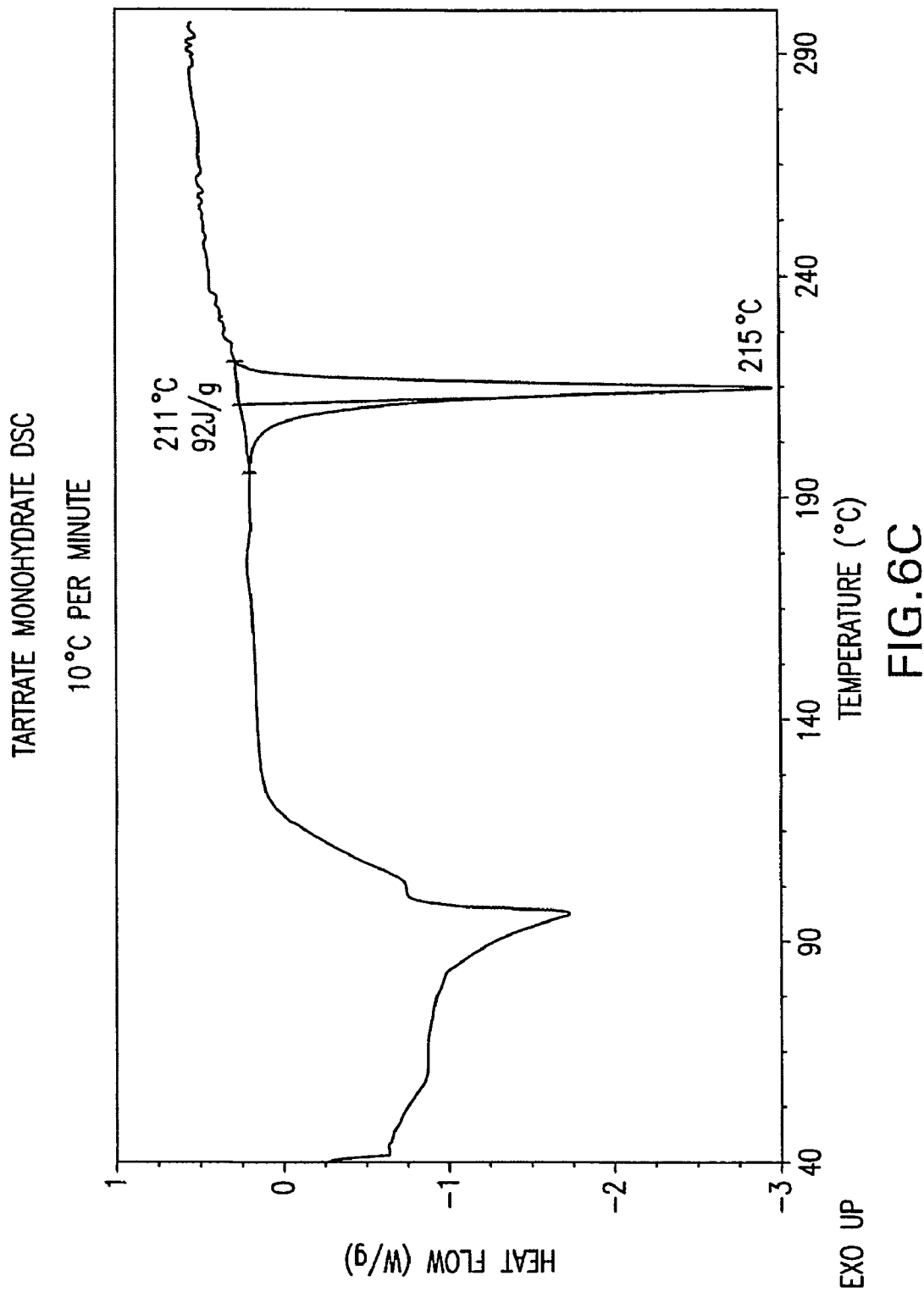

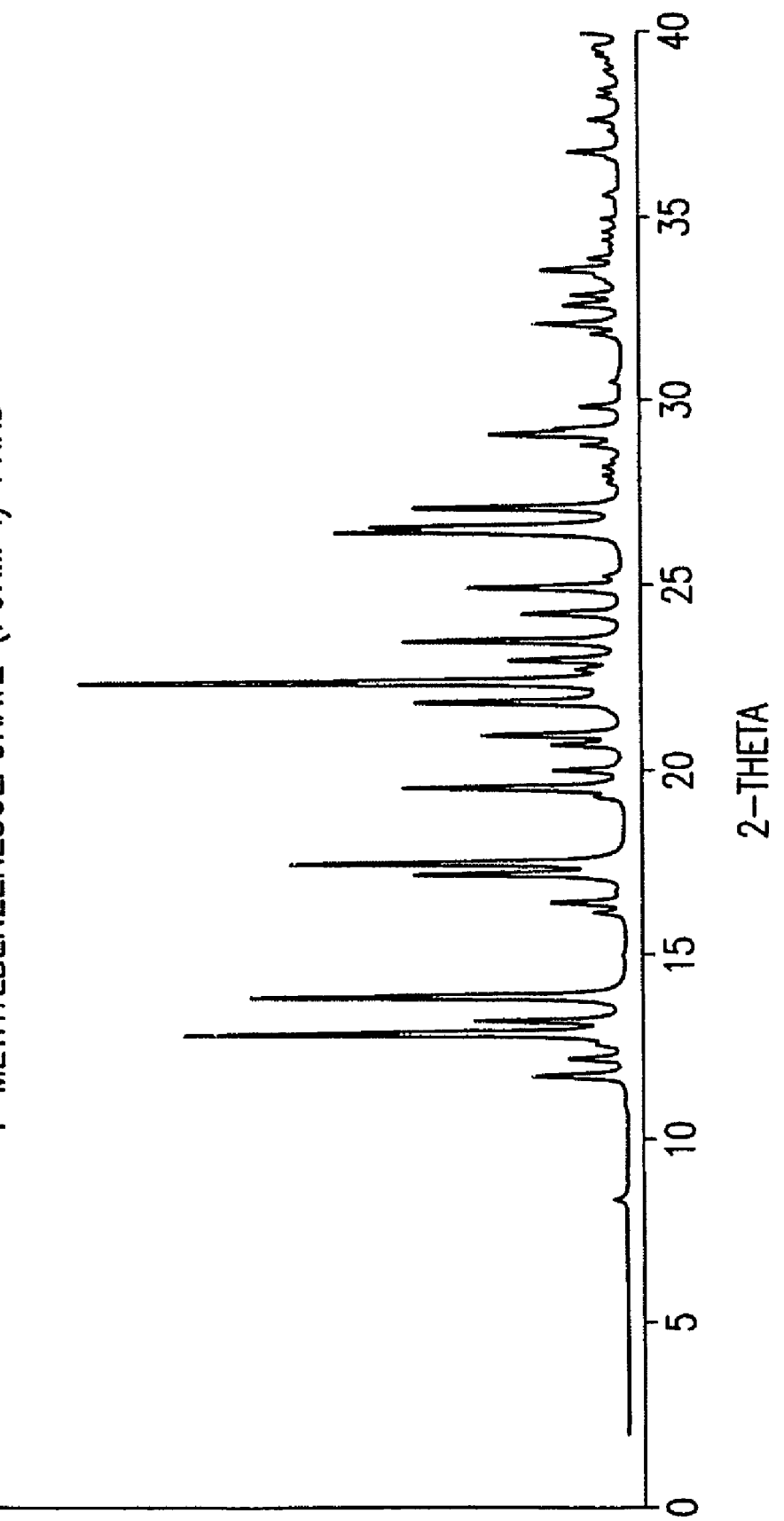

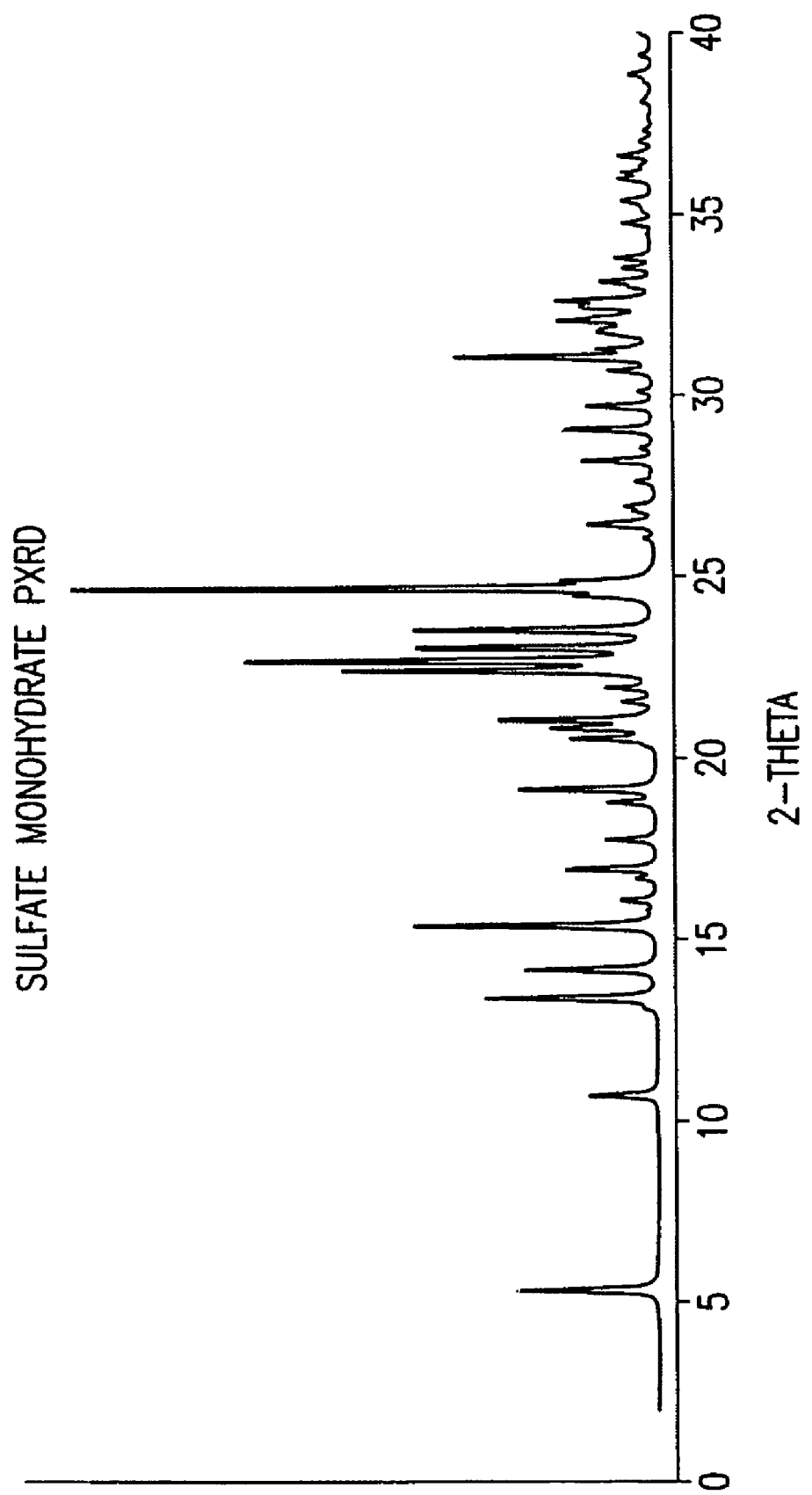

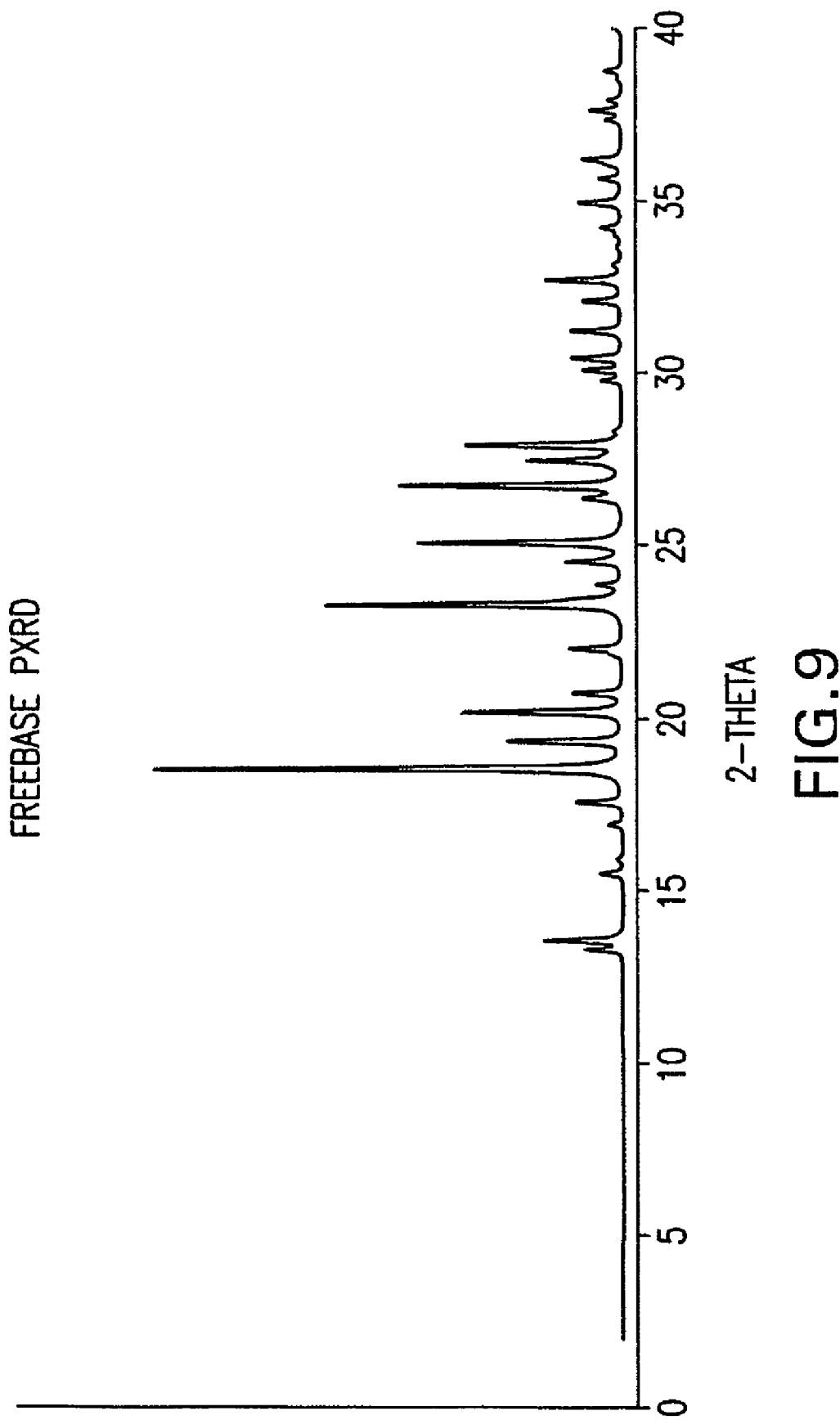

# (1S,5S)-3-(5,6-DICHLORO-3-PYRIDINYL)-3,6-DIAZABICYCLO[3.2.0]HEPTANE

This application is a divisional of U.S. patent application Ser. No. 11/176,087, filed Jul. 7, 2005, which is a continuation-in-part of U.S. patent application Ser. No. 10/898,441, filed Jul. 23, 2004, which is a continuation-in-part of U.S. patent application Ser. No. 10/851,917, filed May 21, 2004, which claims the benefit of U.S. patent application Ser. No. 60/473,530, filed May 27, 2003, each of which is hereby incorporated by reference.

FIELD OF THE INVENTION

The present invention is directed to (1S,5S)-3-(5,6-dichloro-3-pyridinyl)-3,6-diazabicyclo[3.2.0]heptane, salts thereof, and its use to treat pain, in particular, neuropathic pain.

BACKGROUND OF THE INVENTION

The search for potent and effective analgesics continues to be a significant research goal in the medical community. A substantial number of medical disorders and conditions produce pain as part of the disorder or condition. Relief of this pain is a major aspect of ameliorating or treating the overall disorder or condition. Pain and the possible alleviation thereof is also attributable to the individual patient's mental condition and physical condition.

Opioid and non-opioid drugs are the two major classes of analgesics (A. Dray and L. Urban, Ann. Rev. Pharmacol. Toxicol., 36:253-280, (1996)). Opioids, such as morphine, act at opioid receptors in the brain to block transmission of the pain signals in the brain and spinal cord (N. I. Cherney, Drug, 51:713-737, (1996)). Non-opioids such as non-steroid anti-inflammatory agents (NSAIDs) typically, but not exclusively, block the production of prostaglandins to prevent sensitization of nerve endings that facilitate the pain signal to the brain (Dray, et al., Trends in Pharmacol. Sci., 15:190-197, (1994); T. J. Carty and A. Marfat, "COX-2 Inhibitors. Potential for reducing NSAID side-effects in treating inflammatory diseases", Emerging Drugs: Prospect for Improved Medicines. (W. C. Bowman, J. D. Fitzgerald, and J. B. Taylor, eds.), Ashley Publications Ltd., London, Chap. 19., pp. 391-411).

Certain compounds, with primary therapeutic indications other than analgesia, have been shown to be effective in some types of pain control. These are classified as analgesic adjuvants, and include tricyclic antidepressants (TCAs) and some anticonvulsants such as gabapentin (Williams et al., J. Med. Chem., 42:1481-1500 (1999)). They are used increasingly for treatment of pain, especially for pain resulting from nerve injury due to trauma, radiation, or disease.

(1S,5S)-3-(5,6-Dichloro-3-pyridinyl)-3,6-diazabicyclo[3.2.0]heptane, and its salts, are novel compounds that demonstrate utility in treating pain and disorders associated with the nicotinic acetylcholine receptor (nAChR). (1S,5S)-3-(5,6-Dichloro-3-pyridinyl)-3,6-diazabicyclo[3.2.0]heptane, and salts thereof, may also have utility when administered in combination with an opioid such as morphine, a non-steroid anti-inflammatory agent such as aspirin, a tricyclic antidepressant, or an anticonvulsant such as gabapentin or pregabalin for treating pain and disorders associated with the nicotinic acetylcholine receptor.

WO 01-81347 discloses diazabicyclo[3.2.0]heptanes that are analgesic agents.

BRIEF DESCRIPTION OF THE DRAWINGS

FIG. 6B is the powder X-ray diffractogram of (1S,5S)-3-(5,6-dichloro-3-pyridinyl)-3,6-diazabicyclo[3.2.0]heptane L-tartrate monohydrate.

FIG. 6C is the differential scanning calorimetry thermogram of (1S,5S)-3-(5,6-dichloro-3-pyridinyl)-3,6-diazabicyclo[3.2.0]heptane L-tartrate monohydrate.

FIG. 7B is the powder X-ray diffractogram of (1S,5S)-3-(5,6-dichloro-3-pyridinyl)-3,6-diazabicyclo[3.2.0]heptane 4-methylbenzenesulfonate (Form I).

FIG. 8 is the powder X-ray diffractogram of (1S,5S)-3-(5,6-dichloro-3-pyridinyl)-3,6-diazabicyclo[3.2.0]heptane sulfate monohydrate.

FIG. 9 is the powder X-ray diffractogram of (1S,5S)-3-(5,6-dichloro-3-pyridinyl)-3,6-diazabicyclo[3.2.0]heptane.

FIGS. 7, 7B, 8, and 9 were determined from the single cell crystal data of their respective compounds.

SUMMARY OF THE INVENTION

Figure 1:
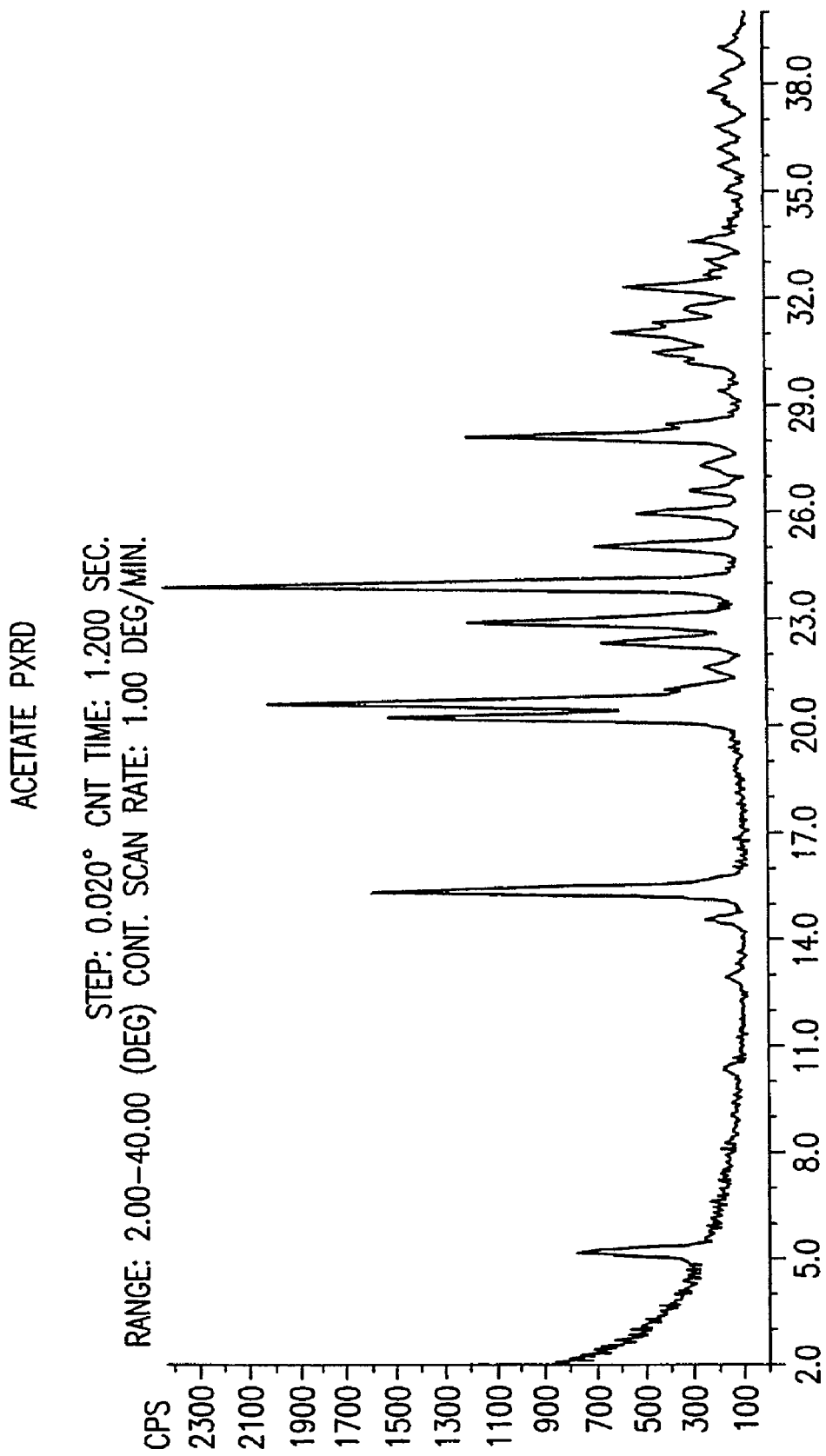
FIG. 1 is the powder X-ray diffractogram of (1S,5S)-3-(5,6-dichloro-3-pyridinyl)-3,6-diazabicyclo[3.2.0]heptane acetate.

The present invention discloses (1S,5S)-3-(5,6-dichloro-3-pyridinyl)-3,6-diazabicyclo[3.2.0]heptane or a pharmaceutically acceptable salt or prodrug thereof and its use to treat pain, in particular, neuropathic pain.

DETAILED DESCRIPTION OF THE INVENTION

In its principle embodiment, the present invention discloses (1S,5S)-3-(5,6-dichloro-3-pyridinyl)-3,6-diazabicyclo[3.2.0]heptane or a pharmaceutically acceptable salt or prodrug thereof.

In another embodiment, the present invention relates to a method of treating pain including, but not limited to, neuropathic pain comprising administering to a mammal a therapeutically effective amount of (1S,5S)-3-(5,6-dichloro-3-pyridinyl)-3,6-diazabicyclo[3.2.0]heptane or a pharmaceutically acceptable salt or prodrug thereof.

In another embodiment, the present invention relates to a method of treating pain including, but not limited to, neuropathic pain comprising administering to a mammal a therapeutically effective amount of (1S,5S)-3-(5,6-dichloro-3-pyridinyl)-3,6-diazabicyclo[3.2.0]heptane or a pharmaceutically acceptable salt or prodrug thereof in combination with an opioid including, but not limited to morphine.

In another embodiment, the present invention relates to a method of treating pain including, but not limited to, neuropathic pain comprising administering to a mammal a therapeutically effective amount of (1S,5S)-3-(5,6-dichloro-3-pyridinyl)-3,6-diazabicyclo[3.2.0]heptane or a pharmaceutically acceptable salt or prodrug thereof in combination with a non-steroid anti-inflammatory agent including, but not limited to aspirin.

In another embodiment, the present invention relates to a method of treating pain including, but not limited to, neuropathic pain comprising administering to a mammal a therapeutically effective amount of (1S,5S)-3-(5,6-dichloro-3-pyridinyl)-3,6-diazabicyclo[3.2.0]heptane or a pharmaceutically acceptable salt or prodrug thereof in combination with an anticonvulsant including, but not limited to, gabapentin or pregabalin.

In another embodiment, the present invention relates to a method of treating pain including, but not limited to, neuropathic pain comprising administering to a mammal a therapeutically effective amount of (1S,5S)-3-(5,6-dichloro-3-pyridinyl)-3,6-diazabicyclo[3.2.0]heptane or a pharmaceutically acceptable salt or prodrug thereof in combination with a tricyclic antidepressant.

In another embodiment, the present invention relates to a method of treating Alzheimer's disease, Parkinson's disease, memory dysfunction, Tourette's syndrome, sleep disorders, attention deficit hyperactivity disorder, neurodegeneration, inflammation, neuroprotection, anxiety, depression, mania, schizophrenia, anorexia and other eating disorders, AIDS-induced dementia, epilepsy, urinary incontinence, substance abuse, smoking cessation or inflammatory bowel syndrome, comprising administering to a mammal a therapeutically effective amount of (1S,5S)-3-(5,6-dichloro-3-pyridinyl)-3,6-diazabicyclo[3.2.0]heptane or a pharmaceutically acceptable salt or prodrug thereof.

In another embodiment, the present invention relates to pharmaceutical compositions comprising (1S,5S)-3-(5,6-dichloro-3-pyridinyl)-3,6-diazabicyclo[3.2.0]heptane or a pharmaceutically acceptable salt thereof in combination with a pharmaceutically acceptable carrier.

In another embodiment, the present invention relates to a pharmaceutical composition for treating pain in a mammal comprising administering to a mammal a therapeutically effective amount of (1S,5S)-3-(5,6-dichloro-3-pyridinyl)-3,6-diazabicyclo[3.2.0]heptane, or a pharmaceutically acceptable salt thereof, in combination with a non-steroid anti-inflammatory agent.

In another embodiment, the present invention relates to a pharmaceutical composition for treating pain in a mammal comprising administering to a mammal a therapeutically effective amount of (1S,5S)-3-(5,6-dichloro-3-pyridinyl)-3,6-diazabicyclo[3.2.0]heptane or a pharmaceutically acceptable salt thereof, in combination with an opioid.

In another embodiment, the present invention relates to a pharmaceutical composition for treating pain in a mammal comprising administering to a mammal a therapeutically effective amount of (1S,5S)-3-(5,6-dichloro-3-pyridinyl)-3,6-diazabicyclo[3.2.0]heptane or a pharmaceutically acceptable salt thereof, in combination with a tricyclic antidepressant.

In another embodiment, the present invention relates to a pharmaceutical composition for treating pain in a mammal comprising administering to a mammal a therapeutically effective amount of (1S,5S)-3-(5,6-dichloro-3-pyridinyl)-3,6-diazabicyclo[3.2.0]heptane or a pharmaceutically acceptable salt thereof, in combination with an anticonvulsant.

In another embodiment, the present invention relates to salts of the (1S,5S)-3-(5,6-dichloro-3-pyridinyl)-3,6-diazabicyclo[3.2.0]heptane active agent. Specific salts of (1S,5S)-3-(5,6-dichloro-3-pyridinyl)-3,6-diazabicyclo[3.2.0]heptane contemplated as part of the invention include, for example, acetate, citrate, fumarate, hemicitrate, hydrochloride, maleate, methanesulfonate, 4-methylbenzenesulfonate, sulfate, L-tartrate, and trifluoroacetate.

In another embodiment, the present invention relates to substantially pure salts of the (1S,5S)-3-(5,6-dichloro-3-pyridinyl)-3,6-diazabicyclo[3.2.0]heptane active agent. Specific substantially pure salts of (1S,5S)-3-(5,6-dichloro-3-pyridinyl)-3,6-diazabicyclo[3.2.0]heptane contemplated as part of the invention include, for example, acetate, citrate, fumarate, hemicitrate, hydrochloride, maleate, methanesulfonate, 4-methylbenzenesulfonate, sulfate, L-tartrate, and trifluoroacetate.

(1S,5S)-3-(5,6-Dichloro-3-pyridinyl)-3,6-diazabicyclo[3.2.0]heptane acetate can be identified by its powder X-ray diffraction pattern in accordance with the Brief Description of the Drawings (FIG. 1).

Figure 1A:
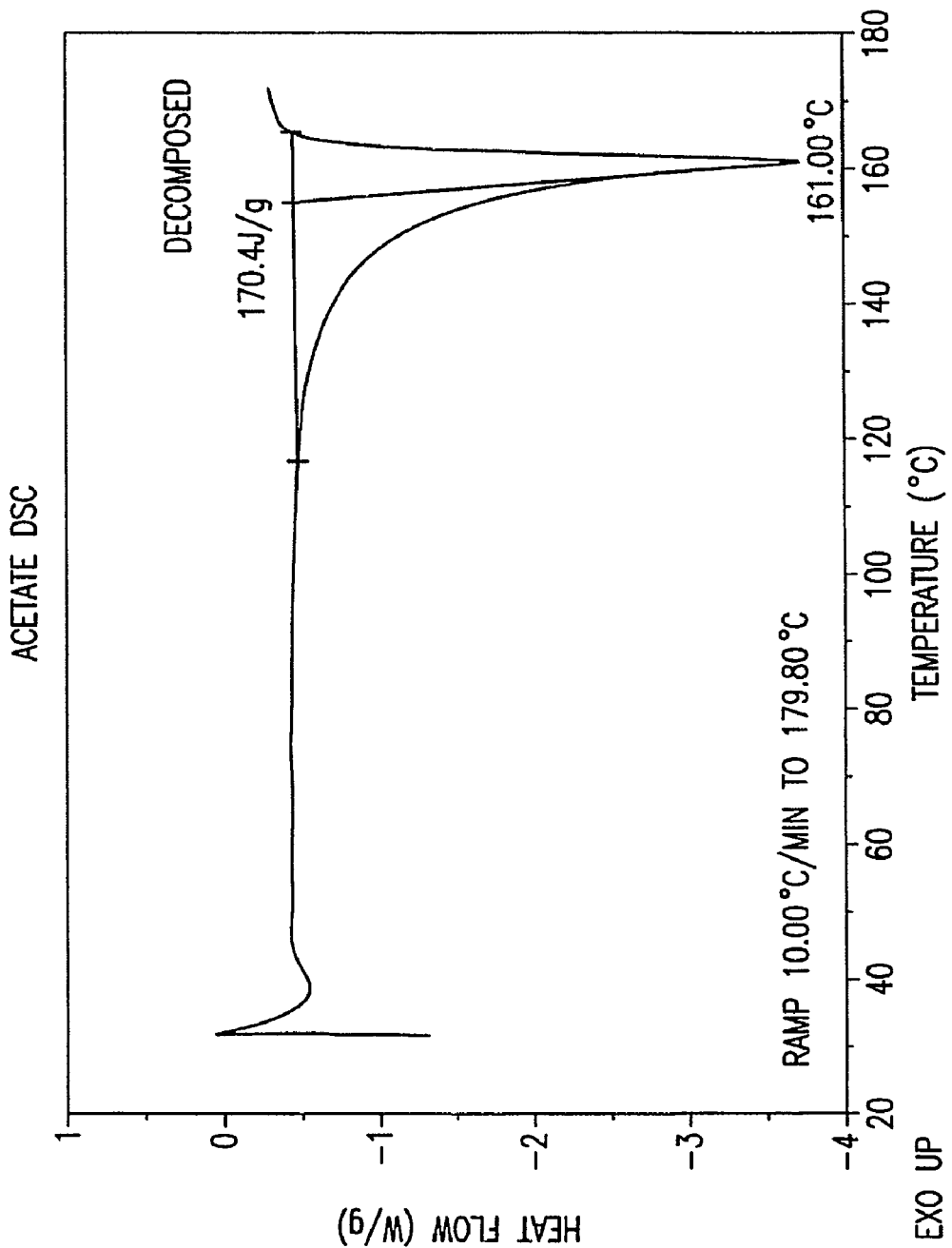
FIG. 1A is the differential scanning calorimetry (DSC) thermogram of (1S,5S)-3-(5,6-dichloro-3-pyridinyl)-3,6-diazabicyclo[3.2.0]heptane acetate.

Differential scanning calorimetry analysis of (1S,5S)-3-(5,6-dichloro-3-pyridinyl)-3,6-diazabicyclo[3.2.0]heptane acetate provided melt/decomposition at 161.0° C. (FIG. 1A). The sample size was 2.9550 mg.

Figure 2:
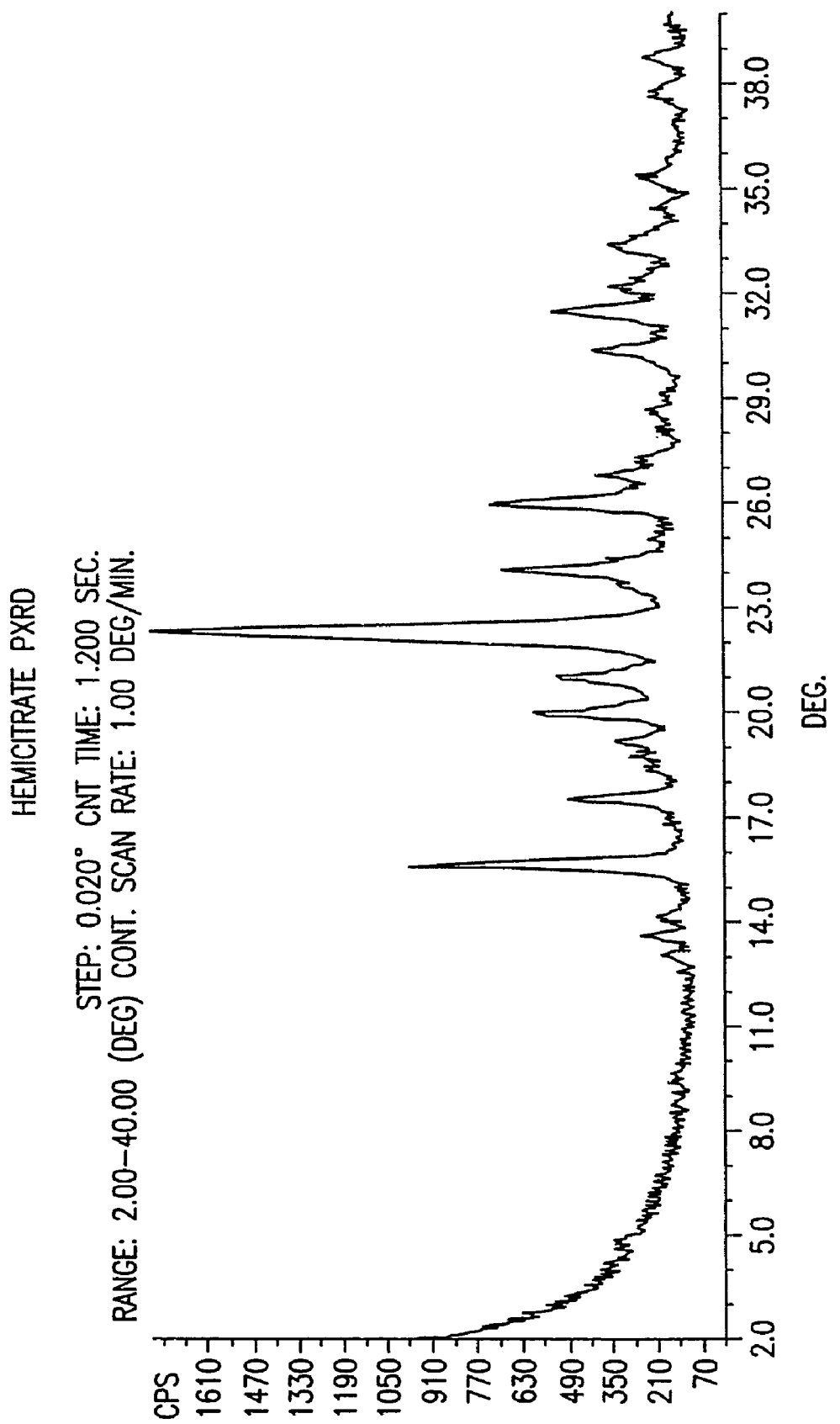
FIG. 2 is the powder X-ray diffractogram of (1S,5S)-3-(5,6-dichloro-3-pyridinyl)-3,6-diazabicyclo[3.2.0]heptane hemicitrate.

(1S,5S)-3-(5,6-Dichloro-3-pyridinyl)-3,6-diazabicyclo[3.2.0]heptane hemicitrate can be identified by its powder X-ray diffraction pattern in accordance with the Brief Description of the Drawings (FIG. 2).

Figure 2A:
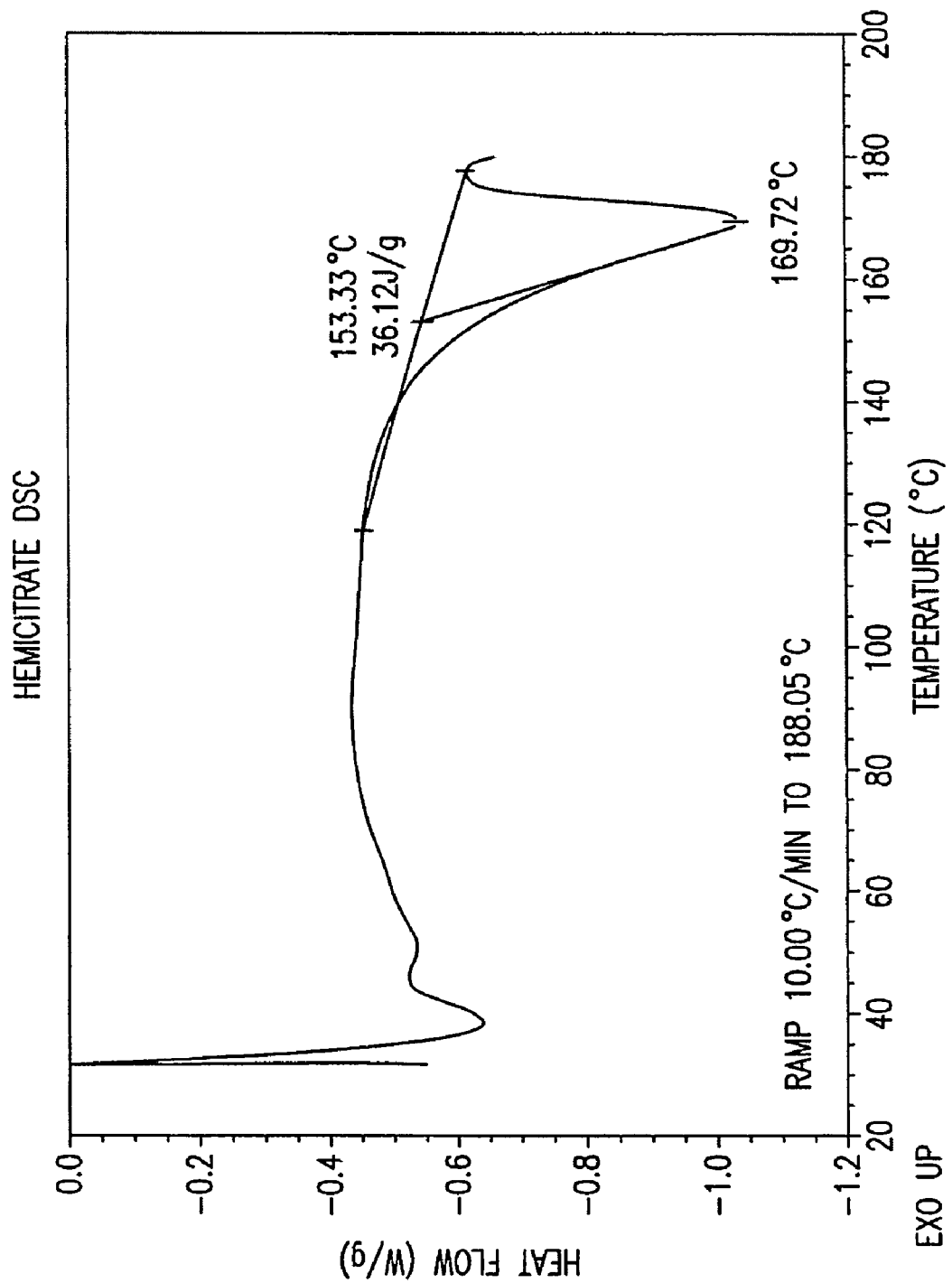
FIG. 2A is the differential scanning calorimetry thermogram of (1S,5S)-3-(5,6-dichloro-3-pyridinyl)-3,6-diazabicyclo[3.2.0]heptane hemicitrate.

Differential scanning calorimetry analysis of (1S,5S)-3-(5,6-dichloro-3-pyridinyl)-3,6-diazabicyclo[3.2.0]heptane hemicitrate provided melt/decomposition at 169.72° C. (FIG. 2A). The sample size was 3.2450 mg.

Figure 3:
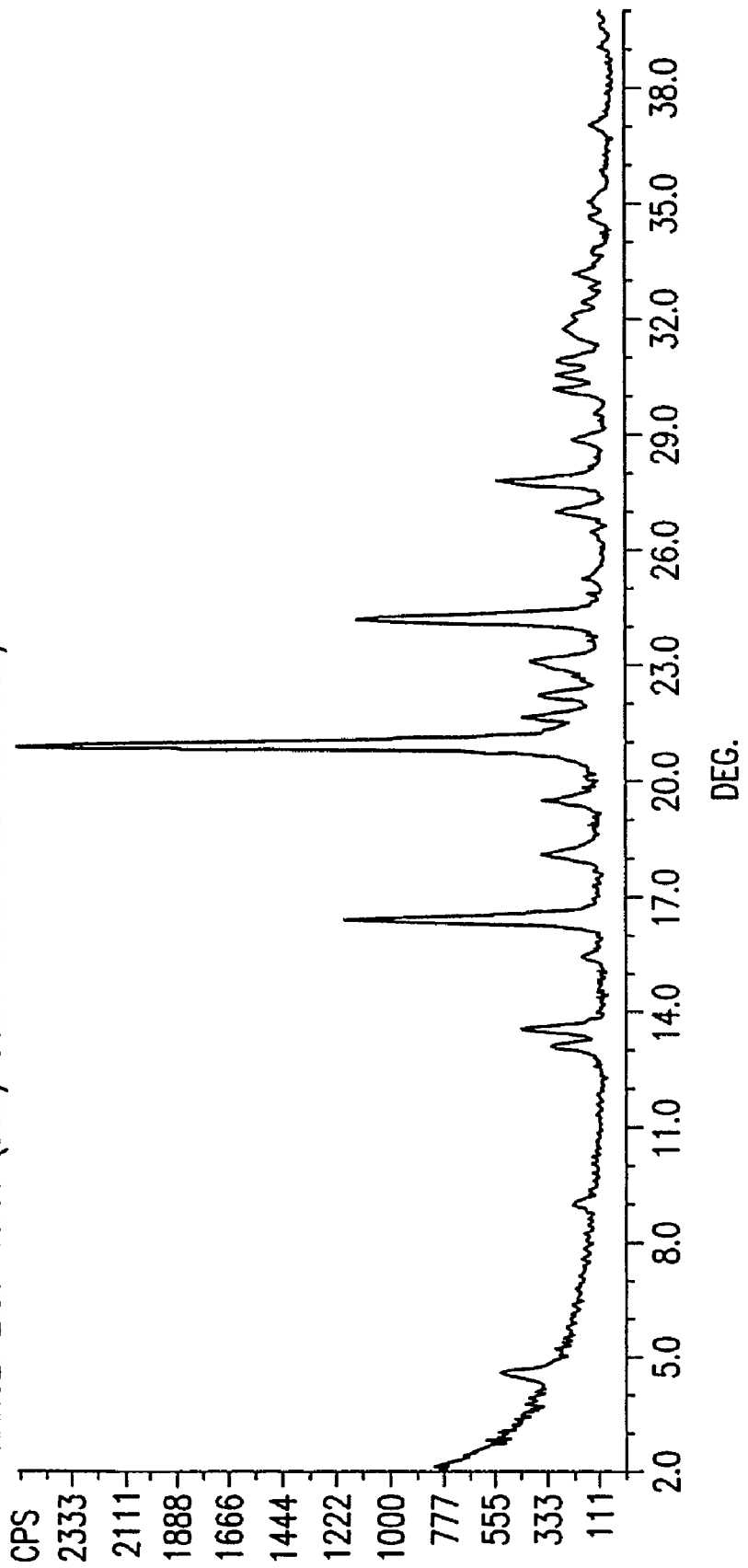
FIG. 3 is the powder X-ray diffractogram of (1S,5S)-3-(5,6-dichloro-3-pyridinyl)-3,6-diazabicyclo[3.2.0]heptane methanesulfonate.

(1S,5S)-3-(5,6-Dichloro-3-pyridinyl)-3,6-diazabicyclo[3.2.0]heptane methanesulfonate can be identified by its powder X-ray diffraction pattern in accordance with the Brief Description of the Drawings (FIG. 3).

Differential scanning calorimetry analysis of (1S,5S)-3-(5,6-dichloro-3-pyridinyl)-3,6-diazabicyclo[3.2.0]heptane methanesulfonate provided melt/decomposition at 167.23°

Figure 3A:
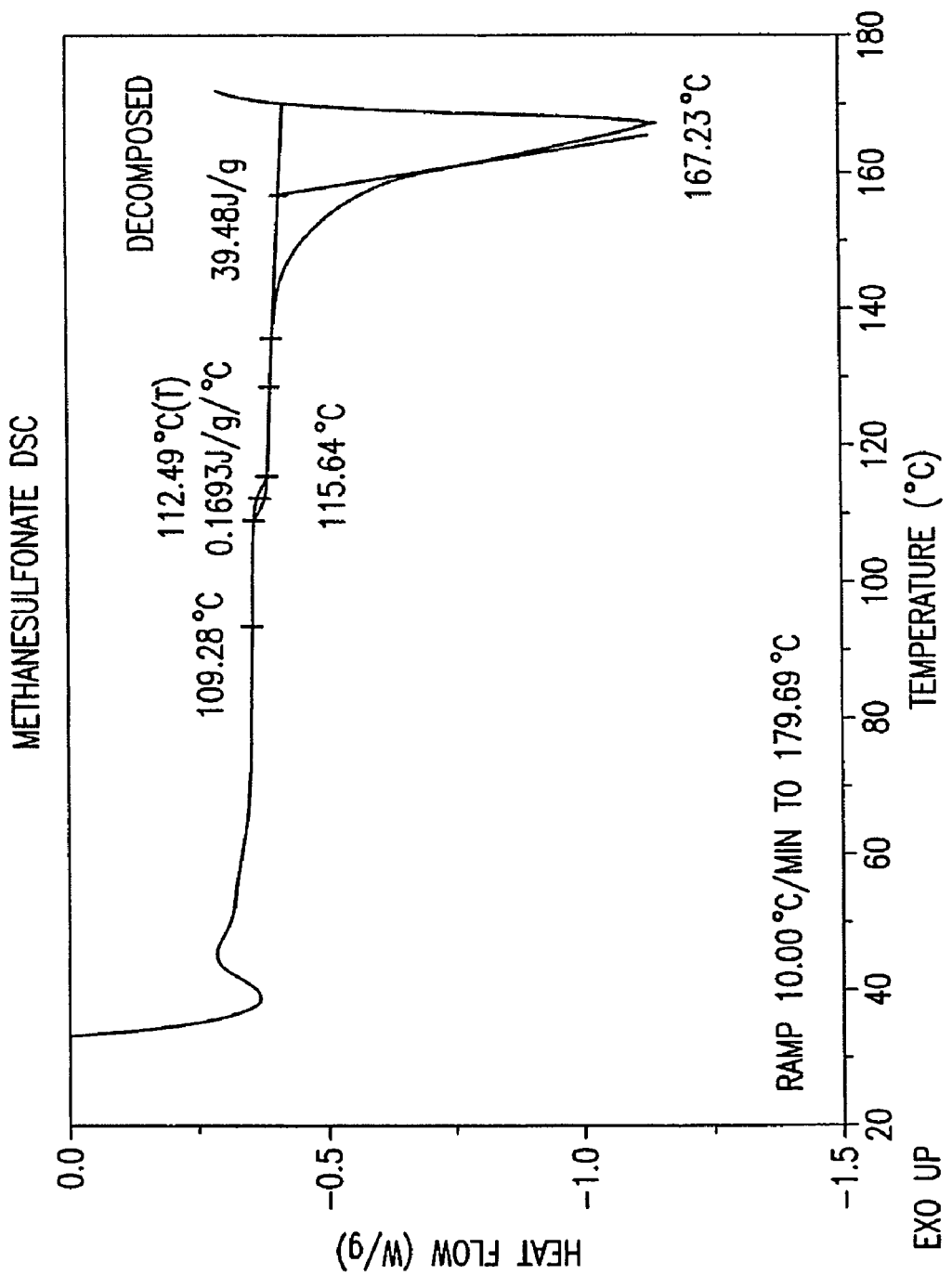
FIG. 3A is the differential scanning calorimetry thermogram of (1S,5S)-3-(5,6-dichloro-3-pyridinyl)-3,6-diazabicyclo[3.2.0]heptane methanesulfonate.

C. (FIG. 3A). DSC shows that the glass transition temperature is at about 112° C. The sample size was 3.0600 mg.

Figure 4:
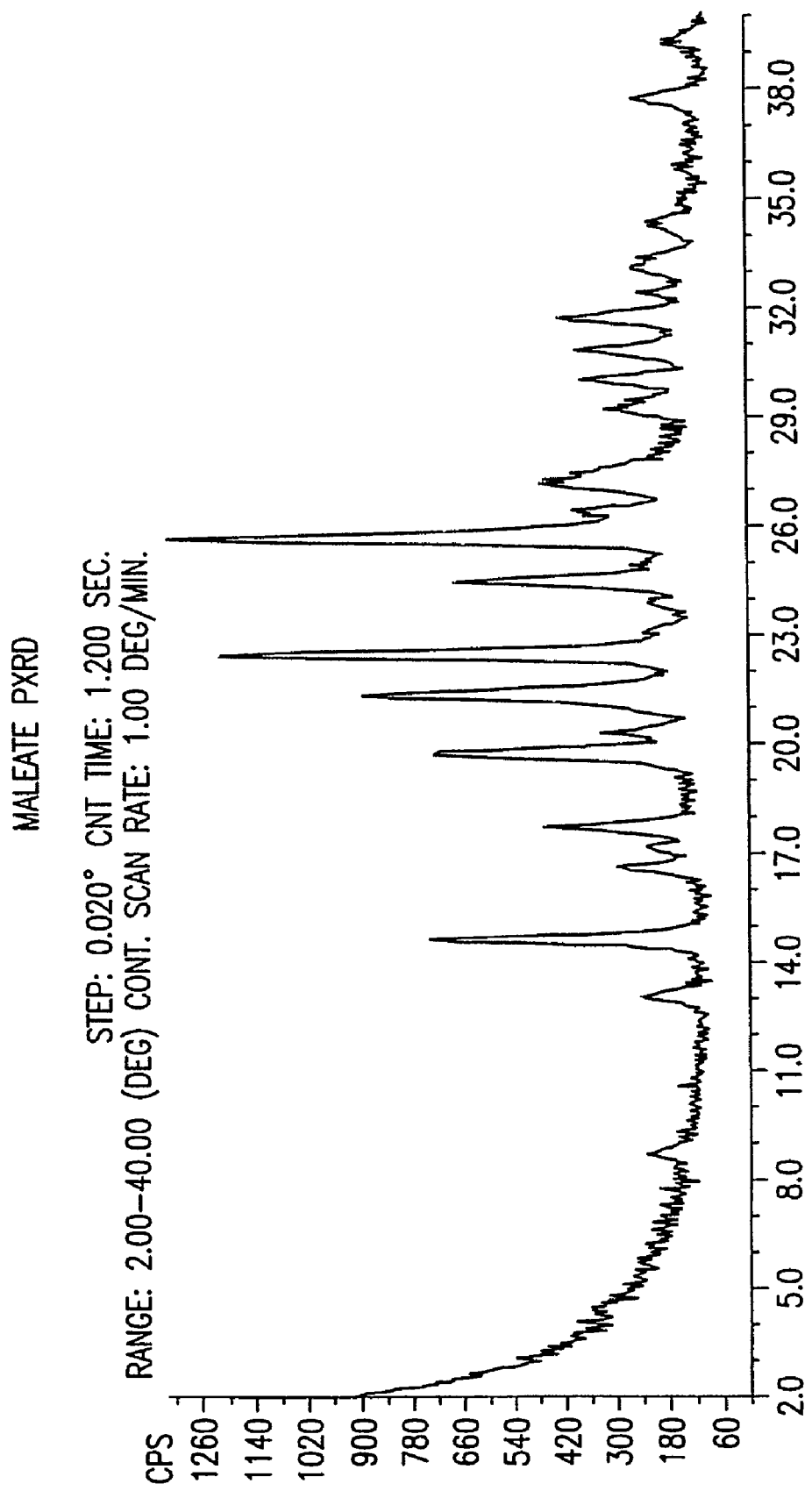
FIG. 4 is the powder X-ray diffractogram of (1S,5S)-3-(5,6-dichloro-3-pyridinyl)-3,6-diazabicyclo[3.2.0]heptane maleate.

(1S,5S)-3-(5,6-Dichloro-3-pyridinyl)-3,6-diazabicyclo[3.2.0]heptane maleate can be identified by its powder X-ray diffraction pattern in accordance with the Brief Description of the Drawings (FIG. 4).

Figure 4A:
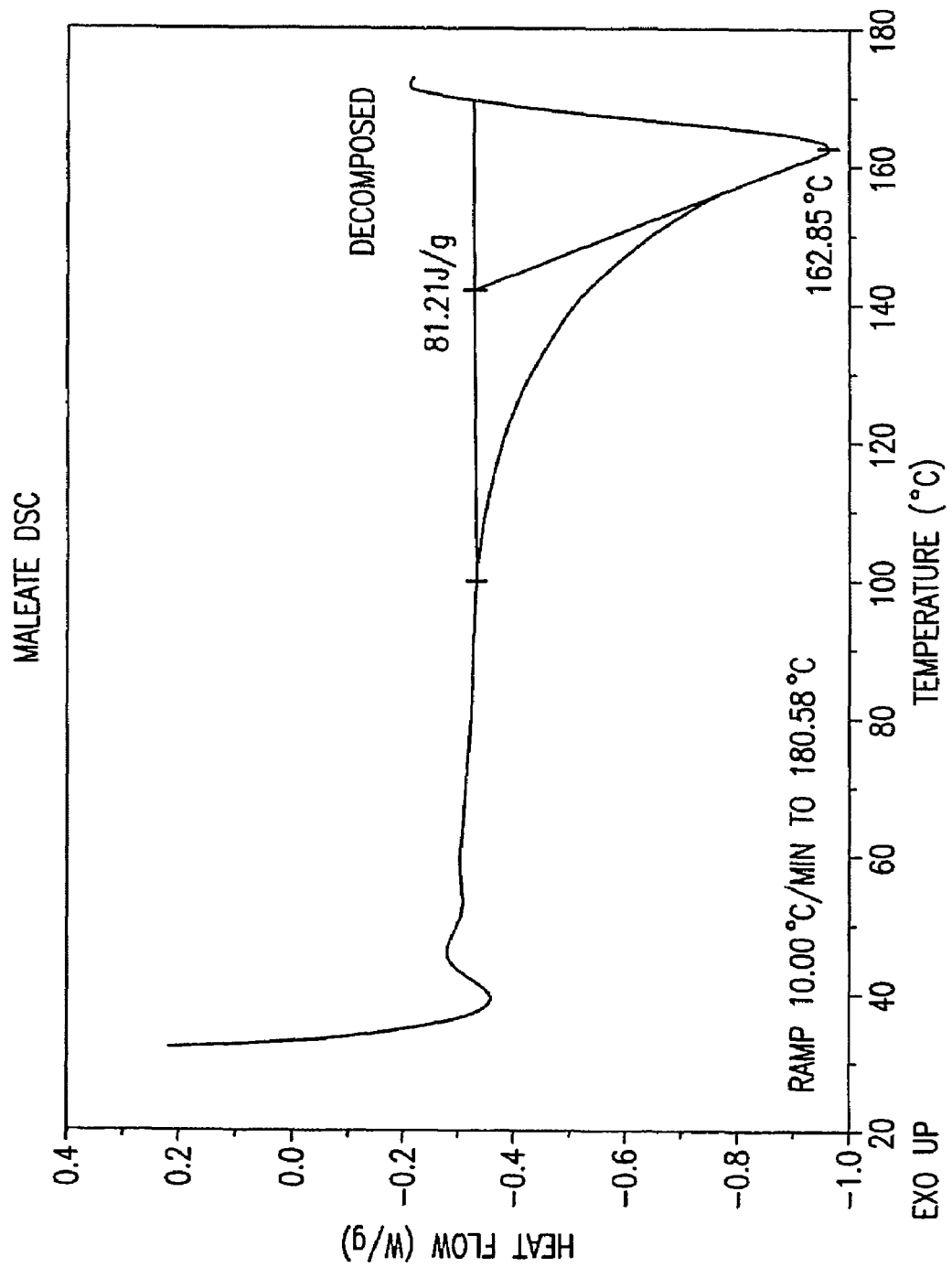
FIG. 4A is the differential scanning calorimetry thermogram of (1S,5S)-3-(5,6-dichloro-3-pyridinyl)-3,6-diazabicyclo[3.2.0]heptane maleate.

Differential scanning calorimetry analysis of (1S,5S)-3-(5,6-dichloro-3-pyridinyl)-3,6-diazabicyclo[3.2.0]heptane maleate provided melt/decomposition at 162.85° C. (FIG. 4A). The sample size was 3.7110 mg.

Figure 5:
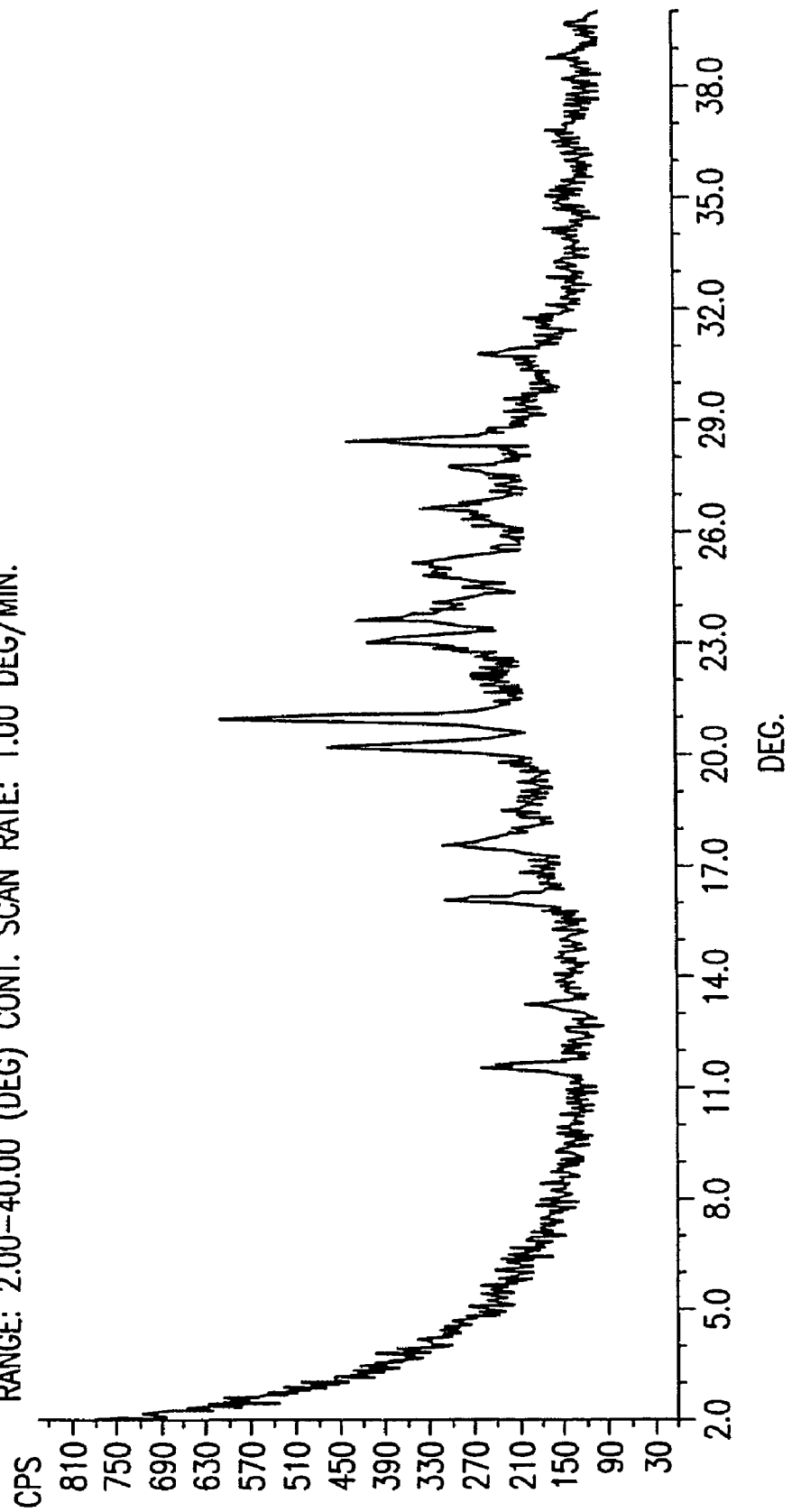
FIG. 5 is the powder X-ray diffractogram of (1S,5S)-3-(5,6-dichloro-3-pyridinyl)-3,6-diazabicyclo[3.2.0]heptane hydrochloride.

(1S,5S)-3-(5,6-Dichloro-3-pyridinyl)-3,6-diazabicyclo[3.2.0]heptane hydrochloride can be identified by its powder X-ray diffraction pattern in accordance with the Brief Description of the Drawings (FIG. 5).

Figure 5A:
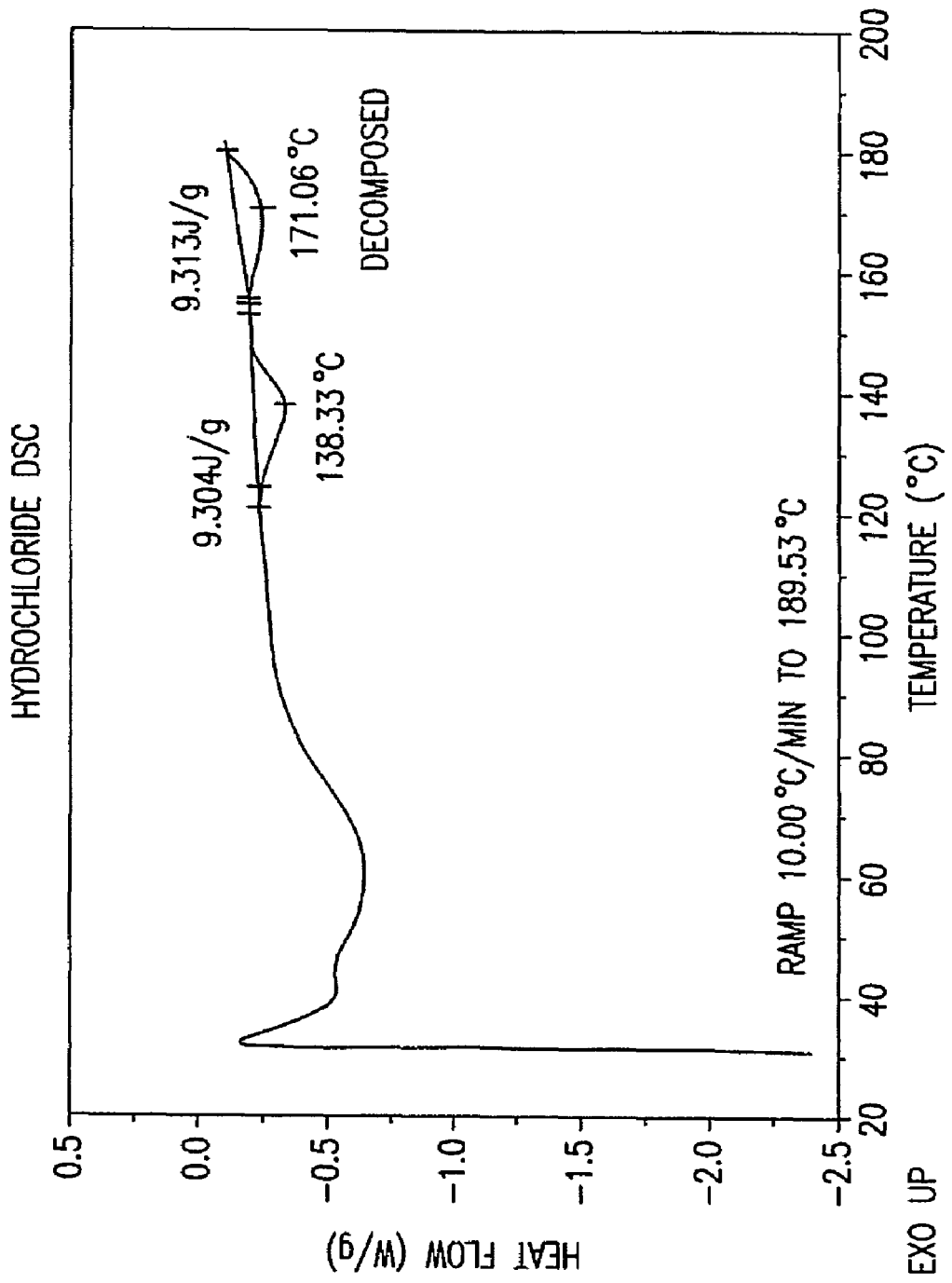
FIG. 5A is the differential scanning calorimetry thermogram of (1S,5S)-3-(5,6-dichloro-3-pyridinyl)-3,6-diazabicyclo[3.2.0]heptane hydrochloride.

Differential scanning calorimetry analysis of (1S,5S)-3-(5,6-dichloro-3-pyridinyl)-3,6-diazabicyclo[3.2.0]heptane hydrochloride provided melt/decomposition at 171.06° C. (FIG. 5A). The sample size was 4.1400 mg.

Figure 6:
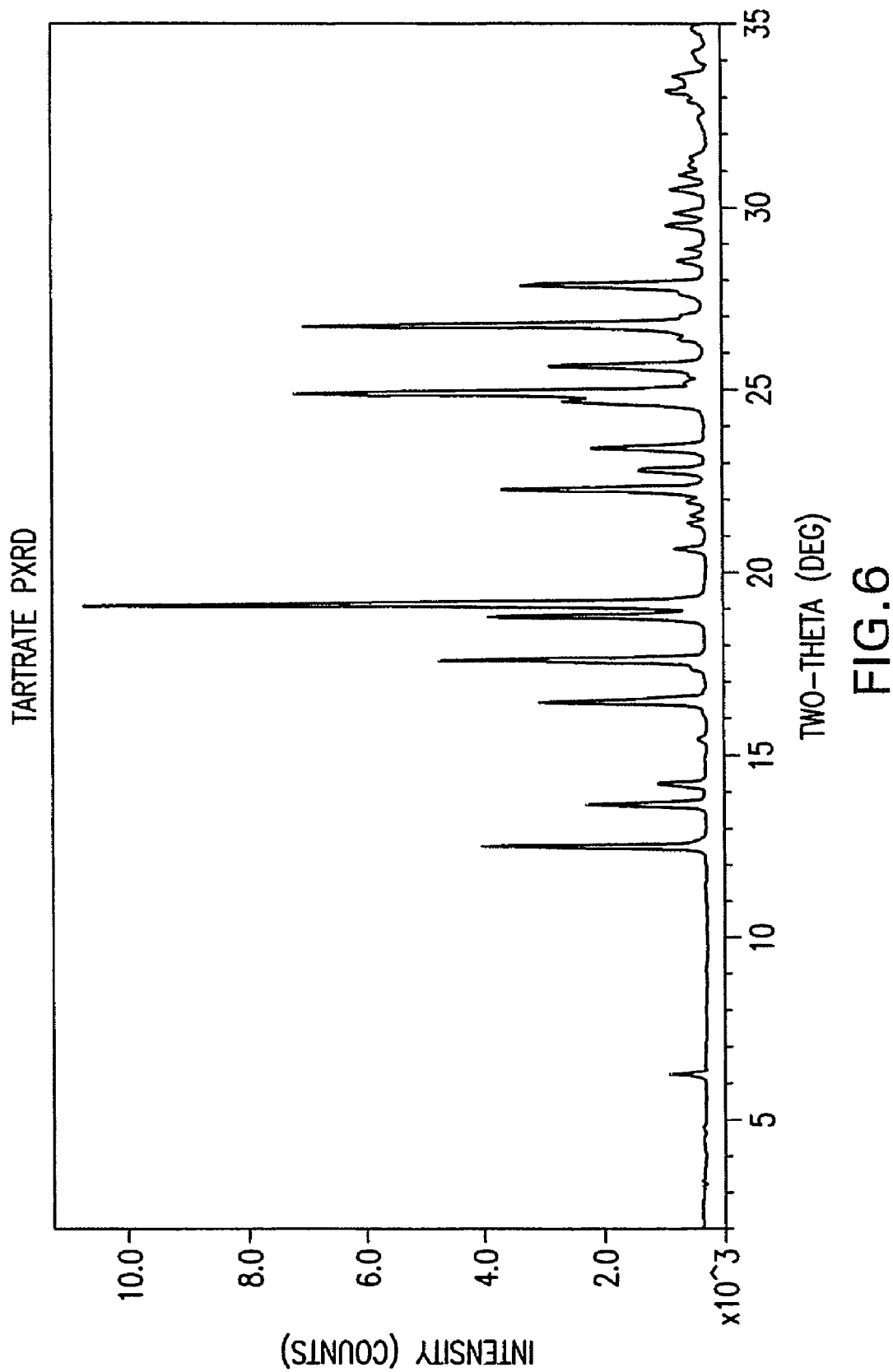
FIG. 6 is the powder X-ray diffractogram of (1S,5S)-3-(5,6-dichloro-3-pyridinyl)-3,6-diazabicyclo[3.2.0]heptane L-tartrate.

(1S,5S)-3-(5,6-Dichloro-3-pyridinyl)-3,6-diazabicyclo[3.2.0]heptane L-tartrate can be identified by its powder X-ray diffraction pattern in accordance with the Brief Description of the Drawings (FIG. 6). Characteristic two-theta angles of the powder X-ray diffraction pattern for the tartrate salt were 6.4, 12.6, 13.8, 14.3, 16.5, 17.7, 18.9, 19.2, 22.3, 22.9, 23.5, and 25.0.

Figure 6A:
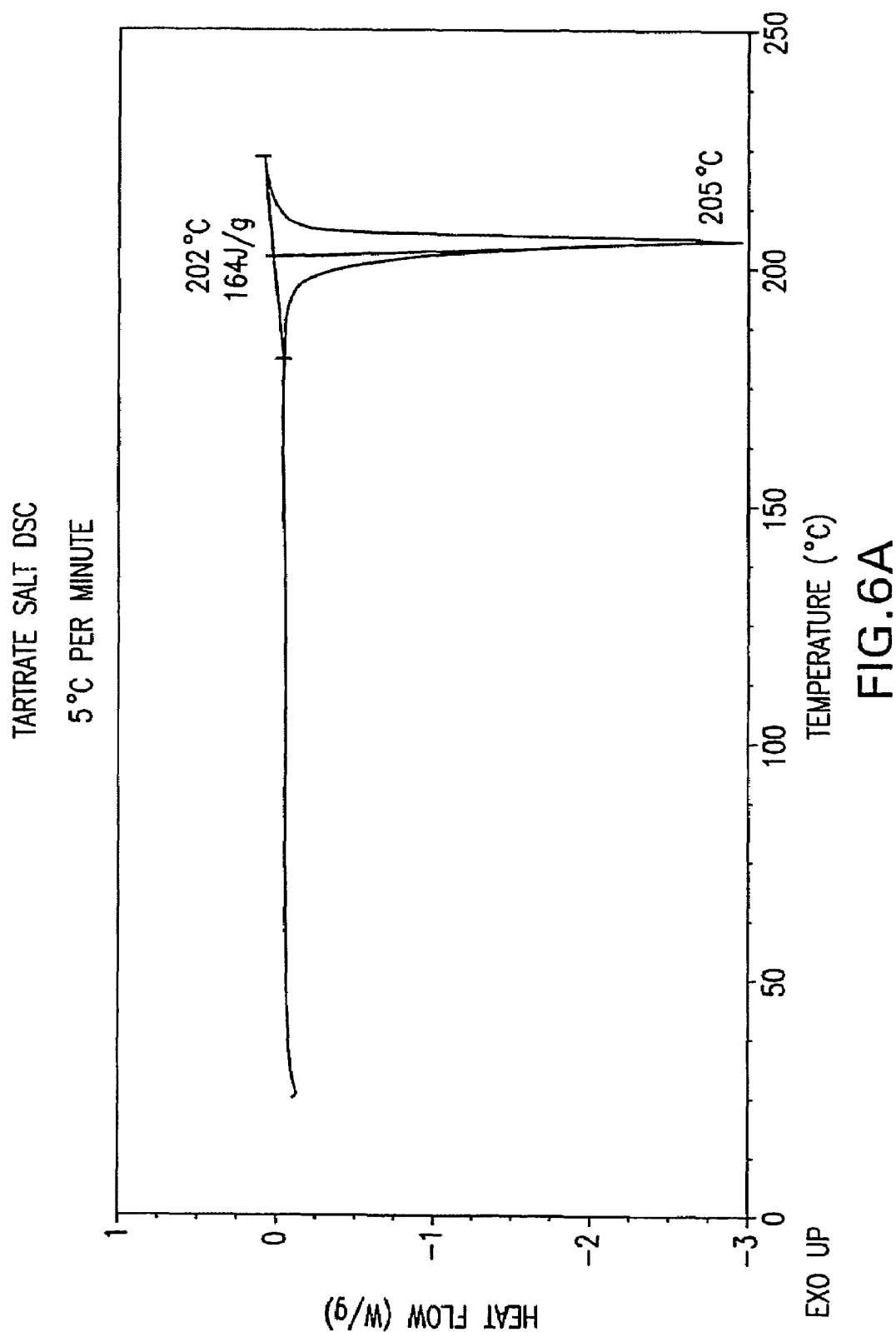
FIG. 6A is the differential scanning calorimetry thermogram of (1S,5S)-3-(5,6-dichloro-3-pyridinyl)-3,6-diazabicyclo[3.2.0]heptane L-tartrate.

Differential scanning calorimetry analysis of (1S,5S)-3-(5,6-dichloro-3-pyridinyl)-3,6-diazabicyclo[3.2.0]heptane L-tartrate provided melt/decomposition at 205° C. (FIG. 6A). The sample size was 1.640 mg.

(1S,5S)-3-(5,6-Dichloro-3-pyridinyl)-3,6-diazabicyclo[3.2.0]heptane L-tartrate monohydrate can be identified by its powder X-ray diffraction pattern in accordance with the Brief Description of the Drawings (FIG. 6B). Characteristic two-theta angles of the powder X-ray diffraction pattern for the L-tartrate monohydrate salt were 11.19, 12.30, 14.64, 16.81, 17.00, 18.46, 18.58, 23.07, 23.86, 24.75, 25.66, and 25.66. The crystallographic unit cell parameters of a single L-tartrate monohydrate crystal have been determined as having the following parameters: a is 31.652(4) Å; b is 7.3876(9) Å; c is 7.6254(9) Å; and β is 91.593(2)°. To afford a cell volume of 1782.4(3) Å$^3$, wherein a, b, and c are each a representative length of the crystal lattice and P is the unique angle. The salt crystallizes in the C2 space group.

Differential scanning calorimetry analysis of (1S,5S)-3-(5,6-dichloro-3-pyridinyl)-3,6-diazabicyclo[3.2.0]heptane L-tartrate monohydrate provided melt/decomposition at 215° C. (FIG. 6C). The sample size was 3.220 mg.

Figure 7:
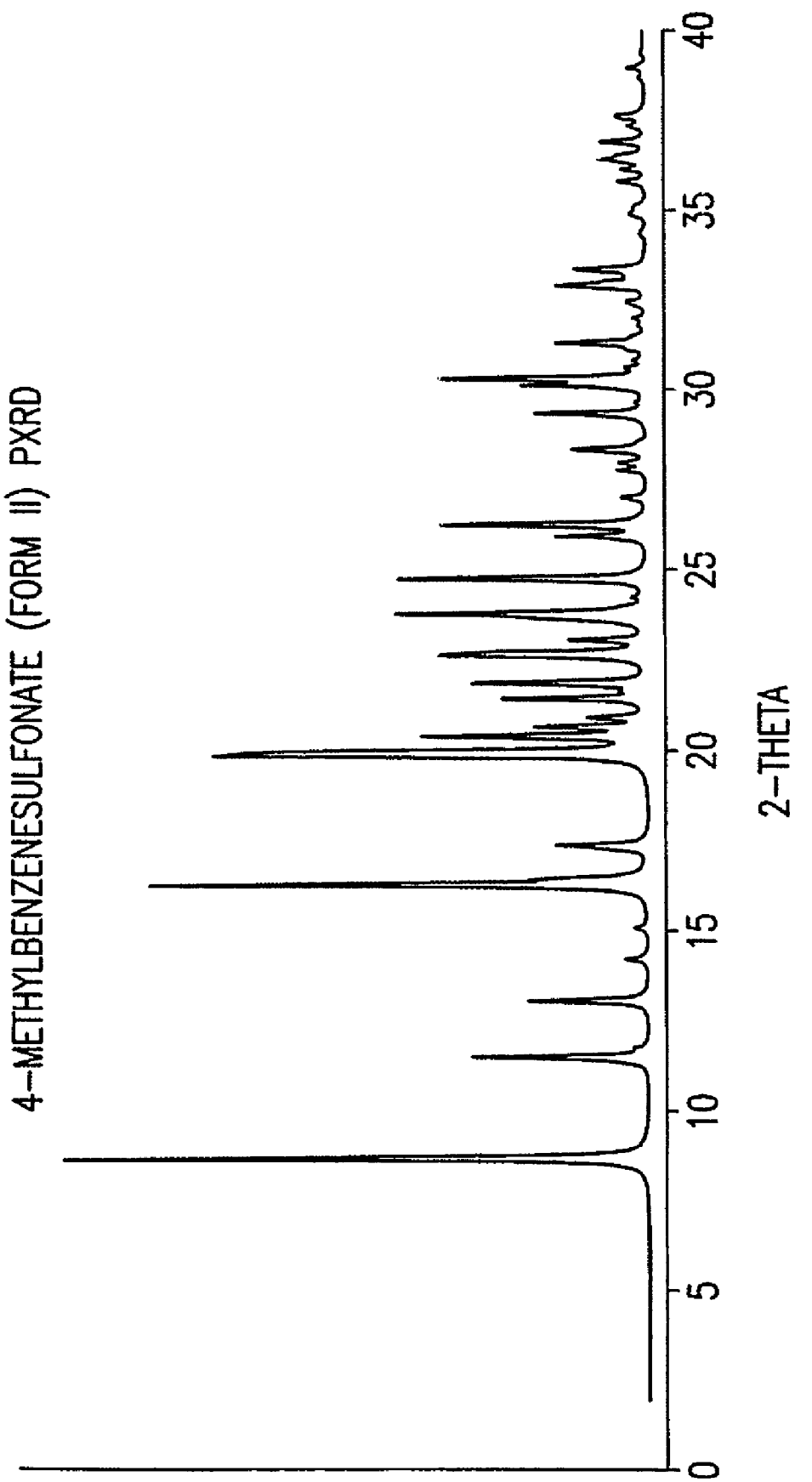
FIG. 7 is the powder X-ray diffractogram of (1S,5S)-3-(5,6-dichloro-3-pyridinyl)-3,6-diazabicyclo[3.2.0]heptane 4-methylbenzenesulfonate (Form II).

(1S,5S)-3-(5,6-Dichloro-3-pyridinyl)-3,6-diazabicyclo[3.2.0]heptane 4-methylbenzenesulfonate (Form II) is solid that can be identified by its powder X-ray diffraction pattern in accordance with the Brief Description of the Drawings (FIG. 7). Characteristic two-theta angles of the powder X-ray diffraction pattern for the 4-methylbenzenesulfonate (Form II) salt were 8.66, 11.48, 13.06, 16.28, 19.87, 19.97, 20.39, 21.89, 23.81, 24.79, 26.30, and 30.34. The crystallographic unit cell parameters of a single 4-methylbenzenesulfonate (Form II) crystal have been determined as having the following parameters: a is 9.063(1) Å; b is 13.622(2) Å; and c is 15.410(2) Å. To afford a cell volume of 1902.3(3) Å$^3$, wherein a, b, and c are each a representative length of the crystal lattice. The salt crystallizes in the P2$_1$2$_1$2$_1$ space group.

Figure 7A:
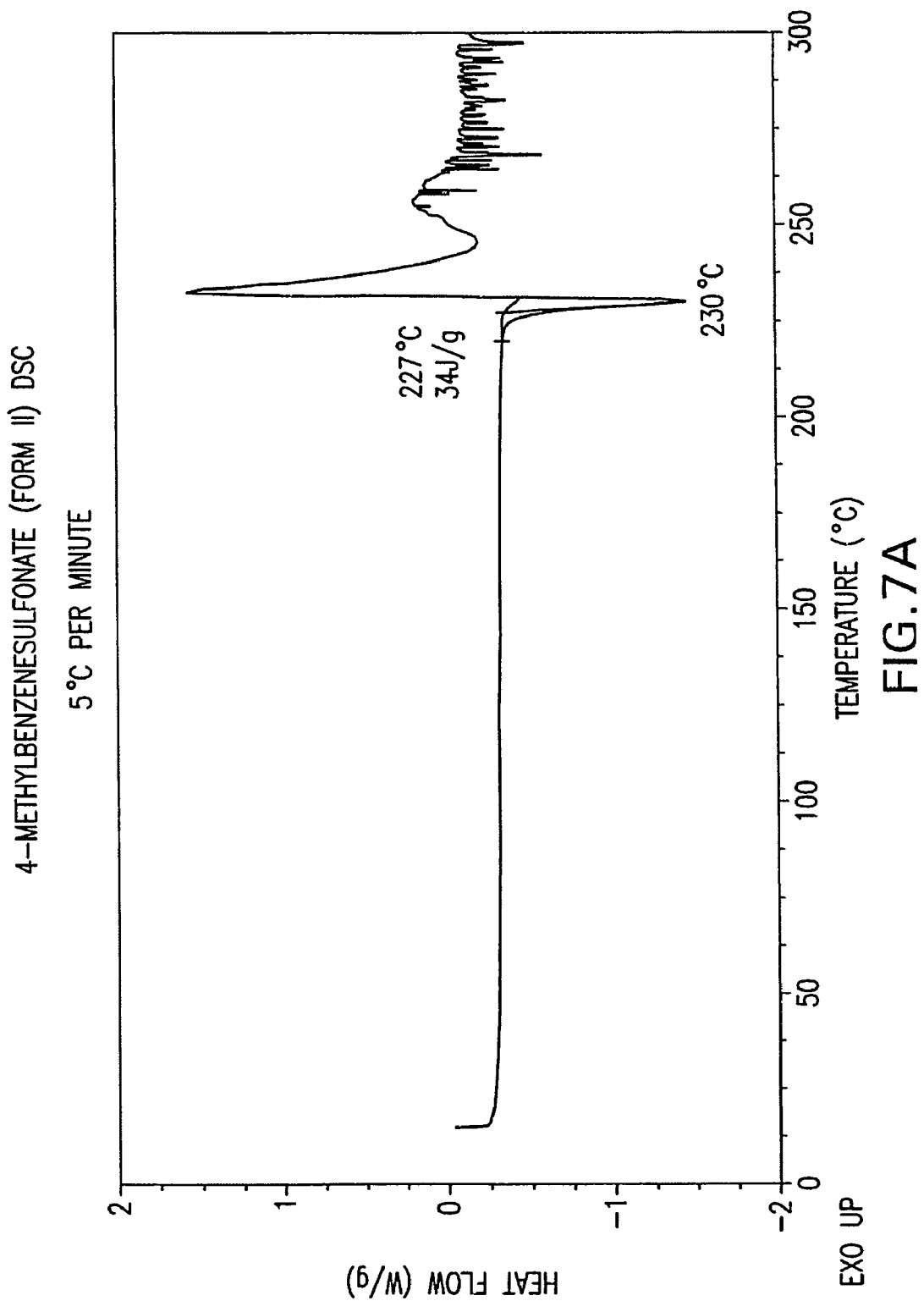
FIG. 7A is the differential scanning calorimetry thermogram of (1S,5S)-3-(5,6-dichloro-3-pyridinyl)-3,6-diazabicyclo[3.2.0]heptane 4-methylbenzenesulfonate (Form II).

Differential scanning calorimetry analysis of (1S,5S)-3-(5,6-dichloro-3-pyridinyl)-3,6-diazabicyclo[3.2.0]heptane 4-methylbenzenesulfonate (Form II) provided melt/decomposition at 230° C. (FIG. 7A). The sample size was 1.310 mg.

(1S,5S)-3-(5,6-Dichloro-3-pyridinyl)-3,6-diazabicyclo[3.2.0]heptane 4-methylbenzenesulfonate (Form I) is solid that can be identified by its powder X-ray diffraction pattern in accordance with the Brief Description of the Drawings (FIG. 7B). Characteristic two-theta angles of the powder X-ray diffraction pattern for the 4-methylbenzenesulfonate (Form I) salt were 8.80, 11.77, 13.75, 15.12, 17.23, 18.47, 20.60, 21.82, 22.97, 24.73, 26.46, 26.60, and 27.42. The crystallographic unit cell parameters of a single 4-methylbenzenesulfonate (Form I) crystal have been determined as having the following parameters: a is 8.422(7) Å; b is 12.49(1) Å; and c is 16.99(1) Å. To afford a cell volume of 1788(2) Å$^3$, wherein a, b, and c are each a representative length of the crystal lattice. The salt crystallizes in the P2$_1$2$_1$2$_1$ space group.

(1S,5S)-3-(5,6-Dichloro-3-pyridinyl)-3,6-diazabicyclo[3.2.0]heptane sulfate monohydrate can be identified by its powder X-ray diffraction pattern in accordance with the Brief Description of the Drawings (FIG. 8). Characteristic two-theta angles of the powder X-ray diffraction pattern for the sulfate salt were 5.35, 13.39, 14.18, 15.40, 16.97, 19.15, 21.04, 22.39, 22.66, 23.01, 23.51, and 24.68. The crystallographic unit cell parameters of a single sulfate salt crystal have been determined as having the following parameters: a is 5.6009(6) Å; b is 33.017(4) Å; c is 6.7495(8) Å; and β is 91.419(2)°. To afford a cell volume of 1247.8(2) Å$^3$, wherein a, b, and c are each a representative length of the crystal lattice and β is the unique angle. The salt crystallizes in the P2$_1$ space group.

Figure 8A:
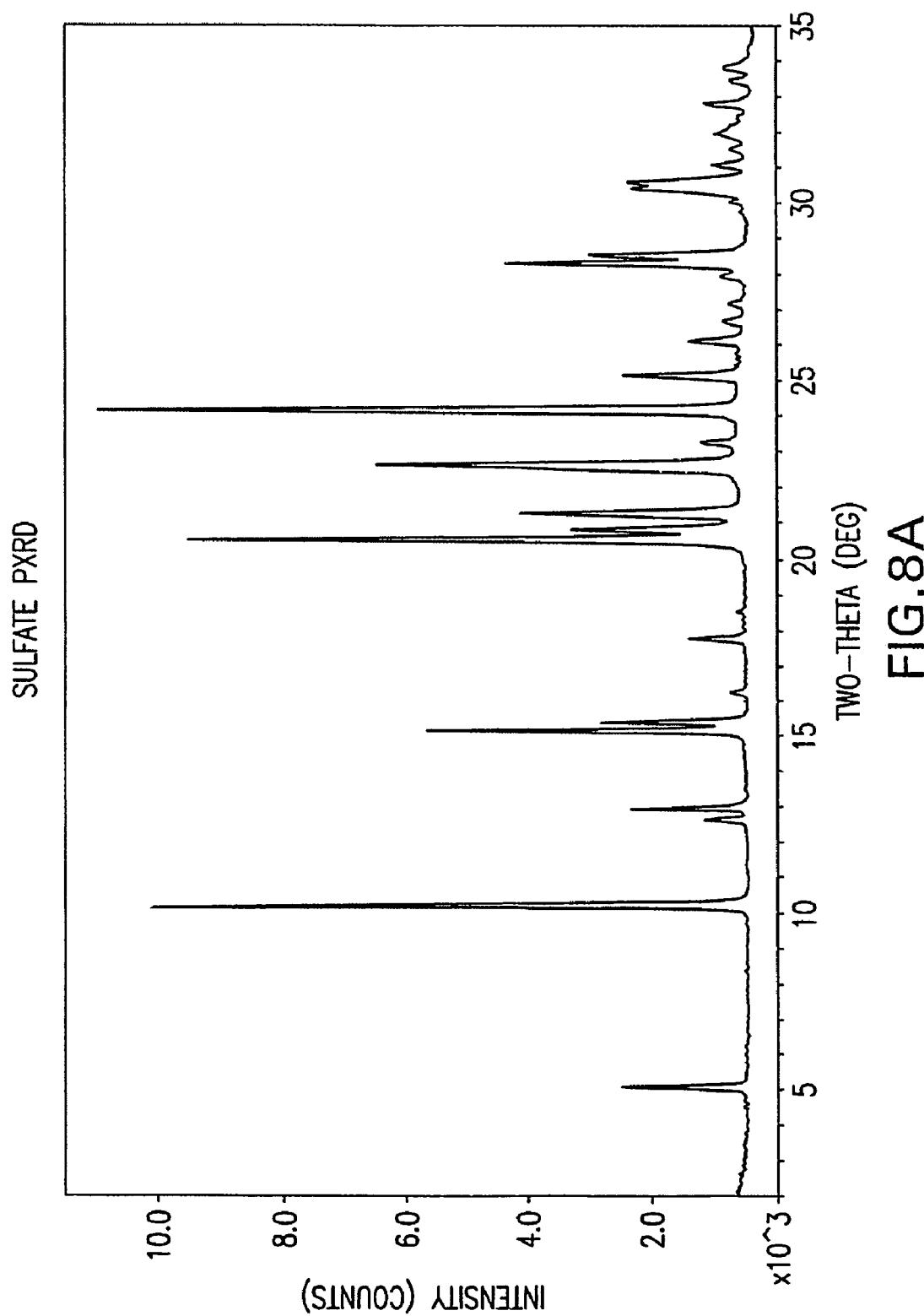
FIG. 8A is the powder X-ray diffractogram of (1S,5S)-3-(5,6-dichloro-3-pyridinyl)-3,6-diazabicyclo[3.2.0]heptane sulfate.

(1S,5S)-3-(5,6-Dichloro-3-pyridinyl)-3,6-diazabicyclo[3.2.0]heptane sulfate can be identified by its powder X-ray diffraction pattern in accordance with the Brief Description of the Drawings (FIG. 8A).

Figure 8B:
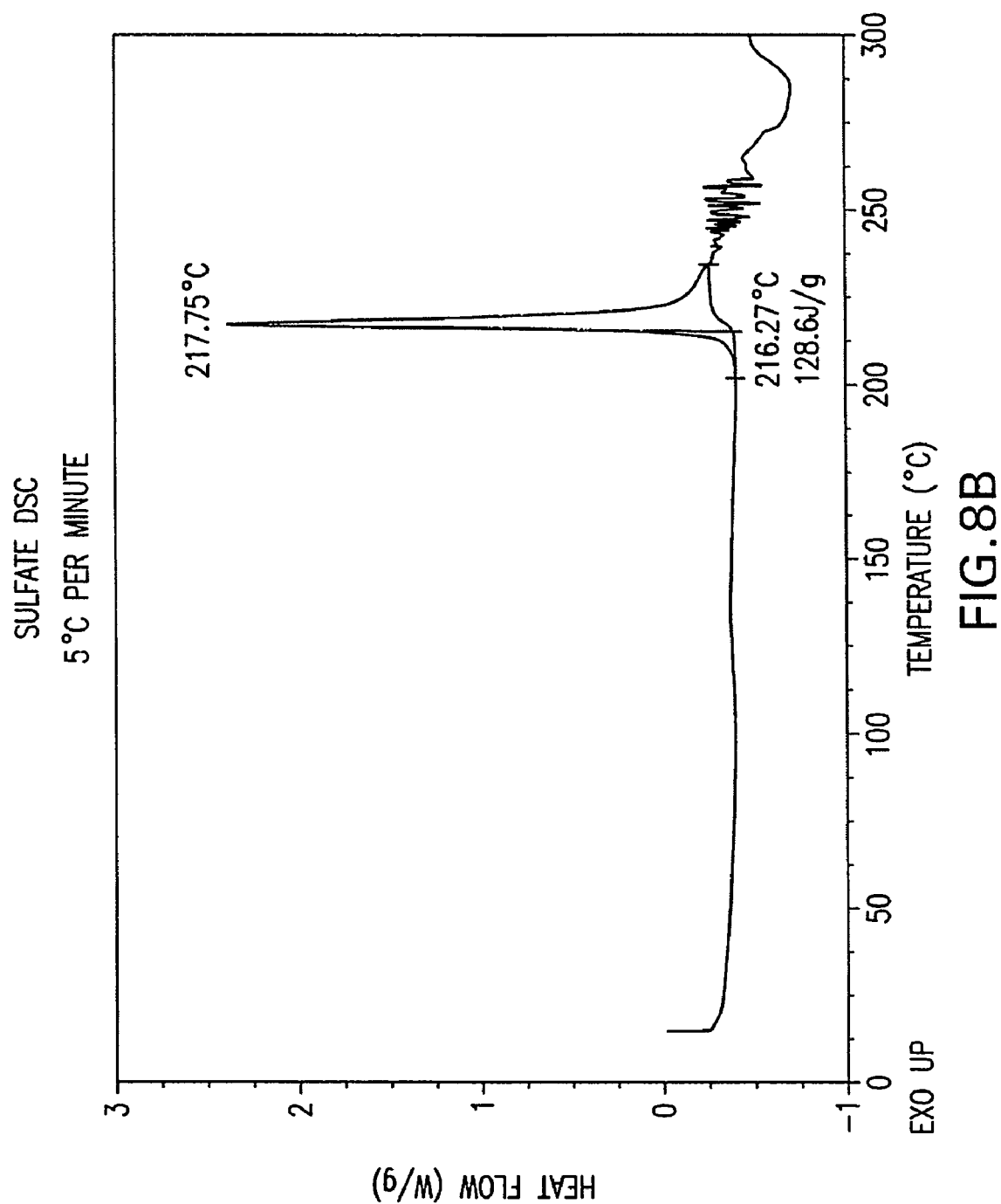
FIG. 8B is the differential scanning calorimetry thermogram of (1S,5S)-3-(5,6-dichloro-3-pyridinyl)-3,6-diazabicyclo[3.2.0]heptane sulfate.

Differential scanning calorimetry analysis of (1S,5S)-3-(5,6-dichloro-3-pyridinyl)-3,6-diazabicyclo[3.2.0]heptane sulfate provided melt/decomposition at 215.27° C. (FIG. 8B). The sample size was 1.190 mg.

(1S,5S)-3-(5,6-Dichloro-3-pyridinyl)-3,6-diazabicyclo[3.2.0]heptane can be identified by its powder X-ray diffraction pattern in accordance with the Brief Description of the Drawings (FIG. 9). Characteristic two-theta angles of the powder X-ray diffraction pattern for (1S,5S)-3-(5,6-dichloro-3-pyridinyl)-3,6-diazabicyclo[3.2.0]heptane were 13.43, 18.42, 19.22, 20.06, 21.81, 23.06, 24.37, 24.89, 26.48, 27.30, 27.67, and 32.44. The crystallographic unit cell parameters of a single (1S,5S)-3-(5,6-dichloro-3-pyridinyl)-3,6-diazabicyclo[3.2.0]heptane crystal have been determined as having the following parameters: a is 8.080(3) Å; b is 11.159(4) Å; and c is 11.903(4) Å. To afford a cell volume of 1073.3(6) Å$^3$, wherein a, b, and c are each a representative length of the crystal lattice. The compound crystallizes in the P2$_1$2$_1$2$_1$ space group.

Figure 9A:
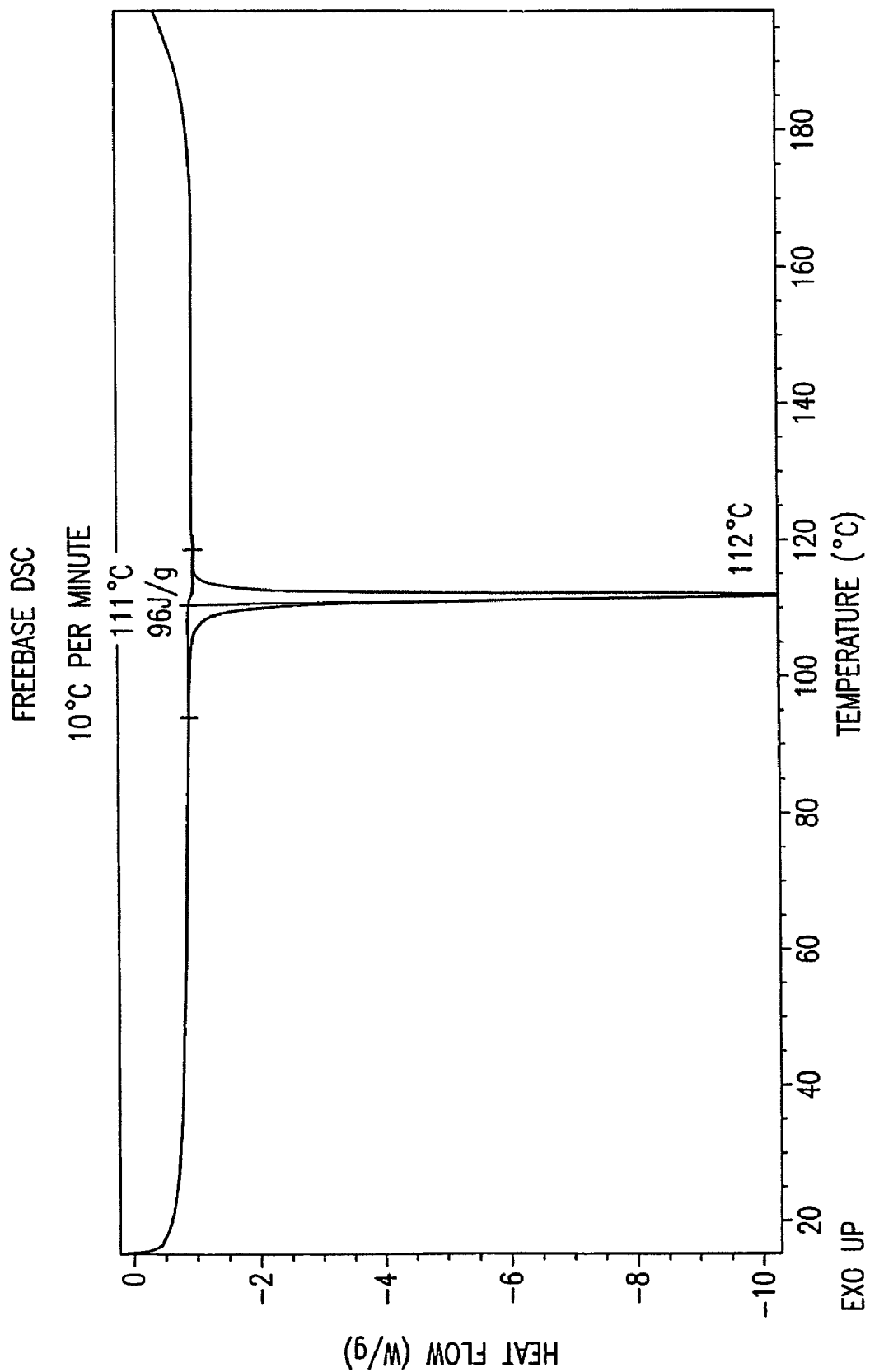
FIG. 9A is the differential scanning calorimetry thermogram of (1S,5S)-3-(5,6-dichloro-3-pyridinyl)-3,6-diazabicyclo[3.2.0]heptane.

Differential scanning calorimetry analysis of (1S,5S)-3-(5,6-dichloro-3-pyridinyl)-3,6-diazabicyclo[3.2.0]heptane provided melt/decomposition at 112° C. (FIG. 9A). The sample size was 1.080 mg.

As used herein, the term "substantially pure", when used in reference to a (1S,5S)-3-(5,6-dichloro-3-pyridinyl)-3,6-diazabicyclo[3.2.0]heptane salt, refers to that salt which is greater than about 90% pure. The crystalline form of (1S,5S)-3-(5,6-dichloro-3-pyridinyl)-3,6-diazabicyclo[3.2.0]heptane does not contain more than about 10% of any other compound and, in particular, does not contain more than about 10% of any other form of (1S,5S)-3-(5,6-dichloro-3-pyridinyl)-3,6-diazabicyclo[3.2.0]heptane, such as amorphous, solvated forms, non-solvated forms, and desolvated forms. More preferably, the term "substantially pure" refers to a (1S,5S)-3-(5,6-dichloro-3-pyridinyl)-3,6-diazabicyclo[3.2.0]heptane salt which is greater than about 95% pure. In such form, the (1S,5S)-3-(5,6-dichloro-3-pyridinyl)-3,6-diazabicyclo[3.2.0]heptane salt does not contain more than about 5% of any other compound and, in particular, any other form of (1S,5S)-3-(5,6-dichloro-3-pyridinyl)-3,6-diazabicyclo[3.2.0]heptane, such as amorphous, solvated forms, non-solvated forms, and desolvated forms. Even more preferably, the term "substantially pure" refers to a (1S,5S)-3-(5,6-dichloro-3-pyridinyl)-3,6-diazabicyclo[3.2.0]heptane salt which is greater than about 97% pure. In such salt, the (1S,5S)-3-(5,6-dichloro-3-pyridinyl)-3,6-diazabicyclo[3.2.0]heptane salt contains no more than 3% of any other compound and, in particular, does not contain more than 3% of any other form of (1S,5S)-3-(5,6-dichloro-3-pyridinyl)-3,6-diazabicyclo[3.2.0]heptane, such as amorphous, solvated forms, non-solvated forms, and desolvated forms.

Yet even more preferably, the term "substantially pure" refers to a (1S,5S)-3-(5,6-dichloro-3-pyridinyl)-3,6-diazabicyclo[3.2.0]heptane salt which is greater than about 99% pure. The (1S,5S)-3-(5,6-dichloro-3-pyridinyl)-3,6-diazabicyclo[3.2.0]heptane salt contains no more than about 1% of any other compound and, in particular, any other form of (1S,5S)-3-(5,6-dichloro-3-pyridinyl)-3,6-diazabicyclo[3.2.0]heptane, such as amorphous, solvated forms, non-solvated forms, and desolvated forms.

Powder X-ray diffraction (PXRD) analysis of samples was conducted in the following manner. Samples for X-ray diffraction analysis were prepared by spreading the sample powder (ground to a fine powder with mortar and pestle, or with glass microscope slides for limited quantity samples) in a thin layer on the sample holder and gently flattening the sample with a microscope slide. Diffraction patterns were collected using an Inel G3000 diffractometer equipped with an incident beam germanium monochromator to provide Cu—$K_{\alpha_1}$ radiation. The X-ray generator was operated at a voltage of 40 kV and a current of 30 mA. The Inel G3000 is equipped with a position sensitive detector that monitors all diffraction data simultaneously. The detector was calibrated by collecting the attenuated direct beam for seven seconds in 1 degree intervals across a 90 degree two theta range. The calibration was checked against a silicon line position reference standard (NIST 640c). Samples were placed on an aluminum sample holder and leveled with a glass slide.

Samples were run in one of three configurations: circular bulk holder, a quartz zero background plate or hot stage mount (similar mounting to a zero background plate). Alternatively, X-ray powder diffraction can be performed using a Rigaku Miniflex diffractometer (30 kV and 15 mA; X-ray source: Cu; Range: 2.00-40.00° Two Theta; Scan Rate: 5 degree/minute) or a Scintag ×1 or ×2 diffractometer (2 kW normal focus X-ray tube with either a liquid nitrogen or Peltier cooled germanium solid state detector; 45 kV and 40 mA; X-ray source: Cu; Range: 2.00-40.00° Two Theta; Scan Rate: 1 degree/minute).

Characteristic powder X-ray diffraction pattern peak positions are reported for salts in terms of angular positions (two theta) with an allowable variability of ±0.2°. The allowable variability is specified in the U.S. Pharmacopeia, pages 1843-1844 (1995). The variability of ±0.2° is intended to be used when comparing two powder X-ray diffraction patterns. In practice, if a diffraction pattern peak from one pattern is assigned a range of angular positions (two theta) which is the measured peak position ±0.2° and a diffraction pattern peak from another pattern is assigned a range of angular positions (two theta) which is the measured peak position ±0.1° and if those ranges of peak positions overlap, then the two peaks are considered to have the same angular position (two theta). For example, if a diffraction pattern peak from one pattern is determined to have a peak position of 5.20°, for comparison purposes the allowable variability allows the peak to be assigned a position in the range of 5.00°-5.40°. If a comparison peak from the other diffraction pattern is determined to have a peak position of assigned a position in the range of 5.15°-5.55°. Because there is overlap between the two ranges of peak positions (i.e., 5.00°-5.40° and 5.15°-5.55°) the two peaks being compared are considered to have the same angular position (two theta).

Single Crystal X-ray diffraction analysis of samples was conducted in the following manner. Samples for X-ray diffraction analysis were prepared by affixing selected single crystals to glass pins with epoxy adhesive. X-ray diffraction data was collected using a Bruker SMART system with an APEX area detector (50 kV and 40 mA; X-ray source: Mo). Data were collected at −90° C.

It is understood that (1S,5S)-3-(5,6-dichloropyridin-3-yl)-3,6-diazabicyclo[3.2.0]heptane and salts thereof can be identified by characteristic peaks in their powder X-ray diffraction pattern. One with skill in the art in analytical chemistry would be able to readily identify (1S,5S)-3-(5,6-dichloropyridin-3-yl)-3,6-diazabicyclo[3.2.0]heptane or a salt of (1S,5S)-3-(5,6-dichloropyridin-3-yl)-3,6-diazabicyclo[3.2.0]heptane by as few as one characteristic peak in the powder X-ray diffraction pattern.

Differential scanning calorimetric (DSC) analysis of samples was conducted in the following manner. A.T.A. Instruments Model Q1000 differential scanning calorimeter with a Mettler 821 DSC cell using standard software to identify the onset of the melt. The analysis parameters were: sample weight 1-3 mg, placed in an aluminum pan, and sealed after a pin hole was poked in the lid; heating rate: 10° C./minute).

One method for preparing (1S,5S)-3-(5,6-dichloro-3-pyridinyl)-3,6-diazabicyclo[3.2.0]heptane is shown below in Scheme 1.

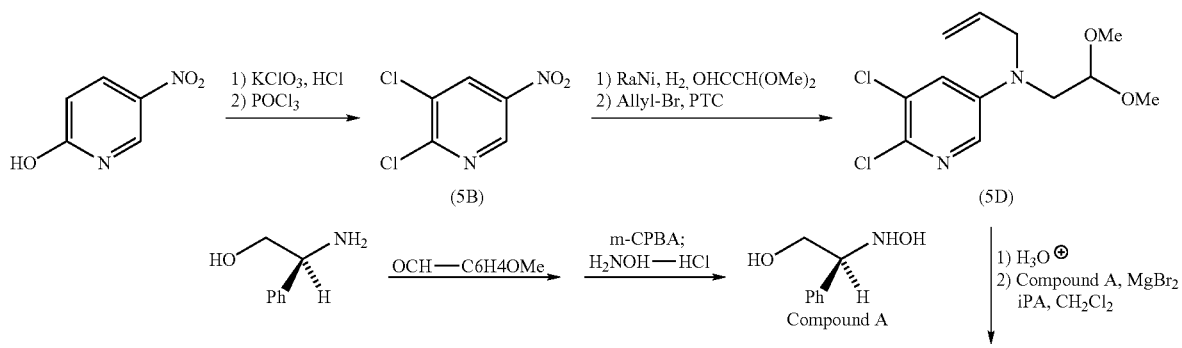

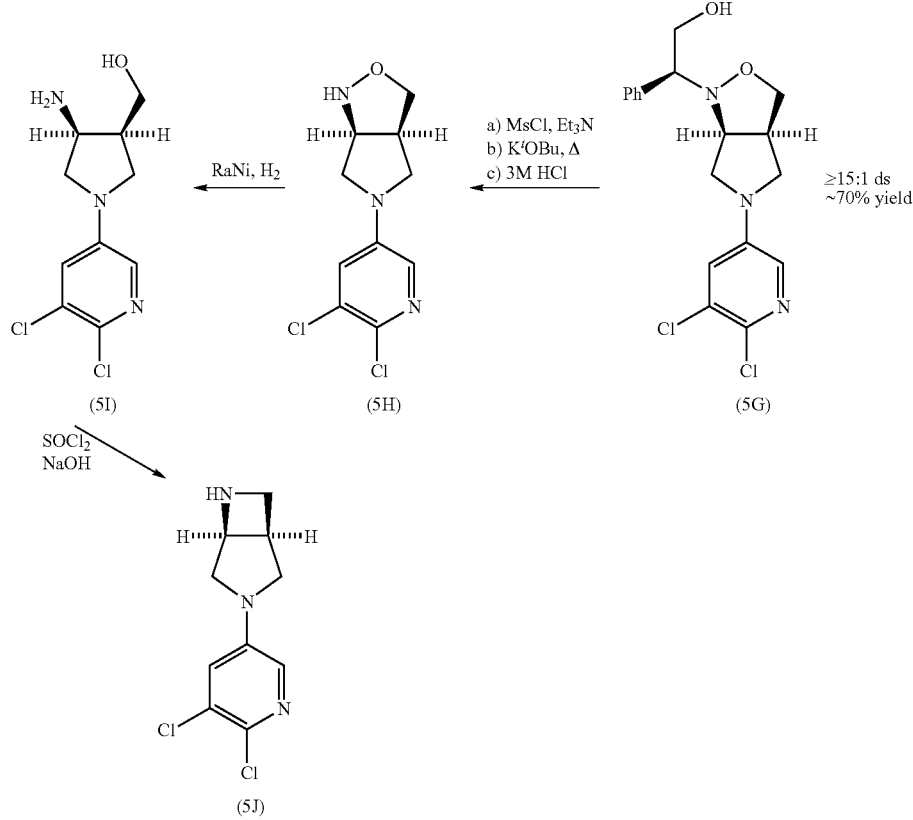

As shown in Scheme 1, the sequential treatment of 2-hydroxy-5-nitropyridine with potassium chlorate under heated conditions provides 3-chloro-2-hydroxy-5-nitropyridine which when further treated with phosphorous oxychloride under heated conditions provides 2,3-dichloro-5-nitropyridine. The nitro containing compound when treated to the reductive conditions of Raney-nickel and 40 PSI of hydrogen provides the amine which when further treated with glyoxal-1,2-dimethyl acetal in the presence of Raney-nickel under heated condition provides (5,6-dichloro-pyridin-3-yl)-(2,2-dimethoxy-ethyl)-amine. The amine when treated with allyl bromide and methyl tributyl ammonium chloride in a mixture of methyl tert-butyl ether and 50% aqueous sodium hydroxide provides allyl-(5,6-dichloro-pyridin-3-yl)-(2,2-dimethoxy-ethyl)amine (Compound 5D).

The synthesis of compound of formula A wherein the phenyl group may be optionally substituted with groups such as alkyl, alkoxy or halo may be achieved according to the following pathway. (S)-phenylglycinol (or a substituted version) when treated with p-anisaldehyde in methyl tert-butyl ether under reflux condition under a Dean-Stark trap followed by cooling to 0° C., diluting with a solvent such as tetrahydrofuran and treating with m-chloroperoxybenzoic acid and hydroxylamine provides compounds of formula A.

The treatment of Compound 5D with an acid such as hydrochloric acid under cooling conditions provides (allyl-5,6-dichloro-pyridin-3-yl)-amino)-acetaldehyde which when treated with 2-(S)-hydroxyamino-2-phenyl-ethanol and magnesium bromide in a solvent such as isopropyl alcohol provides (3S,4S)-2-[5-(5,6-dichloro-pyridin-3-yl)-hexahydropyrrolo[3,4-c]isoxazol-1-yl]-2-(2'S)-phenyl-ethanol (Compound 5G). Compound 5G when treated with methanesulfonyl chloride to generate the mesylate which is then treated with sodium tert-butoxide followed by an acidic workup provides (3S,4S)-5-(5,6-dichloro-pyridin-3-yl)-hexahydro-pyrrolo[3,4-c]isoxazole (Compound 5H). The treatment of Compound 5H with Raney-nickel and 40 PSI of hydrogen in a mixture of tetrahydrofuran, ethanol and water provides (3S,4S)-[4-amino-1-(5,6-dichloro-pyridin-3-yl)-pyrrolidin-3-yl]-methanol (Compound 5I). The treatment of Compound 5I with thionyl chloride and N-methylpyrrolidinone under heated conditions in 1,2-dimethoxyethane followed by treatment with sodium hydroxide or another similar base provides (1S,5S)-3-(5,6-dichloropyridin-3-yl)-3,6-diaza-bicyclo[3.2.0]heptane (Compound 5J).

Hydroxyl groups described in the processes may be converted into a leaving group when necessary during the synthesis of other described compounds or as needed according to one skilled in the art to assist conversion into another functional group. Some of the methods contemplated include but are not limited to the treatment of alcohols with reagents such as methane sulfonyl chloride, trifluoromethane sulfonyl chloride, p-toluenesulfonyl chloride, thionyl chloride, methane sulfonyl anhydride, trifluoromethane sulfonyl anhydride. These transformation may be carried out in the presence of a base in a solvent such as but not limited to tetrahydrofuran or dichloromethane. Typical bases useful for these transformation include but are not limited to triethylamine, N-methylmorpholine, ethyl diisopropylamine and those known to one skilled in the art.

An alternative process for preparing (1S,5S)-3-(5,6-dichloro-3-pyridinyl)-3,6-diazabicyclo[3.2.0]heptane is described in the Examples below. The Examples are intended as a illustration of the compounds and methods of the invention and are not intended to limit the scope of the invention, which is defined by the appended claims.

EXAMPLES

Preparation of (1S,5S)-3-(5,6-Dichloro-3-pyridinyl)-3,6-diazabicyclo[3.2.0]heptane Example 1 tert-Butyl (1R,5S)-3,6-diazabicyclo[3.2.0]heptane-6-carboxylate

Example 1A

Benzyl 2,2-dimethoxyethylcarbamate

Benzyl chloroformate (231.3 g, 1.3 mol) was added gradually to a mixture of aminoacetaldehyde dimethyl acetal (152.0 g, 1.3 mol) in toluene (750 mL) and aqueous NaOH (72.8 g, 1.82 mol; in 375 mL of water) at 10-20° C. After the addition was completed, the mixture was stirred at ambient temperature about 4 hours. The organic layer was separated, washed with brine (2×100 mL) and concentrated to provide the title compound. $^1$H NMR (CDCl$_3$, 300 MHz) δ 3.33 (t, J=6.0 Hz, 2H), 3.39 (s, 6H), 4.37 (t, J=6.0 Hz, 1H), 5.11 (s, 2H), 7.30 (m, 5H); MS (DCI/NH$_3$) m/z 257 (M+NH$_4$)$^+$, 240 (M+H)$^+$.

Example 1B

Benzyl allyl(2,2-dimethoxyethyl)carbamate

The product of Example 1A (281.0 g, 1.18 mol) in dry toluene (1.0 L) was treated with powdered KOH (291.2 g, 5.20 mol) and triethylbenzylammonium chloride (4.4 g, 0.02 mol). A solution of allyl bromide (188.7 g, 1.56 mol) in toluene (300 mL) was then added dropwise over 1 hour at 20-30° C. The mixture was stirred overnight at room temperature and then water (300 mL) was added over 20 minutes at 20-30° C. The layers were separated and the aqueous phase was extracted with toluene (2×300 mL). The organic phases were combined, washed with brine (2×100 mL), dried (K$_2$CO$_3$), filtered and the filtrate concentrated to provide the title compound. $^1$H NMR (MeOH-d$_4$, 300 MHz) δ 3.32 (s, 3H) 3.37 (m, 5H), 3.97 (d, J=5.4 Hz, 2H), 4.40-4.50 (m, 1H), 5.15 (m, 4H), 5.75 (m, 1H), 7.23 (m, 5H); MS (DCI/NH$_3$) m/z 297 (M+NH$_4$)$^+$, 280 (M+H)$^+$.

Example 1C

Benzyl allyl(2-oxoethyl)carbamate

The product of Example 1B (314.0 g, 1.125 mol) was treated with formic acid (88%, 350 mL) at room temperature and allowed to stir for 15 hours. Most of the formic acid was removed by concentration under reduced pressure at 40-50° C. The residue was extracted with ethyl acetate (3×500 mL). The extracts were combined and washed with brine until the wash had a pH=6-7. The organic phase was concentrated to provide the title compound. $^1$H NMR (CDCl$_3$, 300 MHz) δ 3.20 (m, 1H), 3.97 (m, 2H), 4.10 (m, 1H), 5.10 (m, 4H), 5.75 (m, 1H), 7.45 (m, 5H), 9.50 (d, J=6.4 Hz, 1H); MS (DCI/NH$_3$) m/z 234 (M+H)$^+$.

Example 1D

Benzyl allyl[2-(hydroxyimino)ethyl]carbamate

The product of Example 1C (260 g, 1.115 mol) in acetonitrile (1.5 L) was treated with sodium acetate trihydrate (170.6 g, 4.41 mol) in distilled water (750 mL) and NH$_2$OH hydrochloride (98.0 g, 4.41 mol) under N$_2$. The mixture was stirred at room temperature for about 20 hours. The volatiles were removed under reduced pressure and the residue was extracted with ethyl acetate (2×750 mL). The combined organic phases were washed with brine until the wash had a pH=7. The organic phase was concentrated to provide the title compound. $^1$H NMR (MeOH-d$_4$, 300 MHz) δ 3.94 (m, 2H), 3.98 (d, J=5.5 Hz, 1H), 4.17 (d, J=4.4 Hz, 1H), 5.30 (m, 4H), 5.60 (m, 1H), 7.40 (m, 5H). MS (DCI/NH$_3$) m/z 266M+NH$_4$)$^+$, 249 (M+H)$^+$.

Example 1E

Benzyl cis-3-amino-4-(hydroxymethyl)-1-pyrrolidinecarboxylate

A solution of the product of Example 1D (240 g, 0.97 mol) in xylene (1.0 L) was heated at reflux under N$_2$ for about 10 hours. The resulting brown solution was cooled to 10-15° C. and acetic acid (1.0 L) was added under N$_2$. Zinc powder (100 g, 1.54 mol) was added gradually, and the gray mixture was stirred at room temperature for 3 hours. The mixture was filtered and water (1.0 L) was added to the filtrate. The filtrate was stirred for 10 minutes and the organic layer was separated. The aqueous phase was washed well with xylenes (4×400 mL) and then concentrated under reduced pressure to a volume of approximately 200 mL. This residue was basified to pH 9-10 by addition of saturated aqueous Na$_2$CO$_3$. The precipitated white solid was removed by filtration and the filtrate was extracted with CHCl$_3$ (3×600 mL). The combined organic phases were washed with saturated Na$_2$CO$_3$ solution (2×50 mL) and dried over anhydrous Na$_2$CO$_3$. The mixture was filtered through a short column of diatomaceous earth and the filtrate was concentrated to provide the title compound. $^1$H NMR (MeOH-d$_4$, 300 MHz) δ 2.40 (m, 1H), 3.30 (m, 2H), 3.80-3.50 (m, 5H), 5.10 (s, 2H), 7.35 (m, 5H); MS (DCI/NH$_3$) m/z 251 (M+H)$^+$.

Alternatively, the product of Example 1B (75.3 Kg) in toluene solution (364.6 kg) was charged to a 200-gallon glass reactor, and the toluene was removed by distillation. The distillation, performed under vacuum and at an internal temperature of not more than 70° C., was judged to be complete when the toluene content was less than 40 wt %. The contents of the reactor were cooled to 23° C. and formic acid (172 Kg) was added, followed by water (15.1 Kg). The contents of the reactor were stirred at room temperature until there was less than 1% starting material remaining. The contents of the reactor were cooled to 5° C., and 50% NH$_2$OH aqueous solution (34.5 Kg) was charged slowly to the reactor over 45 min. The contents of the reactor were stirred at room temperature until there was less than 1 wt % intermediate 1C remaining. Water (292 Kg) was charged to the reactor, followed by addition of n-pentanol (148 Kg). The contents of the reactor were stirred for 15 min. The layers were separated and the bottom aqueous layer was extracted again with n-pentanol (148 kg). The n-pentanol layers containing intermediate 1D were combined and cooled to 5° C. The pH of the n-pentanol layer was adjusted to 8.5 with 25% NaOH solution (244 Kg), maintaining the internal temperature at not more than 35° C. The layers were separated, and the n-pentanol layer was washed with 25% NaCl solution (262 Kg). The organic layer was collected and vacuum distilled, at a temperature less than 85° C., to remove any remaining toluene carried over from step 2. More n-pentanol was added back as necessary, so that the final concentration of 4 was 20-30 wt %. Distillation was continued until the level of toluene was less than 2 wt % and the water content was less than 0.2 wt %. The solution assay yield of intermediate 1D was determined to be 63.5 Kg (97%). The intermediate 1D was not isolated, and the solution was charged to a 200-gallon glass-lined reactor, equipped with a mechanical agitator, condenser, temperature probe and nitrogen inlet and diluted with n-pentanol to give ~10% wt solution. The contents of the reactor was heated to NLT 133° C., target 135° C., for 13 hours. The reaction was cooled to room temperature and then transferred to tared poly-lined drums. The solution assay yield was determined to be 54.8 Kg (86%). Raney Nickel (6.2 Kg, 25 wt %), ethanol (50 Kg) and about half of this solution (298 Kg solution, 24.5 Kg by assay) were charged to a reactor. The internal temperature of the reactor was adjusted to 25±5° C. The reactor was then pressure purged with hydrogen 3 times. The solution was hydrogenated at NMT 60 psig, target 40 psig, for NLT 4 hours while maintaining an internal temperature of 25±15° C. Upon completion of the reaction the contents of the reactor were filtered through filter aid to remove the catalyst and the Step 6 product solution was collected in poly-lined drums. The total solution assay yield was determined to be 21.6 Kg (96%). The product 1E was not isolated, and was taken on to the next step as a solution.

Example 1F

Benzyl (4aS,7aS)-2,2-dimethylhexahydropyrrolo[3,4-d][1,3]oxazine-6(4H)-carboxylate (R)-mandelate The product of Example 1E (140 g, 0.56 mol) in dry acetone (150 mL) was treated with 2-methoxypropene (55 mL, 0.57 mol) at room temperature overnight. The reaction mixture was concentrated under reduced pressure and the residue was dissolved in dry acetone (750 mL). ®-Mandelic acid (85 g, 0.56 mol) was added and the solution was stirred at room temperature for 48 hours. The precipitate was isolated by filtration and dried under reduced pressure to provide the title compound as a solid. $^1$H NMR (MeOH-d$_4$, 300 MHz) δ 1.20-1.40 (m, 3H), 2.09 (s, 3H), 3.30 (m, 1H), 3.48-3.75 (m, 6H), 4.20 (m, 1H), 5.10 (m, 3H), 7.25-7.52 (m, 10H); MS (DCI/NH$_3$) m/z 291 (M+H)$^+$.

Example 1G

Benzyl (3S,4S)-3-[(tert-butoxycarbonyl)amino]-4-(hydroxymethyl)-1-pyrrolidinecarboxylate (S)-mandelate The product of Example 1E n-pentanol/ethanol was charged to a glass-lined reactor, equipped with a mechanical agitator, condenser, temperature probe and nitrogen inlet. The contents of the reactor were distilled under vacuum with a jacket temperature of NMT 85° C. to a volume of 400 L is to remove both the water and the ethanol. The internal temperature was then adjusted to 25° C. The mixture was diluted with n-pentanol to ~10% wt 1E then (S)-mandelic acid (17.0 Kg) was charged. The internal temperature of the reactor was adjusted to 75° C. to dissolve all the solids. The internal temperature was then adjusted to 60° C., at which point seed crystals (250 g) were added to the reactor. The contents of the reactor were stirred at an internal temperature of 60±5° C. for not less than 3 hours. The internal temperature of the reactor was lowered to 25° C. at a rate of 5° C. per hour, and then the contents of the reactor were stirred at 25° C. for not less than 6 hours. The contents of the reactor were filtered, and the wetcake was washed with n-pentanol (50 Kg). After the wetcake was blown dry with nitrogen for at least 4 hours, the product was dried for at least 24 hours in a hastelloy tray dryer under vacuum at 55° C., with a nitrogen bleed. A total of 27.7 Kg 18 was obtained (38%), with >99% purity and 96% diastereomeric excess.

Example 1H

Benzyl (3S,4S)-3-[(tert-butoxycarbonyl)amino]-4-(hydroxymethyl)-1-pyrrolidinecarboxylate The product of Example 1F (56 g, 127 mmol) in ethanol (50 mL) was treated with 5% aqueous H$_2$SO$_4$ (100 mL) at room temperature and allowed to stir for 16 hours. The mixture was basified to pH ~10 with 20% aqueous NaOH (50 mL) and then the mixture was treated with di-tert-butyl dicarbonate (41.5 g, 190 mmol) in ethanol (50 mL) at 10-20° C. After stirring at room temperature for 4 hours, the ethanol was removed under reduced pressure and the residue was extracted with ethyl acetate (3×500 mL). The combined organic phases were washed with brine (2×100 mL) and concentrated to provide the title compound. The enantiopurity of the title compound was determined to be greater than or equal 99% enantiomeric excess by HPLC (HPLC conditions: Chiracel AD column; ethanol/hexanes=20/80, flow rate, 1.0 mL/minute; uv 220 nm; retention time 10.8 minutes). $^1$H NMR (MeOH-d$_4$, 300 MHz) δ 1.46 (s, 9H), 2.50 (m, 1H), 3.25 (m, 1H), 3.40 (m, 1H), 3.50-3.75 (m, 4H), 4.20 (m, 1H), 5.10 (s, 2H), 7.35 (m, 5H); MS (DCI/NH$_3$) m/z 368 (M+NH$_4$)$^+$, 351 (M+H)$^+$.

Alternatively, the product of Example 1G (13.3 Kg) was charged to a glass-lined reactor with ethyl acetate (89.9 Kg) and the internal temperature adjusted to 25° C. To this slurry was charged a 50 wt % solution of aqueous potassium carbonate (73 Kg). To the stirred suspension was charged a solution of di-t-butyldicarbonate (9.4 Kg) in ethyl acetate (44.2 Kg). The reaction mixture was stirred at 25° C. until complete. The reaction mixture was quenched with N,N-dimethylethylenediamine (0.55 Kg), followed by the addition of ethyl acetate (85.8 Kg) and water (66 Kg). After separating the layers, the organic layer was washed with a solution of potassium phosphate buffer (28.4 kg). The buffer solution was made using 13.3 g potassium phosphate monobasic and 50.8 g potassium phosphate dibasic per kilogram of water. The wash was repeated until the pH of the aqueous solution after the wash was less than 8.0. The organic layer was washed with a 20 wt % solution of sodium chloride (75 kg) and was assayed by HPLC to contain 4.5 wt % intermediate 1H, corresponding to 10.23 Kg (88%). The ethyl acetate solution was distilled under vacuum. The product slurry was used immediately in the next step.

Example 1I

Benzyl (3S,4S)-3-[(tert-butoxycarbonyl)amino]-4-{[(methylsulfonyl)oxy]methyl}-1-pyrrolidinecarboxylate The product of Example 1H (43.7 g, 125 mmol) and triethylamine (25.2 g, 250 mmol) in CH$_2$Cl$_2$ (600 mL) were treated with methanesulfonyl chloride (12.6 mL, 163 mmol) over 30 minutes at −10° C. The solution was allowed to warm to room temperature over 1 hour and quenched with water (100 mL). The layers were separated and the aqueous phase was extracted with $CH_2Cl_2$ (2×400 mL). The combined organic phases were washed with brine (2×100 mL), dried over $Na_2SO_4$, filtered, and the filtrate concentrated to provide the title compound. $^1$H NMR ($CDCl_3$, 300 MHz) δ 1.46 (s, 9H), 2.80 (m, 1H), 3.08 (s, 3H), 3.40 (m, 2H), 3.70 (m, 2H), 4.10 (m, 1H), 4.40 (m, 2H), 4.75 (m, 1H), 5.16 (s, 2H), 7.30 m, 5H); MS ($DCI/NH_3$) m/z 446 $(M+NH_4)^+$, 429 $(M+H)^+$.

Example 1J

Benzyl (3S,4S)-3-amino-4-{[(methylsulfonyl)oxy]methyl}-1-pyrrolidinecarboxylate trifluoroacetate The product of Example 1I (43.7 g, 125 mmol) in $CH_2Cl_2$ (150 mL) was treated with trifluoroacetic acid (50 mL) at room temperature and allowed to stir for 1 hour. The mixture was concentrated under reduced pressure to give the title compound. $^1$H NMR ($CDCl_3$, 300 MHz) δ 2.80 (m, 1H), 3.15 (s, 3H), 3.40 (m, 1H), 3.70 (m, 3H), 4.10 (m, 1H), 4.05 (m, 1H), 4.44 (m, 2H), 5.16 (s, 2H), 7.30-7.50 (m, 5H); MS ($DCI/NH_3$) m/z 329 $(M+H)^+$.

Example 1K

Benzyl (1S,5S)-3,6-diazabicyclo[3.2.0]heptane-3-carboxylate

The product of Example 1J was dissolved in ethanol (250 mL) and basified to pH~12 with 25% aqueous NaOH. The mixture was warmed to 60° C. for 1.5 hours. The reaction mixture was allowed to cool to room temperature and used in the next step without further purification. An analytical sample was removed (~1 mL) and concentrated under reduced pressure. The residue was extracted with $CHCl_3$ (2×5 mL). The extracts were combined, washed with brine (3×2 mL) and then passed through a short column of diatomaceous earth. The filtrate was concentrated to provide an analytical amount of the title compound. $^1$H NMR (MeOH-$d_4$, 300 MHz) δ 3.30-3.16 (m, 3H), 3.36 (m, 1H), 3.82 (m, 3H), 4.55 (m, 1H), 5.20 (s, 2H), 7.36 (m, 5H); MS ($DCI/NH_3$) m/z 250 $(M+NH_4)^+$, 233 $(M+H)^+$.

Example 1L

3-Benzyl 6-tert-butyl-(1R,5S)-3,6-diazabicyclo[3.2.0]heptane-3,6-dicarboxylate

The solution of Example 1K was slowly added to di-tert-butyl dicarbonate (40.9 g, 188 mmol) in ethanol (50 mL) over 30 minutes at room temperature. The mixture was stirred at room temperature for additional 0.5-1 hours. The reaction mixture was concentrated under reduced pressure. The residue was extracted with ethyl acetate (3×500 mL). The ethyl acetate extracts were combined, washed with brine (3×50 mL), stirred with $KHSO_4$ (5%, 100 mL) for 10 minutes and the phases separated. The organic layer was washed with brine (3×50 mL) and passed through a short column of diatomaceous earth. The filtrate was concentrated to provide the title compound which was used in the next step without further purification. $^1$H NMR (MeOH-$d_4$, 300 MHz) δ 1.4 (s, 9H), 3.10 (m, 2H), 3.30 (m, 1H), 3.45 (m, 1H), 3.90 (d, J=12.2 Hz, 1H), 4.06 (m, 2H), 4.66 (dd, J=6.4, 2.0 Hz, 1H), 5.16 (s, 2H), 7.36 (m, 5H); MS ($DCI/NH_3$) m/z 333 $(M+H)^+$.

Example 1M tert-Butyl (1R,5S)-3,6-diazabicyclo[3.2.0]heptane-6-carboxylate

The product of Example 1L (40.0 g, 0.120 mol) was dissolved in methanol (400 mL) and treated with Pd/C (10 wt. %, 4.0 g) under $H_2$ at room temperature for 10 hours. The reaction mixture was filtered through a short column of diatomaceous earth and the filtrate was concentrated to provide the title compound. $^1$H NMR (MeOH-$d_4$, 300 MHz) δ 1.43 (s, 9H), 2.47 (dd, J=12.6, 3.8 Hz, 1H), 2.62 (dd, J=12.2, 5.7 Hz, 1H), 2.96 (m, 1H), 3.05 (d, J=12.2 Hz, 1H), 3.22 (d, J=12.5 Hz, 1H), 3.45 (m, 1H), 3.95 (m, 1H), 4.63 (dd, J=6.1, 3.7 Hz, 1H); MS ($DCI/NH_3$) m/z 199 $(M+H)^+$.

Example 2

5-Bromo-2,3-dichloropyridine

Example 2A

3-Chloro-5-nitro-2-pyridinol

A 5 L flask with mechanical stirrer, thermocouple, and addition funnel was charged with 2-hydroxy-5-nitropyridine (200 g) and concentrated HCl (890 mL). The mixture was warmed to 50-55° C. and a solution of $KClO_3$ (61.3 g, 0.5 mol) in water (850 mL) was added dropwise over 75 minutes maintaining the reaction temperature at 55-59° C. Following complete addition, the reaction mixture was cooled in an ice-water bath to an internal temperature of <6° C. and then filtered. The filter cake was washed with cold water (700 mL) and dried under vacuum at 50° C. for 12 hours to provide the title compound. $^1$H NMR ($CDCl_3$, 300 MHz) δ 7.43 (d, J=3 Hz, 1H), 7.59 (d, J=3 Hz, 1H).

Example 2B 2,3-Dichloro-5-nitropyridine

A 2 L flask with mechanical stirrer and thermocouple was charged with $POCl_3$ (200 g, 1.30 mol). The flask was cooled in an ice bath to an internal temperature of 0-5° C. as quinoline (84 g, 0.65 mol) was added. The product of Example 2A (227 g, 1.30 mol) was added in portions, so as to maintain the reaction temperature below 10° C. The cold bath was removed, and the mixture was warmed to 120° C. for 90 minutes. The temperature was decreased to 100° C. and the reaction mixture was quenched by addition of water (500 mL) maintaining the internal temperature between 100-110° C. After complete addition, the mixture was cooled in ice to 0-5° C. for 1 hour and filtered. The filter cake was washed with cold water and dried under vacuum at 40° C. to provide the title compound. $^1$H NMR ($CDCl_3$, 300 MHz) δ 8.39 (d, J=3 Hz, 1H), 9.16 (d, J=3 Hz, 1H).

Example 2C

5-Amino-2,3-dichloropyridine

Anhydrous $SnCl_2$ (300 g, 1.58 mol) and concentrated HCl (350 mL) were charged to a 5 L flask with mechanical stirrer and thermocouple. The flask was cooled in ice and the product of Example 2B (100 g, 0.518 mol) was added in portions maintaining the temperature below 65° C. After the addition was complete, the cold bath was removed, and the mixture was stirred for 2 hours at ambient temperature. The mixture was cooled in ice as 25% aqueous NaOH (1000 mL) was added to bring the mixture to pH>10. The mixture was extracted with CH$_2$Cl$_2$ (1×600 mL, 2×400 mL) and the combined extracts were washed with brine (200 mL), dried (MgSO$_4$), and concentrated under vacuum. The residual solid was crystallized from a mixture of water (500 mL) and ethanol (100 mL) to provide the title compound as a solid. $^1$H NMR (CDCl$_3$, 300 MHz) δ 3.80 (br s, 2H), 7.10 (d, J=3 Hz, 1H), 7.77 (d, J=3 Hz, 1H); MS (DCI/NH$_3$) m/z 180/182/184 (M+NH$_4$)$^+$ 163/165/167 (M+H)$^+$.

Example 2D

5-Bromo-2,3-dichloropyridine

A 5 L flask with mechanical stirrer, thermocouple, and addition funnel was charged with the product of Example 2C (70 g, 429 mmol) and 48% HBr$_{aq}$ (240 mL). The suspension was maintained at 0-5° C. as a solution of NaNO$_2$ (32.0 g, 464 mmol) in water (100 mL) was added dropwise over 1 hour. Additional water (200 mL) was added and the mixture was stirred for 10 minutes at 0-5° C. The mixture was treated with CuBr (32.6 g, 227 mmol) in portions over 20 minutes followed by additional water to maintain a fluid reaction mixture. The mixture was allowed to warm to room temperature and diluted with water. The mixture was distilled at ambient pressure, until the distillate ran clear (1.5 L collected). The distillate was extracted with EtOAc (3×500 mL) and the combined extracts were washed with brine (100 mL), dried (MgSO$_4$), and concentrated to provide 5-bromo-2,3-dichloropyridine as a solid. $^1$H NMR (CDCl$_3$, 300 MHz) δ 7.94 (d, J=3 Hz, 1H), 8.38 (d, J=3 Hz, 1H).

Example 3

(1S,5S)-3-(5,6-Dichloro-3-pyridinyl)-3,6-diazabicyclo[3.2.0]heptane (L)-tartrate Example 3A tert-Butyl (1R,5S)-3-(5,6-dichloro-3-pyridinyl)-3,6-diazabicyclo[3.2.0]heptane-6-carboxylate A 1 L flask with mechanical stirrer was charged with a solution of tert-butyl (1R,5S)-3,6-diazabicyclo[3.2.0]heptane-6-carboxylate (10.0 g, 50 mmol, product of Example 1L) and 5-bromo-2,3-dichloropyridine (14.0 g, from Example 2D) in toluene (400 mL). The flask was evacuated and purged three times with nitrogen. Xantphos (1.74 g, 3 mmol), Pd$_2$(dba)$_3$ (916 mg, 1 mmol) and sodium tert-butoxide (7.20 g, 75 mmol) were added successively to the flask against a purge of nitrogen gas. The flask was again evacuated and purged with nitrogen (3 times) and the mixture heated to 85-90° C. under N$_2$. After 2 hours, the reaction was cooled to room temperature, diluted with ethyl acetate (1000 mL) and water (200 mL), and stirred for 5 minutes. The organic phase was separated, washed with brine (200 mL), dried (MgSO$_4$), filtered through Celite® (diatomaceous earth) and the filtrate concentrated under vacuum to provide the title compound which was used in the next step without further purification. $^1$H NMR (MeOH-d$_4$, 300 MHz) δ 1.45 (s, 9H), 2.94 (dd, J=1.6, 4.4 Hz, 1H), 3.04 (dd, J=10.2, 6.4 Hz, 1H), 3.3 (m, 1H), 3.58 (m, 1H), 3.78 (d, J=10.5 Hz, 1H), 3.90 (d, J=10.8 Hz, 1H), 4.05 (m, 1H), 4.83 (m, 1H) 7.39 (d, J=2.7 Hz, 1H), 7.84 (d, J=2.7 Hz, 1H); MS (DCI/NH$_3$) m/z 344/346/348 (M+H)$^+$.

Example 3B (1S,5S)-3-(5,6-Dichloro-3-pyridinyl)-3,6-diazabicyclo[3.2.0]heptane p-toluenesulfonate The product of Example 3A (23.2 g) was dissolved in ethyl acetate (250 mL) and p-toluenesulfonic acid monohydrate (11.4 g, 60 mmol) was added. The solution was warmed to reflux and stirred for 90 minutes, cooled to room temperature, and allowed to stand for 12 hours to complete precipitation. The solid was isolated by filtration and dried to provide the title compound. mp 174-178° C.; [α]$_D^{20}$=−20.0° (MeOH, 0.105); $^1$H NMR (MeOH-d$_4$, 300 MHz) δ 2.36 (s, 3H), 3.06 (dd, J=10.5, 6.1 Hz, 1H), 3.17 (dd, J=12.2, 4.8 Hz, 1H), 3.50 (m, 1H), 3.72 (dd, J=11.2, 5.4 Hz, 1H), 3.90 (d, J=10.5 Hz, 1H), 4.10 (d, J=12.6 Hz, 1H), 4.25 (dd, J=11.2, 9.8 Hz, 1H), 5.05 (dd, J=6.7, 5.1 Hz, 1H) 7.22 (d, J=8.1 Hz, 2H), 7.52 (d, J=2.7 Hz, 1H), 7.69 (d, J=8.1 Hz, 2H), 7.95 (d, J=2.7 Hz, 1H); MS (DCI/NH$_3$) m/z 244/246/248 (M+H)$^+$.

Example 3C (1S,5S)-3-(5,6-Dichloropyridin-3-yl)-3,6-diaza-bicyclo[3.2.0]heptane

The product of Example 3B (33 g, 79 mmol) was stirred in 330 mL of 5% NaOH in water for 10 minutes and extracted with CHCl$_3$:i-PrOH (10:1) (4×500 mL). The extracts were combined, washed with brine (2×100 mL), and concentrated to give the title compound as a solid. $^1$H NMR (MeOH-d$_4$, 300 MHz) δ 3.04 (dd, J=10.9, 4.8 Hz, 1H), 3.11 (dd, J=10.2, 6.8 Hz, 1H), 3.26 (dd, J=8.8, 4.4 Hz, 1H), 3.38 (m, 1H), 3.73 (t, J=11.2 Hz, 2H), 3.84 (t, J=8.1 Hz, 1H), 4.55 (dd, J=6.8, 4.8 Hz, 1H), 7.37 (d, J=3.1 Hz, 1H), 7.84 (d, J=2.7 Hz, 1H); MS (DCI/NH$_3$) m/z 244/246/248 (M+H)$^+$.

Example 3D (1S,5S)-3-(5,6-Dichloro-3-pyridinyl)-3,6-diazabicyclo[3.2.0]heptane (L)-tartrate The product from Example 3C (12.0 g, 50 mmol) in MeOH (400 mL) was heated to 65° C. and treated with (L)-tartaric acid (9.0 g, 60 mmol) in MeOH (60 mL) dropwise. After complete addition, the mixture was stirred at reflux for 2 hours and then allowed to cool to room temperature. After stirring at room temperature for 10 hours, the mixture was filtered and the filter cake washed with chilled methanol (10 mL). The solid was dried under vacuum to provide the title compound. mp 210-212° C. (decomp); [α]$_D^{20}$=−27.02° (MeOH, 0.105); $^1$H NMR (MeOH-d$_4$, 300 MHz) δ 3.12 (dd, J=10.9, 6.1 Hz, 1H), 3.22 (dd, J=12.9, 5.1 Hz, 1H), 3.54 (m, 1H), 3.76 (dd, J=11.6, 5.1 Hz, 1H), 3.87 (d, J=10.9 Hz, 1H), 4.10 (d, J=12.6 Hz, 1H), 4.31 (dd, J=11.2, 8.5 Hz, 1H), 4.77 (s, 2H), 5.13 (dd, J=7.2, 5.1 Hz, 1H) 7.54 (d, J=2.7 Hz, 1H), 7.90 (d, J=2.7 Hz, 1H); MS (DCI/NH$_3$) m/z 244/246/248 (M+H)$^+$.

Example 4

(1S,5S)-3-(5,6-Dichloro-pyridin-3-yl)-3,6-diaza-bicyclo[3.2.0]heptane

The product from Example 3C (10.0 g) was partitioned between methylene chloride (200 mL) and 20% aqueous potassium hydroxide (150 mL). The layers were separated, and the organic layer was washed with more 20% aqueous potassium hydroxide (2×150 mL). The organic layer was then washed with saturated brine solution (100 mL). This was concentrated to an oily solid, and then dissolved up in isopropyl acetate. Upon concentration by distillation to ~50 mL, solids started to crystallize. More isopropyl acetate (200 mL) was added and this was concentrated to ~25 mL. After cooling in an ice bath, the resulting solids were filtered and the wetcake was washed with isopropyl acetate. The product was dried in the vacuum oven at 50° C. to give a solid. $^1$H NMR (CDCl$_3$, 400 MHZ) δ 3.04 (dd, J=11, 8 Hz, 1H), 3.15 (dd, J=10, 7 Hz, 1H), 3.30-3.38 (m, 2H), 3.6 (d, J=11 Hz, 1H), 3.88 (d, J=10 Hz, 1H), 3.91 (t, J=8 Hz, 1H), 4.60 (m, 1H), 7.07 (d, J=3 Hz, 1H), 7.75 (d, J=3 Hz, 1H).

Example 5

(1S,5S)-3-(5,6-dichloropyridin-3-yl)-3,6-diaza-bicyclo[3.2.0]heptane

Example 5A

3-Chloro-2-hydroxy-5-nitropyridine

Concentrated hydrochloric acid (239 g) was added to 2-hydroxy-5-nitropyridine (40.0 g). The resulting slurry was heated to 53° C., and stirred until all the solids dissolved. To this was slowly added a solution of potassium chlorate (14.0 g) in water (250 g), while maintaining the temperature between 55° C. and 59° C. The resulting mixture was stirred at 58-62° C. for about 1 hour. The reaction was then cooled to room temperature, stirred for 12 hours and then filtered. After washing the wet cake with water, the product was dried in a vacuum oven. $^1$H NMR (400 MHz/DMSO-d6) δ 8.64 (d, J=2.9 Hz, 1H), 8.35 (d, J=2.9 Hz, 1H)

Example 5B 2,3-Dichloro-5-nitropyridine (Compound 5B)

A mixture of 3-chloro-2-hydroxy-5-nitropyridine (36.0 g), acetonitrile (72 mL), and phosphorus oxychloride (37.5 g) was heated to 80° C. The reaction was then stirred at this temperature for about 15 hours. After cooling the reaction to 40° C., water (27 g) was added, while maintaining the temperature below 70° C. The temperature was adjusted to 45° C., and then more water (189 g) was added slowly. The reaction was then cooled to 23° C., stirred for at least 12 hours, and then filtered. After washing the wet cake with water, the product was dried in a vacuum oven. $^1$H NMR (400 MHz/CDCl$_3$) δ 9.10 (d, J=2.5 Hz, 1H), 8.56 (d, J=2.4 Hz, 1H)

Example 5C (5,6-Dichloro-pyridin-3-yl)-(2,2-dimethoxy-ethyl)-amine

To a Parr bottle was charged Raney Nickel (10.1 g), water (40.0 g), tetrahydrofuran (166.3 g), ethanol (32.0 g) and acetic acid (2.5 g). A solution of 2,3-dichloro-5-nitropyridine (40.0 g) in tetrahydrofuran (40.1 g) was added to the Parr bottle in four portions and the mixture was hydrogenated at 40 psi and 35° C. for about 1 hour after each addition. The reaction mixture was cooled to room temperature, and then glyoxal-1,2-dimethyl acetal (47.2 g of 50 wt % aqueous), tetrahydrofuran (35.6 g) and water (80.4 g) were added and the mixture was hydrogenated at 40 psi and 50° C. for about 12 hours. The reaction was cooled to room temperature and then filtered through a bed of Hy-Flo. The pH of the filtrate was adjusted to 7 with 5% aqueous phosphoric acid, and then the mixture was concentrated. Isopropyl acetate (79 g) was added, this was concentrated, and then more isopropyl acetate (485 g) was added. After warming to 50° C. to dissolve the solids, the solution was washed with 5% aqueous phosphoric acid (3×215 g) and then washed with 20% aqueous sodium chloride solution (231 g). The organic solution was concentrated to about 78 mL and heptane (124 g) was added. After heating to 83° C. to dissolve everything, the solution was slowly cooled to room temperature. More heptane (124 g) was added and then the suspension was cooled to 5° C. After filtering, the wetcake was washed with cold heptane/isopropyl acetate and then dried in the vacuum oven. $^1$H NMR (400 MHz/CDCl$_3$) δ 7.71 (d, J=2.7 Hz, 1H), 7.01 (d, J=2.7 Hz, 1H), 4.53 (t, J=5.2 Hz, 1H), 4.05 (s, br, 1H), 3.42 (s, 6H), 3.22 (d, J=5.21 Hz, 2H).

Example 5D

Allyl-(5,6-dichloro-pyridin-3-yl)-(2,2-dimethoxyethyl)-amine (Compound 5D)

To a mixture of (5,6-dichloro-pyridin-3-yl)-(2,2-dimethoxy-ethyl)-amine (190 g), allyl bromide (137.4 g), and methyl tributyl ammonium chloride (23.8 g) in methyl tert-butyl ether (1140 mL) was added 50% aqueous sodium hydroxide (665 mL). This was then stirred at 25-35° C. for about 24 hours. Then water (375 g) and methyl tert-butyl ether (280 g) were added and then the layers were separated. The organic layer was washed with 10 mM potassium phosphate dibasic/10 mM potassium phosphate monobasic aqueous solution (3×1000 mL), and then washed with 20% aqueous sodium chloride (1000 mL). The solution was concentrated to a small volume and then dissolved back up in tetrahydrofuran (1720 g). $^1$H NMR (400 MHz/CDCl$_3$) δ 7.79 (d, J=3.02 Hz, 1H), 7.10 (d, J=3.02 Hz, 1H), 5.81-5.70 (m, 1H), 5.20 (ddd, J=1.78, 3.02 10.43 Hz, 1H), 5.09 (ddd, J=1.9, 3.2, 17.1 Hz, 1H). 4.48 (t, J=5.1 Hz, 1H), 4.00-3.95 (m, 2H), 3.43 (d, J=5.1, 2H), 3.41 (s, 6H).

Example 5E 2-(S)-Hydroxyamino-2-phenyl-ethanol

A solution of (S)-phenylglycinol (15 g) and p-anisaldehyde (16.4 g) in methyl tert-butyl ether (150 mL) was heated to reflux, with a Dean-Stark trap attached, for about 3 hours. Tetrahydrofuran (60 mL) was added and the mixture cooled to 0° C. To this was added a solution of m-chloroperoxybenzoic acid (29.8 g) in methyl tert-butyl ether (80 mL), maintaining the temperature below 5° C. The mixture was stirred at 0° C. for about 3 hours. Then the reaction mixture was washed with 10% aqueous potassium carbonate (3×75 mL). The resulting organic layer was concentrated to a smaller volume. To this was added a solution of hydroxylamine hydrochloride (15.3 g) in methanol (19 mL) and water (27 mL), and the reaction was stirred at room temperature for about 3 hours. Heptane (30 mL) and water (30 mL) were added. The layers were separated, and the aqueous layer was washed with methyl tert-butyl ether (3×30 mL). The methanol was removed by vacuum distillation, and then methyl tert-butyl ether (75 ml) was added. After adjusting the pH to 7 with solid potassium carbonate, sodium chloride was added and the layers separated. The aqueous layer was further extracted with methyl tert-butyl ether (2×75 mL). The combined methyl tert-butyl ether extracts were filtered, concentrated to a small volume, and then heptane (70 mL) was added. The resulting slurry was stirred at room temperature for about 1 hour and then cooled to 0° C. After stirring for 1 hour, the mixture is filtered and the wetcake washed with heptane (20 mL). The wetcake was then dissolved in dichloromethane (100 mL) for use in the next step. $^1$H NMR (400 MHz, CDCl$_3$) δ 3.83-3.91 (2H, m), 4.12 (1H, dd, J=6.9, 4.8 Hz), 4.84 (3H, br s), 7.27-7.36 (5H, m). $^{13}$C NMR (100 MHz, CDCl$_3$) δ 63.8, 67.7, 127.5, 127.9, 128.4, 137.5.

Example 5F

[Allyl-(5,6-dichloro-pyridin-3-yl)-amino]-acetaldehyde

A solution of allyl-(5,6-dichloro-pyridin-3-yl)-(2,2-dimethoxy-ethyl)-amine (57.2 g) in tetrahydrofuran (443 g) was cooled to 10° C. A solution of concentrated hydrochloric acid (136 g) in water (114 g) was slowly added, maintaining the temperature below 20° C. The reaction was then stirred at 15° C. for about 4 hours. Then dichloromethane (570 g) and water (430 g) were added and the layers separated. The organic layer was washed with 5% aqueous sodium bicarbonate (453 g), and then washed twice with water (430 g). The organic layer was concentrated and the residue dissolved in dichloromethane (580 g).

Example 5G (3S,4S)-2-[5-(5,6-Dichloro-pyridin-3-yl)-hexahydropyrrolo[3,4-c]isoxazol-1-yl]-2-(2')-phenyl-ethanol (Compound 5G)

2-(S)-Hydroxyamino-2-phenyl-ethanol (13.8 g) was dissolved in dichloromethane (180 mL). To this was added magnesium bromide (15.9 g) and isopropyl alcohol (5.2 g). This mixture was stirred for 30 minutes, and then [allyl-(5,6-dichloro-pyridin-3-yl)-amino]-acetaldehyde (18.4 g) in dichloromethane (223 g) was added slowly. The reaction was stirred at 30° C. for about 5 hours. To the reaction was added 10% aqueous ammonium acetate (200 mL). The layers were separated and then the organic layer was washed with water (200 mL). The solution was concentrated to an oil, dissolved up in isopropyl alcohol (200 mL) and concentrated to an oil. The resulting oil was dissolved in isopropyl alcohol (100 mL) and heated to 80° C. to dissolve all the solids. The solution was cooled slowly to room temperature at which point heptane (100 mL) was added and the mixture heated to 60° C. Upon cooling to room temperature, the mixture was filtered. After washing the wet cake with isopropyl alcohol, the product was dried in a vacuum oven.

$^1$H NMR (400 MHz/CDCl$_3$) δ 7.51 (d, J=2.7 Hz, 1H), 7.33 (m, 5H), 6.83 (d, J=2.6 Hz, 1H), 4.11 (m, 1H), 3.80-3.91 (m, 3H), 3.74 (dd, J=3.5, 11.6 Hz, 1H), 3.32-3.40 (m, 3H), 3.12 (m, 2H).

Example 5H (3S,4S)-5-(5,6-Dichloro-pyridin-3-yl)-hexahydropyrrolo[3,4-c]isoxazole (Compound 5H)

A solution of (3S,4S)-2-[5-(5,6-dichloro-pyridin-3-yl)-hexahydro-pyrrolo[3,4-c]isoxazol-1-yl]-2-(2'S)-phenyl-ethanol (30 g) and triethylamine (11.2 g) in tetrahydrofuran (222 g) was cooled to 0° C. Methanesulfonyl chloride (11.1 g) was slowly added and then the mixture was stirred at 5° C. for about 1 hour. A solution of sodium tert-butoxide (21.1 g) in tetrahydrofuran (133 g) was added and then the mixture stirred at room temperature for about 2 hours. After adding water (44.5 g), the pH was adjusted to 7.9 with 3M aqueous hydrochloric acid (31 g). The solution was concentrated to about 90 mL, water (100 mL was added and then the pH was adjusted to 0.8 with 3 M aqueous hydrochloric acid (28 g). The aqueous solution was washed with toluene/heptane (1:1; 2×150 ml). Isopropyl alcohol (150 mL) was added and then the pH was adjusted to 4.4 with 10% aqueous potassium phosphate (55 g). The mixture was heated to 78° C. and then slowly cooled to 45° C. Water (325 g) was slowly added and then the product was filtered. The wetcake was slurried in isopropyl alcohol (75 mL) and water (68 mL), and then heated to 80° C. The resulting solution was cooled slowly to 35° C., at which point water (232 mL) was slowly added. After stirring at room temperature for about 5 hours, the product was filtered, washed with isopropyl alcohol/water (1:4; 30 mL) and then dried in the vacuum oven. $^1$H NMR (400 MHz/CDCl$_3$) δ 7.68 (d, J=2.9 Hz, 1H), 6.99 (d, J=2.7 Hz, 1H), 4.32 (dt, J=3.6, 11.9 Hz, 1H), 3.99-3.83 (m, 2H), 3.61-3.52 (m, 2H). 3.39 (m, 1H), 3.34 (dd, J=3.7, 10.43 Hz, 1H), 3.29 (dd, J=3.8, 9.7 Hz, 1H).

Example 5I (3S,4S)-[4-Amino-1-(5,6-dichloro-pyridin-3-yl)-pyrrolidin-3-yl]-methanol (Compound 5I)

Raney Nickel (7.5 g) was charged to a Parr reactor. To this was added a solution of (3S,4S)-5-(5,6-dichloro-pyridin-3-yl)-hexahydro-pyrrolo[3,4-c]isoxazole (50 g) in tetrahydrofuran (625 mL), ethanol (625 mL) and water (2 mL). The mixture was hydrogenated at 40 psi and room temperature for about 3 hours. The reaction mixture was filtered through a bed of HyFlo and then concentrated to about 100 mL. Isopropyl alcohol (150 mL) was added and this was concentrated to about 100 mL. More isopropyl alcohol (100 mL) was added and then the mixture was heated to 80° C. Heptane (250 mL) was added, then the mixture was cooled to room temperature and filtered. After washing the wet cake with heptane, the product was dried in a vacuum oven. $^1$H NMR (400 MHz/DMSO-d6) δ 7.61 (d, J=2.8 Hz, 1H), 7.10 (d, J=2.8 Hz, 1H), 3.63 (m, 2H), 3.50 (m, 1H), 3.43 (m, 1H), 3.30 (m, 2H), 3.13 (t, J=9 Hz, 1H), 3.05 (dd, J=3, 10 Hz, 1H).

Example 5J (1S,5S)-3-(5,6-Dichloropyridin-3-yl)-3,6-diaza-bicyclo[3.2.0]heptane (Compound 5J)

(3S,4S)-[4-Amino-1-(5,6-dichloro-pyridin-3-yl)-pyrrolidin-3-yl]-methanol (10 g) was suspended in 1,2-dimethoxyethane (100 mL) and N-methylpyyrolidinone (15 mL). The mixture was heated to 50° C. and then a solution of thionyl chloride (7.9 g) in 1,2-dimethoxyethane (35 mL) was slowly added, while maintaining the temperature below 60° C. The reaction mixture was stirred at 50° C. for about 3 hours and then cooled to room temperature. After adding water (100 mL), the 1,1-dimethoxyethane was removed by distillation. Ethanol (100 mL) and water (100 mL) were added and the pH adjusted to 11-12 with 50% aqueous sodium hydroxide. The resulting mixture was heated at 60° C. for at least 12 hours and then cooled to room temperature. After filtering through a bed of Hy-Flo, the ethanol was removed by vacuum distillation. The pH was adjusted to >12 with 50% aqueous sodium hydroxide and then extracted with isopropyl acetate (2×80 mL). The combined organic extracts were concentrated, and then suspended in isopropyl acetate (~50 mL). After heating to 80° C., the solution was cooled to room temperature while stirring rapidly. The suspension was cooled to 0° C., filtered, washed with isopropyl acetate and dried in the vacuum oven. $^1$H NMR (MeOH-d$_4$, 300 MHz) δ 3.04 (dd, J=10.9, 4.8 Hz, 1H), 3.11 (dd, J=10.2, 6.8 Hz, 1H), 3.26 (dd, J=8.8, 4.4 Hz, 1H), 3.38 (m, 1H), 3.73 (t, J=11.2 Hz, 2H), 3.84 (t, J=8.1 Hz, 1H), 4.55 (dd, J=6.8, 4.8 Hz, 1H), 7.37 (d, J=3.1 Hz, 1H), 7.84 (d, J=2.7 Hz, 1H); MS (DCI/NH$_3$) m/z 244/246/248 (M+H)$^+$.

Example 6

(1S,5S)-3-(5,6-Dichloro-pyridin-3-yl)-3,6-diaza-bicyclo[3.2.0]heptane acetate

Under N$_2$, to a solution of the product of Example 5J (122 mg, 0.5 mmol) in THF (anhydrous, 5 mL) was slowly added the solution of acetic acid (36 uL, 0.6 mmol) in THF (0.6 mL). The mixture was then stirred at ambient temperature for 6 h. White solid started to precipitate. The solid was then filtered and dried (110 mg, yield, 72%). M.p. 160-164° C. Solubility: 13.4 mg/mL (water). $^1$H NMR (CD$_3$OD, 300 MHZ) δ 1.91 (s, 3H), 3.08 (dd, J=10.5, 6.4 Hz, 1H), 3.13 (dd, J=12.2, 4.8 Hz, 1H), 3.43-3.52 (m, 1H), 3.58 (dd, J=10.5, 4.8 Hz, 1H), 3.87 (d, J=10.5 Hz, 1H), 4.01 (d, J=11.8 Hz, 1H), 4.14 (dd, J=10.5, 8.5 Hz, 1H), 4.91 (dd, J=7.1, 4.7 Hz, 1H), 7.49 (d, J=2.7 Hz, 1H), 7.93 (d, J=2.7 Hz, 1H) ppm. MS (DCI/NH$_3$) m/z 244 (M+H)$^+$, 246 (M+H)$^+$.

Example 7

(1S,5S)-3-(5,6-Dichloro-pyridin-3-yl)-3,6-diaza-bicyclo[3.2.0]heptane hemicitrate Under N$_2$, to a solution of the product of Example 5J (122 mg, 0.5 mmol) in THF (5 mL) was slowly added the solution of citric acid (115 mg, 0.6 mmol) in MeOH (0.6 mL). The mixture was then stirred at ambient temperature for 6 h. White solid started to precipitate. The solid was then filtered and dried (160 mg, yield, 94%). M.p. 165-172° C. Solubility: 15.7 mg/mL (water). $^1$H NMR (CD$_3$OD, 300 MHZ) δ 2.70 (d, J=15.2 Hz 1H), 2.78 (d, J=15.2 Hz 1H), 3.07 (dd, J=10.5, 6.5 Hz, 1H), 3.16 (dd, J=12.2, 4.7 Hz, 1H), 3.44-3.54 (m, 1H), 3.69 (dd, J=10.5, 4.8 Hz, 1H), 3.89 (d, J=10.5 Hz, 1H), 4.11 (d, J=12.2 Hz, 1H), 4.24 (dd, J=10.9, 8.5 Hz, 1H), 5.03 (dd, J=7.2, 5.1 Hz, 1H), 7.52 (d, J=3.0 Hz, 1H), 7.95 (d, J=2.8 Hz, 1H) ppm. MS (DCI/NH$_3$) m/z 244 (M+H)$^+$, 246 (M+H)$^+$.

Example 8

(1S,5S)-3-(5,6-Dichloro-pyridin-3-yl)-3,6-diaza-bicyclo[3.2.0]heptane methanesulfonate Under N$_2$, to a solution of the product of Example 5J (122 mg, 0.5 mmol) in THF (5 mL) was slowly added the solution of methylsulfonic acid (Aldrich, freshly prepared 1M in THF, 0.6 mL, 0.6 mmol). The mixture was then stirred at ambient temperature for 6 h. White solid started to precipitate. The solid was then filtered and dried (110 mg, yield, 65%). M.p. 144-152° C. Solubility: >50 mg/mL (water). $^1$H NMR (CD$_3$OD, 300 MHZ) δ 2.69 (s, 3H)), 3.07 (dd, J=10.5, 6.5 Hz, 1H), 3.18 (dd, J=12.2, 4.7 Hz, 1H), 3.44-3.52 (m, 1H), 3.73 (dd, J=10.5, 4.8 Hz, 1H), 3.91 (d, J=10.5 Hz, 1H), 4.11 (d, J=12.2 Hz, 1H), 4.26 (dd, J=10.9, 8.5 Hz, 1H), 5.04 (dd, J=7.2, 5.1 Hz, 1H), 7.54 (d, J=2.7 Hz, 1H), 7.96 (d, J=3.0 Hz, 1H) ppm. MS (DCI/NH$_3$) m/z 244 (M+H)$^+$, 246 (M+H)$^+$.

Example 9

(1S,5S)-3-(5,6-Dichloro-pyridin-3-yl)-3,6-diaza-bicyclo[3.2.0]heptane maleate

Under N$_2$, to a solution of the product of Example 5J (122 mg, 0.5 mmol) in THF (5 mL) was slowly added the solution of maleic acid (70 mg, 0.6 mmol) in MeOH (0.6 mL). The mixture was then stirred at ambient temperature for 6 h. White solid started to precipitate. The solid was then filtered and dried (140 mg, yield, 78%). M.p. 160-163° C. Solubility: 7.5 mg/mL (water). $^1$H NMR (CD$_3$OD, 300 MHZ) δ 3.07 (dd, J=10.5, 6.5 Hz, 1H), 3.18 (dd, J=12.2, 4.7 Hz, 1H), 3.44-3.56 (m, 1H), 3.73 (dd, J=10.5, 4.8 Hz, 1H), 3.91 (d, J=10.5 Hz, 1H), 4.11 (d, J=12.2 Hz, 1H), 4.26 (dd, J=10.9, 8.5 Hz, 1H), 5.05 (dd, J=7.2, 5.1 Hz, 1H), 6.27 (s, 2H), 7.53 (d, J=2.7 Hz, 1H), 7.96 (d, J=2.9 Hz, 1H) ppm. MS (DCI/NH$_3$) m/z 244 (M+H)$^+$, 246 (M+H)$^+$.

Example 10

(1S,5S)-3-(5,6-Dichloro-pyridin-3-yl)-3,6-diaza-bicyclo[3.2.0]heptane fumarate

Under N$_2$, to a solution of the product of Example 5J (122 mg, 0.5 mmol) in THF (5 mL) was slowly added the solution of fumaric acid (70 mg, 0.6 mmol) in MeOH (0.6 mL). The mixture was then stirred at ambient temperature for 6 h. White solid started to precipitate. The solid was then filtered and dried (150 mg, yield, 84%). M.p. 198-202° C. Solubility: 2.9 mg/mL (water). $^1$H NMR (CD$_3$OD, 300 MHZ) δ 3.07 (dd, J=10.5, 6.5 Hz, 1H), 3.17 (dd, J=12.2, 4.7 Hz, 1H), 3.44-3.55 (m, 1H), 3.71 (dd, J=10.5, 4.8 Hz, 1H), 3.90 (d, J=10.5 Hz, 1H), 4.11 (d, J=12.2 Hz, 1H), 4.26 (dd, J=10.9, 8.5 Hz, 1H), 5.04 (dd, J=7.2, 5.1 Hz, 1H), 6.68 (s, 2H), 7.53 (d, J=3.1 Hz, 1H), 7.96 (d, J=2.7 Hz, 1H) ppm. MS (DCI/NH$_3$) m/z 244 (M+H)$^+$, 246 (M+H)$^+$.

Example 11

(1S,5S)-3-(5,6-Dichloro-pyridin-3-yl)-3,6-diaza-bicyclo[3.2.0]heptane hydrochloride Under N$_2$, to a solution of the product of Example 5J (122 mg, 0.5 mmol) in THF (5 mL) was slowly added the solution of HCl (4M in dioxane, 0.15 mL, 0.6 mmol). The mixture was then stirred at ambient temperature for 6 h. White solid started to precipitate. The solid was then filtered and dried. MS (DCI/NH$_3$) m/z 244 (M+H)$^+$, 246 (M+H)$^+$, 280 (M+H+HCl), 282 (M+H+HCl)

Example 12

(1S,5S)-3-(5,6-Dichloro-pyridin-3-yl)-3,6-diaza-bicyclo[3.2.0]heptane (L)-tartrate To a solution of the product of Example 5J (442 mg) in 5 mL methanol was slowly added a solution of L-tartaric acid (272 mg) in methanol (2 mL). During the addition, solids started to crystallize. Upon completion of the addition, the slurry was stirred at room temperature for 10 minutes. The resulting mixture was then filtered and air-dried on the filter. $^1$H NMR (D$_2$O, 400 MHZ) δ 3.04 (dd, J=10, 6 Hz, 1H), 3.21 (dd, J=13, 5 Hz, 1H), 3.50-3.56 (m, 2H), 3.73 (m, 1H) 3.83 (d, J=11 Hz, 1H), 4.07 (d, J=13 Hz, 1H) 4.29 (m, 1H), 4.48 (s, 2H), 5.11 (m, 1H), 7.49 (d, J=3 Hz, 1H), 7.85 (d, J=3 Hz, 1H).

Example 13

(1S,5S)-3-(5,6-Dichloro-pyridin-3-yl)-3,6-diazabicyclo[3.2.0]heptane(L)-tartrate monohydrate A solution of the product of Example 12 (100 mg) in water (2 mL) was obtained by sonicating for 30 seconds followed by heating to 70° C. This solution was cooled to room temperature and then cooled in a methanol/dry-ice bath. After solids crystallized the slurry was stirred at 30° C. and then the mixture filtered to provide a white solid.

Example 14

(1S,5S)-3-(5,6-Dichloro-pyridin-3-yl)-3,6-diazabicyclo[3.2.0]heptane 4-methylbenzenesulfonate (Form II)

The product of Example 5J (500 mg) was dissolved in 1-propanol (10 mL). This solution was filtered through a 0.2-micron syringe filter. While this solution was stirred at room temperature, a solution of 4-methylbenzenesulfonic acid (324 mg) in 1-propanol (2 mL) was added. After approximately 20 seconds, solids start to precipitate. The resulting slurry was stirred at room temperature for 1 hour, and then filtered. The wetcake was washed with 1-propanol (1 mL) and then dried overnight in a vacuum oven at 50° C. The product was obtained as a white solid (614 mg). $^1$H NMR (DMSO, 400 MHZ) δ 2.27 (s, 3H), 2.96 (dd, J=10, 6 Hz, 1H), 3.09 (dd, J=12, 5 Hz, 1H), 3.38 (m, 1H), 3.56 (m, 1H), 3.88 (d, J=11 Hz, 1H), 4.06-4.12 (m, 2H), 4.94 (m, 1H), 7.08 (d, J=8 Hz, 2H), 7.47 (d, J=8 Hz, 2H), 7.51 (d, J=3 Hz, 1H), 7.94 (d, J=3 Hz, 1H).

Example 15

(1S,5S)-3-(5,6-Dichloro-pyridin-3-yl)-3,6-diazabicyclo[3.2.0]heptane 4-methylbenzenesulfonate (Form II)

A solution of the product of Example 3A (441 mg) in 1-propanol (~7 mL) was treated with activated carbon (278 mg) and then filtered through a syringe filter. To this was added 4-methylbenzenesulfonic acid monohydrate (292 mg) and the resulting mixture heated to 70° C. After stirring at 70° C. for 2.5 hours, more 4-methylbenzene sulfonic acid monohydrate was added (75 mg). After 30 minutes more toluene sulfonic acid monohydrate was added (100 mg), and after 1 hour at 70° C. the reaction was complete. The resulting slurry was cooled to room temperature and filtered. The wetcake was washed with 1-propanol and air-dried to give a solid (440 mg).

In Vitro Data

Determination of Binding Potency (1S,5S)-3-(5,6-Dichloro-3-pyridinyl)-3,6-diazabicyclo[3.2.0]heptane was subjected to an vitro assay against the nicotinic acetylcholine receptor as described below.

Binding of [$^3$H]-cytisine ([$^3$H]-CYT) to neuronal nicotinic acetylcholine receptors was accomplished using crude synaptic membrane preparations from whole rat brain (Pabreza et al., Molecular Pharmacol., 1990, 39:9). Washed membranes were stored at −80° C. prior to use. Frozen aliquots were slowly thawed and resuspended in 20 volumes of buffer (containing: 120 mM NaCl, 5 mM KCl, 2 mM MgCl$_2$, 2 mM CaCl$_2$ and 50 mM Tris-Cl, pH 7.4 @4° C.). After centrifuging at 20,000×g for 15 minutes, the pellets were resuspended in 30 volumes of buffer.

Each test compound was dissolved in water to make 10 mM stock solutions, diluted (1:100) with buffer (as above), and further taken through seven serial log dilutions to produce test solutions from $10^{-5}$ to $10^{-11}$ M.

Homogenate (containing 125-150 µg protein) was added to triplicate tubes containing the range of concentrations of test compound described above and [$^3$H]-CYT (1.25 nM) in a final volume of 500 µL. Samples were incubated for 60 minutes at 4° C., then rapidly filtered through Whatman GF/B filters presoaked in 0.5% polyethyleneimine using 3×4 mL of ice-cold buffer. The filters are counted in 4 mL of Ecolume® (ICN). Nonspecific binding was determined in the presence of 10 µM (−)-nicotine and values were expressed as a percentage of total binding. The IC$_{50}$ value was determined with the RS-1 (BBN) nonlinear least squares curve-fitting program and the IC$_{50}$ value was converted to a Ki value using the Cheng and Prusoff correction (K$_i$=IC$_{50}$/(1+[ligand]/Kd of ligand). The Ki value for (1S,5S)-3-(5,6-dichloro-3-pyridinyl)-3,6-diazabicyclo[3.2.0]heptane was determined to be 0.10 nM.

In Vivo Data

Determination of Analgesic Effect

Male Sprague Dawley rats (80-100 g) were purchased from Charles River (Portage, Mich.). Prior to surgery, animals were group-housed and maintained in a temperature regulated environment (lights on between 7:00 a.m. and 8:00 p.m.). Following nerve ligation surgery, animals were group housed. Rats had access to food and water ad libitum.

The L5 and L6 spinal nerves of anesthetized rats were tightly ligated in the manner described previously by S. H. Kim and J. M. Chung, PAIN 50:355 (1992). Briefly, an incision was made on the dorsal portion of the hip and the muscle was blunt dissected to reveal the spinal processes. The L6 transverse process was removed, and the left L5 and L6 spinal nerves were tightly ligated with 5.0 braided silk suture. The wound was cleaned, the membrane sewn with 4.0 dissolvable Vicryl suture and the skin closed with wound clips.

For the assessment of neuropathic pain, mechanical allodynia in the affected paw of animals that had undergone spinal nerve ligation was evaluated using von Frey filaments. As described previously by S. R. Chaplan, F. W. Bach, J. W. Pogrel, J. M. Chung, and T. L. Yaksh, "Quantitative assessment of tactile allodynia in the rat paw" J. Neurosci. Meth., 53:55-63 (1994) two weeks following surgery, rats were acclimated to the testing box that was constructed of plexiglass with a wire mesh floor to allow access to the planter surface of the hindpaws. Using the Dixons Up-Down method, a baseline level of allodynia was determined to have a withdrawal threshold of <4 g of pressure. (1S,5S)-3-(5,6-Dichloro-3-pyridinyl)-3,6-diazabicyclo[3.2.0]heptane, administered intraperitoneally 15 minutes before testing, caused a dose-dependent increase in the withdrawal threshold up to a maximum effect of 15 g. The EC$_{50}$ was determined to be 1 µmol/kg.

Determination of Side Effect Liability

Cells of the IMR-32 human neuroblastoma clonal line (ATCC, Rockville, Md.) were maintained in a log phase of growth according to established procedures by R. J. Lukas, "Expression of ganglia-type nicotinic acetylcholine receptors and nicotinic ligand binding sites by cells of IMR-32 human neuroblastoma clonal line" J. Pharmacol. Exp. Ther. 265: 294-302 (1993). Cells were plated out at a density of 1×10$^6$ cells per well on black-walled, clear-bottomed, 96-well plates (Costar, Cambridge, Mass.) and used approximately 72 hours after plating. All plates were coated with polyethylenimine to aid in the adherence of the cells to the plate.

Changes in the intracellular $Ca^{2+}$ content of IMR-32 cells were measured using the calcium chelating dye Fluo-4 (Molecular Probes, Eugene, Oreg.) in conjunction with a Fluorescent Imaging Plate Reader (Molecular Devices, Sunnyvale, Calif.). The cell permeant acetoxymethyl (AM) ester form of Fluo-3 was prepared to a concentration of 1 mM in anhydrous DMSO and 10% pluronic acid. The dye was then diluted to a final concentration of 4 mM in growth media and placed on the cells for 1 hour at 37° C. Black-walled 96-well plates were utilized to reduce light scattering. The unincorporated dye was removed from the cells by excessive washing with the assay buffer (HETES buffer, 20 mM Hepes, 120 mM NaCl, 5 mM KCl, 1 mM $MgCl_2$, 5 mM glucose, 500 mM atropine, and 5 mM $CaCl_2$). After addition of various concentrations of (1S5S)-3-(5,6-Dichloro-3-pyridinyl)-3,6-diazabicyclo[3.2.0]heptane, the $Ca^{2+}$ dynamics were observed in the Fluorescent Imaging Plate Reader (FLIPR) apparatus equipped with an Argon laser (wavelength, 480 nm), an automated 96 channel pipettor and a CCD camera. The intensity of the fluorescence was captured by the CCD camera every second for the first minute following the agonist addition with additional readings every 5 seconds for a total time period of 5 minutes. These images were digitally transferred to an interfaced PC and change in fluorescence intensity processed for each well. The exposure setting of the camera was 0.4 sec with an f-stop setting of 2 microns. The percent maximal intensity relative to that induced by 100 μM nicotine was plotted against the concentration of (1S5S)-3-(5,6-Dichloro-3-pyridinyl)-3,6-diazabicyclo[3.2.0]heptane and an $EC_{50}$ value of 5.5 μM was calculated. Independent measurements of 100 μM nicotine (100%) and unloaded cells (0%) were performed on each plate of cells with an average range of 20,000 fluorescence units. (1S5S)-3-(5,6-Dichloro-3-pyridinyl)-3,6-diazabicyclo[3.2.0]heptane induced calcium efflux into IMR-32 cells with an $EC_{50}$ of 5.5 μM, with a maximum efficacy 73% that of nicotine.

The IMR-32 FLIPR assay, described herein, measures cation efflux that is mediated through the ganglionic-like nicotinic acetylcholine receptor (nAChR) subtype. Agents that facilitate cation efflux of the ganglionic nAChR subtype have been linked to side effect liability such as cardiovascular pressor effects. For example, epibatidine, a known nAChR agent with cardiovascular pressor liability, was determined to have an $EC_{50}$ of 24 nM and a maximal efficacy of 137% (compared to nicotine) in the IMR-32 FLIPR assay. Both the higher (less-potent) $EC_{50}$ and the lower efficacy measured for (1S,5S)-3-(5,6-dichloro-3-pyridinyl)-3,6-diazabicyclo[3.2.0]heptane demonstrate a reduced side effect liability for (1S,5S)-3-(5,6-dichloro-3-pyridinyl)-3,6-diazabicyclo[3.2.0]heptane as compared to epibatidine.

The analgesic effect and the IMR-32 activity of (1S,5S)-3-(5,6-dichloro-3-pyridinyl)-3,6-diazabicyclo[3.2.0]heptane was compared to related analogs as illustrated in Table 1.

TABLE 1

| | Analgesic Effect $ED_{50}$ (μmol/Kg) | IMR-32 activity $EC_{50}$ (μM) | IMR-32 activity % efficacy |
|---|---|---|---|
| (1S,5S)-3-(5,6-dichloro-3-pyridinyl)-3,6-diazabicyclo[3.2.0]heptane | 1 | 5.5 | 73 |
| (1R,5R)-3-(5,6-dichloro-3-pyridinyl)-3,6-diazabicyclo[3.2.0]heptane | | 0.078 | 106 |

TABLE 1-continued

| | Analgesic Effect $ED_{50}$ (μmol/Kg) | IMR-32 activity $EC_{50}$ (μM) | IMR-32 activity % efficacy |
|---|---|---|---|
| (1S,5S)-3-(6-chloro-5-methyl-3-pyridinyl)-3,6-diazabicyclo[3.2.0]heptane | >19 | 3.4 | 94 |
| (1S,5S)-3-(5-methoxy-3-pyridinyl)-3,6-diazabicyclo[3.2.0]heptane | >19 | 3.8 | 147 |
| (1S,5S)-3-(3-pyridinyl)-3,6-diazabicyclo[3.2.0]heptane | 20 | 23.2 | 100 |
| (1S,5S)-3-(6-chloro-3-pyridinyl)-3,6-diazabicyclo[3.2.0]heptane | 11 | 1.4 | 102 |
| 5-[(1S,5S)-3,6-diazabicyclo[3.2.0]hept-3-yl]nicotinonitrile | >19 | 19.9 | 85 |
| 2-bromo-5-[(1S,5S)-3,6-diazabicyclo[3.2.0]hept-3-yl]nicotinonitrile | >19 | 1.2 | 103 |
| (1S,5S)-3-(6-bromo-5-chloro-3-pyridinyl)-3,6-diazabicyclo[3.2.0]heptane | >19 | 1.4 | 81 |

The data in Table 1 demonstrates that, compared to related analogs, (1S,5S)-3-(5,6-dichloro-3-pyridinyl)-3,6-diazabicyclo[3.2.0]heptane is a potent analgesic with reduced side effect liability. The side effect potential of the 1R,5R enantiomer evidenced by its potency in the IMR-32 FLIPR assay precluded it from being tested in the analgesic model.

The in vitro binding data, in vivo analgesic assay, and IMR-32 FLIPR assay demonstrates that (1S,5S)-3-(5,6-dichloro-3-pyridinyl)-3,6-diazabicyclo[3.2.0]heptane binds to the nicotinic acetylcholine receptor, is useful for treating pain, in particular neuropathic pain, and has a reduced side effect liability.

The ability of compounds to improve cognitive function was assessed using the spatial discrimination version of the Morris water maze (Decker et al., Eur. J. Pharmacol. 261:217-222 (1994). This test measures the ability of an animal to utilize the context of extramaze visual cues to learn the location of a platform that provides safe escape from the water. Normal animals exhibit improved performance in this task in daily testing over a five-day period, while animals with a scopolamine-induced cognitive deficit do not exhibit the learning and memory consolidation required for improved performance in this test.

Male, Long-Evans rats, 300-400 g, obtained from Charles River laboratories were used in this study. During two daily habituation sessions, rats are trained to find a visible escape platform in a pool (180 cm diameter and 60 cm high) filled to a depth of 37 cm with water made opaque with powdered milk. Water temperature is maintained at 26° C. On the second day of habituation training, latency to escape measures are obtained in order to assure that animals are assigned to groups without swim speed bias. For spatial discrimination training, two visible platforms, covered in aluminum foil, are present. The platforms remain in the same position (diagonal to each other) through 5 days of training. Only one of the platforms provides escape; the other, made of expanded polystyrene, will not support the animals' weight. Rats receive six trials/day, with start position changed from trial to trial. The number of contacts with the incorrect platform (errors) serves as the dependent variable.

A cognitive deficit, as measured by increased number of errors in the water maze test, is induced by i.p. administration of the muscarinic antagonist scopolamine·HBr (0.3 mg/kg), dosed 15 min prior to each daily discrimination training session (over five days total). Administration of (1S,5S)-3-(5,6-dichloro-3-pyridinyl)-3,6-diazabicyclo[3.2.0]heptane at doses in the range of about 0.001 to about 5 μmol/kg, 30 minutes prior to the test (15 minutes prior to scopolamine) reversed the cognitive deficit and normalized the performance of the animals in the water maze.

The Morris water maze indicates that (1S,5S)-3-(5,6-dichloro-3-pyridinyl)-3,6-diazabicyclo[3.2.0]heptane has utility in disease states involving cognitive deficits including, but not limited to, Alzheimer's disease, memory dysfunction, Parkinson's disease, senile dementia, attention deficit hyperactivity disorder, schizophrenia, and other cognitive impairments.

It is to be understood that (1S,5S)-3-(5,6-dichloro-3-pyridinyl)-3,6-diazabicyclo[3.2.0]heptane has utility in disease states involving cognitive deficits and can be used in combination with other pharmaceutically acceptable cognitive enhancing active compounds.

(1S,5S)-3-(5,6-Dichloro-3-pyridinyl)-3,6-diazabicyclo[3.2.0]heptane can be used to treat pain via nicotinic acetylcholine receptors and as further described by M. Williams and S. P. Americ, "Beyond the Tobacco Debate: dissecting out the therapeutic potential of nicotine" Exp. Opin. Invest. Drugs 5(8):1035-1045 (1996); and S. P. Americ, J. P. Sullivan, M. Williams, "Neuronal nicotinic acetylcholine receptors. Novel targets for central nervous system theraputics" Psychopharmacology: The Fourth Generation of Progress. F. E. Bloom and D. J. Kupfer (Eds.), Raven Press, New York 95-109 (1995).

Additionally, (1S,5S)-3-(5,6-dichloro-3-pyridinyl)-3,6-diazabicyclo[3.2.0]heptane is useful for ameliorating or preventing disorders affected by nicotinic acetylcholine receptors, such as Alzheimer's disease, Parkinson's disease, memory dysfunction, Tourette's syndrome, sleep disorders, attention deficit hyperactivity disorder, neurodegeneration, inflammation, neuroprotection, anxiety, depression, mania, schizophrenia, anorexia and other eating disorders, AIDS-induced dementia, epilepsy, urinary incontinence, substance abuse, smoking cessation and inflammatory bowel syndrome.

Compounds that bind to the nicotinic acetylcholine receptor can be used to treat Alzheimer's disease as described by M. Williams and S. P. Americ, "Beyond the Tobacco Debate: dissecting out the therapeutic potential of nicotine" Exp. Opin. Invest. Drugs 5(8):1035-1045 (1996); S. P. Americ, J. P. Sullivan, M. Williams, "Neuronal nicotinic acetylcholine receptors. Novel targets for central nervous system theraputics" Psychopharmacology: The Fourth Generation of Progress. F. E. Bloom and D. J. Kupfer (Eds.), Raven Press, New York 95-109 (1995); S. P. Americ, M. W. Holladay, J. P. Sullivan, "Cholinergic channel modulators as a novel therapeutic strategy for Alzheimer's disease" Exp. Opin. Invest. Drugs 5(1):79-100 (1996); J. Lindstrom, "Nicotinic Acetylchloline Receptors in Health and Disease" Molecular Neurobiology 15:193-222 (1997); and G. K. Lloyd, et al., "The potential of subtype selective neuronal nicotinic acetylcholine receptor agonists as therapeutic agents" Life Sciences 62(17/18):1601-1606 (1998).

Compounds that bind to the nicotinic acetylcholine receptor can be used to treat Parkinson's disease as described by M. Williams and S. P. Americ, "Beyond the Tobacco Debate: dissecting out the therapeutic potential of nicotine" Exp. Opin. Invest. Drugs 5(8):1035-1045 (1996); J. Lindstrom, "Nicotinic Acetylchloline Receptors in Health and Disease" Molecular Neurobiology 15:193-222 (1997); and G. K. Lloyd, et al., "The potential of subtype selective neuronal nicotinic acetylcholine receptor agonists as therapeutic agents" Life Sciences 62(17/18):1601-1606 (1998).

Compounds that bind to the nicotinic acetylcholine receptor can be used to treat memory dysfunction as described by M. Williams and S. P. Americ, "Beyond the Tobacco Debate: dissecting out the therapeutic potential of nicotine" Exp. Opin. Invest. Drugs 5(8):1035-1045 (1996); S. P. Americ, J. P. Sullivan, M. Williams, "Neuronal nicotinic acetylcholine receptors. Novel targets for central nervous system theraputics" Psychopharmacology: The Fourth Generation of Progress. F. E. Bloom and D. J. Kupfer (Eds.), Raven Press, New York 95-109 (1995); and J. Lindstrom, "Nicotinic Acetylchloline Receptors in Health and Disease" Molecular Neurobiology 15:193-222 (1997).

Compounds that bind to the nicotinic acetylcholine receptor can be used to treat Tourette's syndrome as described by M. Williams and S. P. Americ, "Beyond the Tobacco Debate: dissecting out the therapeutic potential of nicotine" Exp. Opin. Invest. Drugs 5(8):1035-1045 (1996); S. P. Americ, J. P. Sullivan, M. Williams, "Neuronal nicotinic acetylcholine receptors. Novel targets for central nervous system theraputics" Psychopharmacology: The Fourth Generation of Progress. F. E. Bloom and D. J. Kupfer (Eds.), Raven Press, New York 95-109 (1995); and J. Lindstrom, "Nicotinic Acetylchloline Receptors in Health and Disease" Molecular Neurobiology 15:193-222 (1997).

Compounds that bind to the nicotinic acetylcholine receptor can be used to treat sleeping disorders as described by M. Williams and S. P. Americ, "Beyond the Tobacco Debate: dissecting out the therapeutic potential of nicotine" Exp. Opin. Invest. Drugs 5(8):1035-1045 (1996).

Compounds that bind to the nicotinic acetylcholine receptor can be used to treat attention deficit hyperactivity disorder as described by M. Williams and S. P. Americ, "Beyond the Tobacco Debate: dissecting out the therapeutic potential of nicotine" Exp. Opin. Invest. Drugs 5(8):1035-1045 (1996); and S. P. Americ, M. W. Holladay, J. P. Sullivan, "Cholinergic channel modulators as a novel therapeutic strategy for Alzheimer's disease" Exp. Opin. Invest. Drugs 5(1):79-100 (1996).

Compounds that bind to the nicotinic acetylcholine receptor can be used to treat neurodegeneration and to provide neuroprotection as described by S. P. Americ, J. P. Sullivan, M. Williams, "Neuronal nicotinic acetylcholine receptors. Novel targets for central nervous system theraputics" Psychopharmacology: The Fourth Generation of Progress. F. E. Bloom and D. J. Kupfer (Eds.), Raven Press, New York 95-109 (1995); and S. P. Americ, M. W. Holladay, J. P. Sullivan, "Cholinergic channel modulators as a novel therapeutic strategy for Alzheimer's disease" Exp. Opin. Invest. Drugs 5(1):79-100 (1996).

Compounds that bind to the nicotinic acetylcholine receptor can be used to treat inflammation as described by S. P. Americ, J. P. Sullivan, M. Williams, "Neuronal nicotinic acetylcholine receptors. Novel targets for central nervous system theraputics" Psychopharmacology: The Fourth Generation of Progress. F. E. Bloom and D. J. Kupfer (Eds.), Raven Press, New York 95-109 (1995); and S. P. Americ, M. W. Holladay, J. P. Sullivan, "Cholinergic channel modulators as a novel therapeutic strategy for Alzheimer's disease" Exp. Opin. Invest. Drugs 5(1):79-100 (1996).

Compounds that bind to the nicotinic acetylcholine receptor can be used to treat amyotrophic lateral sclerosis as described by M. Williams and S. P Americ, "Beyond the Tobacco Debate: dissecting out the therapeutic potential of nicotine" Exp. Opin. Invest. Drugs 5(8):1035-1045 (1996); S. P. Americ, J. P. Sullivan, M. Williams, "Neuronal nicotinic acetylcholine receptors. Novel targets for central nervous system theraputics" Psychopharmacology: The Fourth Generation of Progress. F. E. Bloom and D. J. Kupfer (Eds.), Raven Press, New York 95-109 (1995); and S. P. Americ, M. W. Holladay, J. P. Sullivan, "Cholinergic channel modulators as a novel therapeutic strategy for Alzheimer's disease" Exp. Opin. Invest. Drugs 5(1):79-100 (1996).

Compounds that bind to the nicotinic acetylcholine receptor can be used to treat anxiety as described by M. Williams and S. P Americ, "Beyond the Tobacco Debate: dissecting out the therapeutic potential of nicotine" Exp. Opin. Invest. Drugs 5(8):1035-1045 (1996); S. P. Americ, J. P. Sullivan, M. Williams, "Neuronal nicotinic acetylcholine receptors. Novel targets for central nervous system theraputics" Psychopharmacology: The Fourth Generation of Progress. F. E. Bloom and D. J. Kupfer (Eds.), Raven Press, New York 95-109 (1995); and S. P. Americ, M. W. Holladay, J. P. Sullivan, "Cholinergic channel modulators as a novel therapeutic strategy for Alzheimer's disease" Exp. Opin. Invest. Drugs 5(1): 79-100 (1996).

Compounds that bind to the nicotinic acetylcholine receptor can be used to treat depression as described by S. P. Americ, J. P. Sullivan, M. Williams, "Neuronal nicotinic acetylcholine receptors. Novel targets for central nervous system theraputics" Psychopharmacology: The Fourth Generation of Progress. F. E. Bloom and D. J. Kupfer (Eds.), Raven Press, New York 95-109 (1995).

Compounds that bind to the nicotinic acetylcholine receptor can be used to treat mania and schizophrenia can be demonstrated by M. Williams and S. P Americ, "Beyond the Tobacco Debate: dissecting out the therapeutic potential of nicotine" Exp. Opin. Invest. Drugs 5(8):1035-1045 (1996); S. P. Americ, J. P. Sullivan, M. Williams, "Neuronal nicotinic acetylcholine receptors. Novel targets for central nervous system theraputics" Psychopharmacology: The Fourth Generation of Progress. F. E. Bloom and D. J. Kupfer (Eds.), Raven Press, New York 95-109 (1995); and J. Lindstrom, "Nicotinic Acetylchloline Receptors in Health and Disease" Molecular Neurobiology 15:193-222 (1997).

Compounds that bind to the nicotinic acetylcholine receptor can be used to treat anorexia and other eating disorders as described by M. Williams and S. P Americ, "Beyond the Tobacco Debate: dissecting out the therapeutic potential of nicotine" Exp. Opin. Invest. Drugs 5(8):1035-1045 (1996); S. P. Americ, J. P. Sullivan, M. Williams, "Neuronal nicotinic acetylcholine receptors. Novel targets for central nervous system theraputics" Psychopharmacology: The Fourth Generation of Progress. F. E. Bloom and D. J. Kupfer (Eds.), Raven Press, New York 95-109 (1995); and J. Lindstrom, "Nicotinic Acetylchloline Receptors in Health and Disease" Molecular Neurobiology 15:193-222 (1997).

Compounds that bind to the nicotinic acetylcholine receptor can be used to treat AIDS-induced dementia as described by M. Williams and S. P Americ, "Beyond the Tobacco Debate: dissecting out the therapeutic potential of nicotine" Exp. Opin. Invest. Drugs 5(8):1035-1045 (1996); S. P. Americ, J. P. Sullivan, M. Williams, "Neuronal nicotinic acetylcholine receptors. Novel targets for central nervous system theraputics" Psychopharmacology: The Fourth Generation of Progress. F. E. Bloom and D. J. Kupfer (Eds.), Raven Press, New York 95-109 (1995); and J. Lindstrom, "Nicotinic Acetylchloline Receptors in Health and Disease" Molecular Neurobiology 15:193-222 (1997).

Compounds that bind to the nicotinic acetylcholine receptor can be used to treat epilepsy as described by M. Williams and S. P Americ, "Beyond the Tobacco Debate: dissecting out the therapeutic potential of nicotine" Exp. Opin. Invest. Drugs 5(8): 1035-1045 (1996); S. P. Americ, J. P. Sullivan, M. Williams, "Neuronal nicotinic acetylcholine receptors. Novel targets for central nervous system theraputics" Psychopharmacology: The Fourth Generation of Progress. F. E. Bloom and D. J. Kupfer (Eds.), Raven Press, New York 95-109 (1995); and J. Lindstrom, "Nicotinic Acetylchloline Receptors in Health and Disease" Molecular Neurobiology 15:193-222 (1997).

Compounds that bind to the nicotinic acetylcholine receptor can be used to treat urinary incontinence as described by M. Williams and S. P Americ, "Beyond the Tobacco Debate: dissecting out the therapeutic potential of nicotine" Exp. Opin. Invest. Drugs 5(8):1035-1045 (1996).

Compounds that bind to the nicotinic acetylcholine receptor can be used to treat premenstrual syndrome can be demonstrated by M. Williams and S. P Americ, "Beyond the Tobacco Debate: dissecting out the therapeutic potential of nicotine" Exp. Opin. Invest. Drugs 5(8):1035-1045 (1996); and S. P. Americ, J. P. Sullivan, M. Williams, "Neuronal nicotinic acetylcholine receptors. Novel targets for central nervous system theraputics" Psychopharmacology: The Fourth Generation of Progress. F. E. Bloom and D. J. Kupfer (Eds.), Raven Press, New York 95-109 (1995).

Compounds that bind to the nicotinic acetylcholine receptor can be used to treat substance abuse as described by M. Williams and S. P Americ, "Beyond the Tobacco Debate: dissecting out the therapeutic potential of nicotine" Exp. Opin. Invest. Drugs 5(8):1035-1045 (1996); and S. P. Americ, J. P. Sullivan, M. Williams, "Neuronal nicotinic acetylcholine receptors. Novel targets for central nervous system theraputics" Psychopharmacology: The Fourth Generation of Progress. F. E. Bloom and D. J. Kupfer (Eds.), Raven Press, New York 95-109 (1995).

Compounds that bind to the nicotinic acetylcholine receptor can be used to treat smoking cessation as described by M. Williams and S. P Americ, "Beyond the Tobacco Debate: dissecting out the therapeutic potential of nicotine" Exp. Opin. Invest. Drugs 5(8):1035-1045 (1996); and S. P. Americ, J. P. Sullivan, M. Williams, "Neuronal nicotinic acetylcholine receptors. Novel targets for central nervous system theraputics" Psychopharmacology: The Fourth Generation of Progress. F. E. Bloom and D. J. Kupfer (Eds.), Raven Press, New York 95-109 (1995).

Compounds that bind to the nicotinic acetylcholine receptor can be used to treat inflammatory bowel syndrome. M. Williams and S. P Americ, "Beyond the Tobacco Debate: dissecting out the therapeutic potential of nicotine" Exp. Opin. Invest. Drugs 5(8):1035-1045 (1996); and J. Lindstrom, "Nicotinic Acetylchloline Receptors in Health and Disease" Molecular Neurobiology 15:193-222 (1997).

The present invention also provides pharmaceutical compositions that comprise (1S,5S)-3-(5,6-dichloro-3-pyridinyl)-3,6-diazabicyclo[3.2.0]heptane. The pharmaceutical compositions comprise (1S,5S)-3-(5,6-dichloro-3-pyridinyl)-3,6-diazabicyclo[3.2.0]heptane formulated together with one or more non-toxic pharmaceutically acceptable carriers.

The pharmaceutical compositions of this invention can be administered to humans and other mammals orally, rectally, parenterally, intracisternally, intravaginally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of (1S,5S)-3-(5,6-dichloro-3-pyridinyl)-3,6-diazabicyclo[3.2.0]heptane, it is desirable to slow the absorption of the (1S,5S)-3-(5,6-dichloro-3-pyridinyl)-3,6-diazabicyclo[3.2.0]heptane from subcutaneous or intramuscular injection. This can be accomplished by the use of a liquid suspension of crystalline or amorphous material with poor water solubility. The rate of absorption of (1S,5S)-3-(5,6-dichloro-3-pyridinyl)-3,6-diazabicyclo[3.2.0]heptane then depends upon its rate of dissolution which, in turn, may depend upon crystal size and crystalline form. Alternatively, delayed absorption of a parenterally administered (1S,5S)-3-(5,6-dichloro-3-pyridinyl)-3,6-diazabicyclo[3.2.0]heptane is accomplished by dissolving or suspending (1S,5S)-3-(5,6-dichloro-3-pyridinyl)-3,6-diazabicyclo[3.2.0]heptane in an oil vehicle.

Injectable depot forms are made by forming microencapsule matrices of the drug in biodegradable polymers such as polylactide-polyglycolide. Depending upon the ratio of (1S,5S)-3-(5,6-dichloro-3-pyridinyl)-3,6-diazabicyclo[3.2.0]heptane to polymer and the nature of the particular polymer employed, the rate of (1S,5S)-3-(5,6-dichloro-3-pyridinyl)-3,6-diazabicyclo[3.2.0]heptane release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, (1S,5S)-3-(5,6-dichloro-3-pyridinyl)-3,6-diazabicyclo[3.2.0]heptane may be mixed with at least one inert, pharmaceutically acceptable carrier or excipient, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

(1S,5S)-3-(5,6-Dichloro-3-pyridinyl)-3,6-diazabicyclo [3.2.0]heptane can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to (1S,5S)-3-(5,6-dichloro-3-pyridinyl)-3,6-diazabicyclo[3.2.0]heptane, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to (1S,5S)-3-(5,6-dichloro-3-pyridinyl)-3,6-diazabicyclo[3.2.0]heptane, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing (1S,5S)-3-(5,6-dichloro-3-pyridinyl)-3,6-diazabicyclo[3.2.0]heptane with suitable non-irritating carriers or carriers such as cocoa butter, polyethylene glycol or a suppository wax which are solid at room temperature but liquid at body temperature and therefore melt in the rectum or vaginal cavity and release (1S,5S)-3-(5,6-dichloro-3-pyridinyl)-3,6-diazabicyclo[3.2.0]heptane.

(1S,5S)-3-(5,6-Dichloro-3-pyridinyl)-3,6-diazabicyclo[3.2.0]heptane can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to (1S,5S)-3-(5,6-dichloro-3-pyridinyl)-3,6-diazabicyclo[3.2.0]heptane, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of (1S,5S)-3-(5,6-dichloro-3-pyridinyl)-3,6-diazabicyclo[3.2.0]heptane include powders, sprays, ointments and inhalants. (1S,5S)-3-(5,6-Dichloro-3-pyridinyl)-3,6-diazabicyclo[3.2.0]heptane may be mixed under sterile conditions with a pharmaceutically acceptable carrier and any needed preservatives, buffers or propellants which may be required. Opthalmic formulations, eye ointments, powders and solutions are also contemplated as being within the scope of this invention.

Actual dosage levels of (1S,5S)-3-(5,6-dichloro-3-pyridinyl)-3,6-diazabicyclo[3.2.0]heptane in the pharmaceutical compositions of this invention can be varied so as to obtain an amount of (1S,5S)-3-(5,6-dichloro-3-pyridinyl)-3,6-diazabicyclo[3.2.0]heptane which is effective to achieve the desired therapeutic response for a particular patient, compositions and mode of administration. The selected dosage level will depend upon the activity of (1S,5S)-3-(5,6-dichloro-3-pyridinyl)-3,6-diazabicyclo[3.2.0]heptane, the route of administration, the severity of the condition being treated and the condition and prior medical history of the patient being treated.

When used in the above or other treatments, a therapeutically effective amount of (1S,5S)-3-(5,6-dichloro-3-pyridinyl)-3,6-diazabicyclo[3.2.0]heptane can be employed in pure form or, where such forms exist, in pharmaceutically acceptable salt, ester or prodrug form. The phrase "therapeutically effective amount" of (1S,5S)-3-(5,6-dichloro-3-pyridinyl)-3,6-diazabicyclo[3.2.0]heptane means a sufficient amount of the compound to treat disorders, at a reasonable benefit/risk ratio applicable to any medical treatment. It will be understood, however, that the total daily usage of (1S,5S)-3-(5,6-dichloro-3-pyridinyl)-3,6-diazabicyclo[3.2.0]heptane and compositions of the present invention will be decided by the attending physician within the scope of sound medical judgement. The specific therapeutically effective dose level for any particular patient will depend upon a variety of factors including the disorder being treated and the severity of the disorder; activity of (1S,5S)-3-(5,6-dichloro-3-pyridinyl)-3,6-diazabicyclo[3.2.0]heptane; the specific composition employed; the age, body weight, general health, sex and diet of the patient; the time of administration, route of administration, and rate of excretion of (1S,5S)-3-(5,6-dichloro-3-pyridinyl)-3,6-diazabicyclo[3.2.0]heptane; the duration of the treatment; drugs used in combination or coincidental with (1S,5S)-3-(5,6-dichloro-3-pyridinyl)-3,6-diazabicyclo[3.2.0]heptane; and like factors well known in the medical arts.

The term "pharmaceutically acceptable salt," as used herein, means salts derived from inorganic or organic acids. The salts can be prepared in situ during the final isolation and purification of (1S,5S)-3-(5,6-dichloro-3-pyridinyl)-3,6-diazabicyclo[3.2.0]heptane or separately by reacting the free base of (1S,5S)-3-(5,6-dichloro-3-pyridinyl)-3,6-diazabicyclo[3.2.0]heptane with an inorganic or organic acid. Representative acid addition salts include, but are not limited to, acetate, adipate, alginate, citrate, aspartate, benzoate, benzenesulfonate, bisulfate, butyrate, camphorate, camphorsulfonate, citrate, digluconate, glycerophosphate, hemicitrate, hemisulfate, heptanoate, hexanoate, fumarate, hydrochloride, dihydrochloride, hydrobromide, hydroiodide, 2-hydroxyethansulfonate (isethionate), lactate, maleate, fumarate, methanesulfonate, nicotinate, 2-naphthalenesulfonate, oxalate, pamoate, pectinate, persulfate, 3-phenylpropionate, picrate, pivalate, propionate, succinate, sulfate, L-tartrate, bis(L-tartrate), D-tartrate, bis(D-tartrate), DL-tartrate, bis(DL-tartrate), thiocyanate, phosphate, glutamate, bicarbonate, p-toluenesulfonate (4-methylbenzenesulfonate), trifluoroacetate, and undecanoate. More particularly, the invention contemplates and includes acetate, citrate, fumarate, hemicitrate, hydrochloride, maleate, methanesulfonate, 4-methylbenzenesulfonate, sulfate, L-tartrate, and trifluoroacetate.

The term "pharmaceutically acceptable amide," as used herein, means amides of (1S,5S)-3-(5,6-dichloro-3-pyridinyl)-3,6-diazabicyclo[3.2.0]heptane which are, within the scope of sound medical judgement, suitable for use in contact with the tissues of humans and lower animals without undue toxicity, irritation, allergic response, and the like. Amides of (1S,5S)-3-(5,6-dichloro-3-pyridinyl)-3,6-diazabicyclo[3.2.0]heptane may be prepared according to conventional methods. Representative examples include, but are not limited to, (1R,5S)-6-acetyl-3-(5,6-dichloro-3-pyridinyl)-3,6-diazabicyclo[3.2.0]heptane and (1R,5S)-6-benzoyl-3-(5,6-dichloro-3-pyridinyl)-3,6-diazabicyclo[3.2.0]heptane.

The term "pharmaceutically acceptable prodrug," as used herein, means prodrugs of (1S,5S)-3-(5,6-dichloro-3-pyridinyl)-3,6-diazabicyclo[3.2.0]heptane which are, within the scope of sound medical judgement, suitable for use in contact with the tissues of humans and lower animals without undue toxicity, irritation, allergic response, and the like. Prodrugs of (1S,5S)-3-(5,6-dichloro-3-pyridinyl)-3,6-diazabicyclo[3.2.0]heptane may be rapidly transformed in vivo to (1S,5S)-3-(5,6-dichloro-3-pyridinyl)-3,6-diazabicyclo[3.2.0]heptane, for example, by hydrolysis in blood.

The present invention contemplates formation of (1S,5S)-3-(5,6-dichloro-3-pyridinyl)-3,6-diazabicyclo[3.2.0]heptane by synthetic means or formation by in vivo biotransformation.

(1S,5S)-3-(5,6-Dichloro-3-pyridinyl)-3,6-diazabicyclo[3.2.0]heptane can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

The total daily dose of (1S,5S)-3-(5,6-dichloro-3-pyridinyl)-3,6-diazabicyclo[3.2.0]heptane administered to a human or lower animal may range from about 0.001 to about 1000 mg/kg/day. For purposes of oral administration, more preferable doses can be in the range of from about 0.1 to about 50 mg/kg/day. If desired, the effective daily dose can be divided into multiple doses for purposes of administration; consequently, single dose compositions may contain such amounts or submultiples thereof to make up the daily dose.

What is claimed is:

1. A process for preparing compound (5J),

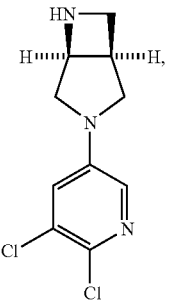

comprising the steps of:
a) treating compound (5D),

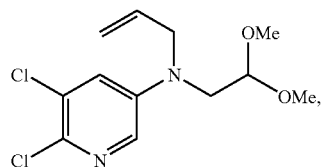

with an aqueous acid;
b) treating the mixture from step (a) with a compound of formula (A),

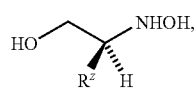

wherein $R^z$ is phenyl optionally substituted with alkyl, alkoxy or halo in the presence of magnesium bromide in a mixture of isopropyl alcohol and dichloromethane to provide a compound of formula (B),

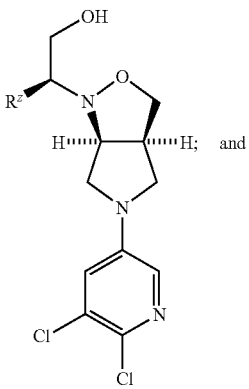

c) using the compound of formula (B) to preparing the compound (5J).

2. The process of claim 1, wherein compound (5J) is prepared from the compound of formula (B) by a process comprising the steps of:
a) treating the compound of formula (B) with a reagent that will convert the hydroxyl group into a leaving group;
b) treating the compound from step (a) with potassium tert-butoxide under heated conditions;
c) treating the compound from step (b) with an aqueous acid to obtain a pH<1 followed by adjusting the pH to 4-5 to provide compound (5H),

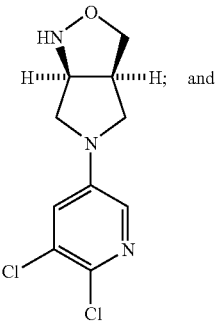

d) using compound (5H) to prepare compound (5J).

* * * * *

UNITED STATES PATENT AND TRADEMARK OFFICE
CERTIFICATE OF CORRECTION

PATENT NO.        : 7,538,226 B2
APPLICATION NO.   : 11/838745
DATED             : May 26, 2009
INVENTOR(S)       : Michael J. Buckley et al.

It is certified that error appears in the above-identified patent and that said Letters Patent is hereby corrected as shown below:

Column 10, line 58, "These transformation may be" to read as --These transformations may be--

Column 10, line 60, "for these transformation include" to read as --for these transformations include--

Column 13, line 15, "The contents of the reactor was" to read as --The contents of the reactor were--

Column 22, line 53, "methylpyyrolidinone" to read as --methylpyrrolidinone--

Column 23, line 19, "36 uL" to read as --36 µL--

Signed and Sealed this

Twenty-seventh Day of April, 2010

David J. Kappos
*Director of the United States Patent and Trademark Office*